United States Patent
Firooznia et al.

(10) Patent No.: US 9,000,044 B2
(45) Date of Patent: Apr. 7, 2015

(54) SUBSTITUTED NAPHTHYLACETIC ACIDS

(71) Applicant: Hoffmann-La Roche Inc., Nutley, NJ (US)

(72) Inventors: Fariborz Firooznia, Florham Park, NJ (US); Tai-An Lin, Pequannock, NJ (US); Eric Mertz, Fair Lawn, NJ (US); Sung-Sau So, Verona, NJ (US); Achyutharao Sidduri, West Orange, NJ (US); Jefferson Wright Tilley, North Caldwell, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 226 days.

(21) Appl. No.: 13/767,143

(22) Filed: Feb. 14, 2013

(65) Prior Publication Data
US 2013/0225588 A1 Aug. 29, 2013

Related U.S. Application Data

(60) Provisional application No. 61/604,003, filed on Feb. 28, 2012.

(51) Int. Cl.
| | |
|---|---|
| *C07C 317/44* | (2006.01) |
| *C07C 233/54* | (2006.01) |
| *C07D 213/71* | (2006.01) |
| *C07D 207/48* | (2006.01) |
| *C07D 295/26* | (2006.01) |
| *C07C 275/42* | (2006.01) |
| *C07C 311/21* | (2006.01) |
| *C07C 233/87* | (2006.01) |
| *C07C 311/16* | (2006.01) |
| *C07C 311/17* | (2006.01) |
| *C07C 311/20* | (2006.01) |

(52) U.S. Cl.
CPC .......... *C07C 317/44* (2013.01); *C07D 207/48* (2013.01); *C07D 295/26* (2013.01); *C07D 213/71* (2013.01); *C07C 233/54* (2013.01); *C07C 275/42* (2013.01); *C07C 311/21* (2013.01); *C07C 233/87* (2013.01); *C07C 311/16* (2013.01); *C07C 311/17* (2013.01); *C07C 311/20* (2013.01); *C07C 2101/14* (2013.01) 562/427

(58) Field of Classification Search
None
See application file for complete search history.

(56) References Cited

U.S. PATENT DOCUMENTS

| | | |
|---|---|---|
| 3,899,529 A | 8/1975 | Witzel |
| 4,371,537 A | 2/1983 | Markley et al. |
| 4,443,462 A | 4/1984 | Carr et al. |
| 4,868,331 A | 9/1989 | Niewoehner et al. |
| 4,921,998 A | 5/1990 | Niewoehner et al. |
| 5,424,481 A | 6/1995 | Hagen et al. |
| 7,226,951 B2 | 6/2007 | Vasudevan et al. |
| 2005/0014749 A1 | 1/2005 | Chen et al. |
| 2006/0154965 A1 | 7/2006 | Harris et al. |
| 2007/0161698 A1 | 7/2007 | Chien et al. |
| 2010/0016368 A1 | 1/2010 | Chen et al. |
| 2010/0016369 A1 | 1/2010 | Chen et al. |
| 2010/0041713 A1 | 2/2010 | Firooznia et al. |
| 2010/0041714 A1 | 2/2010 | Blanc et al. |
| 2010/0041760 A1 | 2/2010 | Blanc et al. |
| 2010/0125058 A1 | 5/2010 | Chen et al. |
| 2010/0125061 A1 | 5/2010 | Firooznia et al. |
| 2010/0137250 A1 | 6/2010 | Firooznia et al. |

FOREIGN PATENT DOCUMENTS

| | | |
|---|---|---|
| WO | 2010/055004 | 5/2010 |
| WO | 2010/055005 | 5/2010 |
| WO | 2010/055006 | 5/2010 |

OTHER PUBLICATIONS

The International Search Report and Written Opinion, issued on May 6, 2013, in the corresponding PCT Patent Application No. PCT/EP2013/053916., pp. 9.

Ulven et al, "Targeting the Prostaglandin D2 Receptors DP and CRTH2 for Treatment of Inflammation," Current Topics in Medicinal Chemistry, vol. 6, No. 1, pp. 1427-1444, 2006, XP008104082., pp. 18.

*Primary Examiner* — Bong-Sook Baek

(57) ABSTRACT

The invention is concerned with the compounds of formula (I):

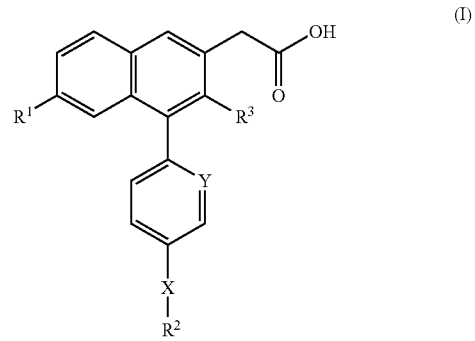

and pharmaceutically acceptable salts thereof, wherein $R^1$, $R^2$, $R^3$ and X are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

23 Claims, No Drawings

US 9,000,044 B2

SUBSTITUTED NAPHTHYLACETIC ACIDS

PRIORITY TO RELATED APPLICATION(S)

This application claims the benefit of U.S. Provisional Application No. 61/604,003, filed Feb. 28, 2012 the contents of which is hereby incorporated by reference.

RELATED APPLICATIONS

This application is related to U.S. application Ser. Nos. 12/614,485, filed Nov. 9, 2009; 12/614,478, filed Nov. 9, 2009; and 12/614,497, filed Nov. 9, 2009. The entire contents of these applications are expressly incorporated by reference herein.

BACKGROUND OF THE INVENTION

The present invention relates to novel substituted naphthalene-2-yl acetic acids, their manufacture, pharmaceutical compositions containing them and their use as CRTH2 antagonists, partial agonists, inverse agonists or partial inverse agonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type 2 cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet.* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention provides for a compound of formula (I):

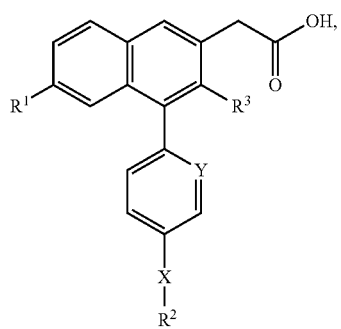

(I)

wherein:
X is —$SO_2$—, —$SO_2NH$—, —$NHSO_2$—, —NHC(O)— or —NHC(O)NH—;
Y is N or CH;
$R^1$ is halogen;
$R^2$ is -phenyl, unsubstituted or mono- or bi-substituted independently with lower alkyl, halogen, alkoxy, —$SO_2$-lower alkyl, haloalkyl or —$OCF_3$,
unsubstituted heteroaryl,
lower alkyl, unsubstituted or substituted with hydroxy, unsubstituted phenyl or phenyl substituted with halogen, —$SO_2$-lower alkyl or alkoxy,
unsubstituted cycloalkyl,
unsubstituted heterocycloalkyl, or
N(lower alkyl)$_2$, said lower alkyl independently being unsubstituted or substituted with unsubstituted phenyl or phenyl substituted with methoxy; and
$R^3$ is lower alkyl or hydrogen,
or a pharmaceutically acceptable salt thereof.

The invention also provides for pharmaceutical compositions comprising the compounds, methods of using the compounds and methods of preparing the compounds.

All documents cited to or relied upon below are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^3$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "alkoxy" denotes a group of the formula —O—R', wherein R' is an alkyl group. Examples of alkoxy moieties include methoxy, ethoxy, isopropoxy, and tert-butoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "haloalkoxy" means an alkoxy group wherein at least one of the hydrogen atoms of the alkoxy group has been replaced by same or different halogen atoms, particularly fluoro atoms. An example of a haloalkoxy group is trifluoromethoxy.

"Cycloalkyl" means a monovalent saturated carbocyclic moiety having mono- or bicyclic rings. The cycloalkyl moiety can optionally be substituted with one or more substituents. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-azabicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound If not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

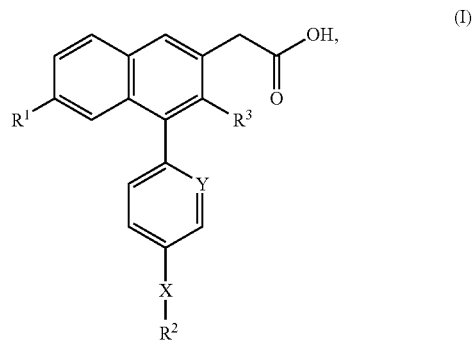

wherein:
$X$ is —$SO_2$—, —$SO_2NH$—, —$NHSO_2$—, —$NHC(O)$— or —$NHC(O)NH$—;
$Y$ is N or CH;
$R^1$ is halogen;
$R^2$ is -phenyl, unsubstituted or mono- or bi-substituted independently with lower alkyl, halogen, alkoxy, —$SO_2$-lower alkyl, haloalkyl or —$OCF_3$,
  unsubstituted heteroaryl,
  lower alkyl, unsubstituted or substituted with hydroxy, unsubstituted phenyl or phenyl substituted with halogen, —$SO_2$-lower alkyl or alkoxy,
  unsubstituted cycloalkyl,
  unsubstituted heterocycloalkyl, or
  N(lower alkyl)$_2$, said lower alkyl independently being unsubstituted or substituted with unsubstituted phenyl or phenyl substituted with methoxy; and
$R^3$ is lower alkyl or hydrogen,
or a pharmaceutically acceptable salt thereof.

In another embodiment, the invention provides for a compound according to formula (I), wherein X is —$SO_2$— or —$SO_2NH$—.

In another embodiment, the invention provides for a compound according to formula (I), wherein X is —$NHSO_2$—, —$NHC(O)$— or —$NHC(O)NH$—.

In another embodiment, the invention provides for a compound according to formula (I), wherein X is —$SO_2$—.

In another embodiment, the invention provides for a compound according to formula (I), wherein Y is CH.

In another embodiment, the invention provides for a compound according to formula (I), wherein $R^1$ is F or Cl.

In another embodiment, the invention provides for a compound according to formula (I), wherein $R^1$ is F.

In another embodiment, the invention provides for a compound according to formula (I), wherein $R^2$ is:
  phenyl, unsubstituted or mono- or bi-substituted independently with lower alkyl, halogen, alkoxy, —$SO_2$-lower alkyl, haloalkyl or —$OCF_3$,
  unsubstituted heteroaryl,
  unsubstituted cycloalkyl, or
  unsubstituted heterocycloalkyl.

In another embodiment, the invention provides for a compound according to formula (I), wherein $R^2$ is:
  lower alkyl, unsubstituted or substituted with hydroxy, unsubstituted phenyl or phenyl substituted with halogen, —$SO_2$-lower alkyl or alkoxy, or N(lower alkyl)$_2$, said lower alkyl independently being unsubstituted or substituted with unsubstituted phenyl or phenyl substituted with methoxy.

In another embodiment, the invention provides for a compound according to formula (I), wherein R$^2$ is phenyl, unsubstituted or mono- or bi-substituted independently with lower alkyl, halogen, alkoxy, —SO$_2$-lower alkyl, haloalkyl or —OCF$_3$.

In another embodiment, the invention provides for a compound according to formula (I), wherein R$^3$ is methyl.

In another embodiment, the invention provides for a compound according to formula (I), wherein X is —SO$_2$—; Y is C; and R$^2$ is phenyl, unsubstituted or mono- or bi-substituted independently with lower alkyl, halogen, alkoxy, —SO$_2$-lower alkyl, haloalkyl or —OCF$_3$.

In another embodiment, the invention provides for a compound according to formula (I), wherein R$^2$ is phenyl, unsubstituted or mono- or bi-substituted independently with methyl, chlorine, fluorine, —CF$_3$, —OCF$_3$ or —OCH$_3$.

In another embodiment, the invention provides for a compound according to formula (I), wherein R$^2$ is pyrrolidinyl, piperidinyl, —N(CH$_2$CH$_3$)$_2$, cyclohexyl, isopropyl, methyl, morpholinyl or hydroxyethyl.

In another embodiment, the invention provides for a compound according to formula (I), wherein the compound is:

{6-Fluoro-3-methyl-4-[4-(toluene-2-sulfonyl)-phenyl]-naphthalen-2-yl}-acetic acid;
{4-[4-(2-Chloro-benzenesulfonyl)-phenyl]-6-fluoro-3-methyl-naphthalen-2-yl}-acetic acid;
{4-[4-(3-Chloro-benzenesulfonyl)-phenyl]-6-fluoro-3-methyl-naphthalen-2-yl}-acetic acid;
{4-[4-(4-Chloro-benzenesulfonyl)-phenyl]-6-fluoro-3-methyl-naphthalen-2-yl}-acetic acid;
{6-Fluoro-3-methyl-4-[4-(2-trifluoromethyl-benzenesulfonyl)-phenyl]-naphthalen-2-yl}-acetic acid;
{6-Fsluoro-3-methyl-4-[4-(2-trifluoromethoxy-benzenesulfonyl)-phenyl]-naphthalen-2-yl}-acetic acid;
{6-Fluoro-3-methyl-4-[4-(4-trifluoromethoxy-benzenesulfonyl)-phenyl]-naphthalen-2-yl}-acetic acid;
{4-[4-(2,4-Dichloro-benzenesulfonyl)-phenyl]-6-fluoro-3-methyl-naphthalen-2-yl}-acetic acid;
{4-[4-(2,5-Dichloro-benzenesulfonyl)-phenyl]-6-fluoro-3-methyl-naphthalen-2-yl}-acetic acid;
{4-[4-(2,4-Difluoro-benzenesulfonyl)-phenyl]-6-fluoro-3-methyl-naphthalen-2-yl}-acetic acid;
{4-[4-(2,6-Difluoro-benzenesulfonyl)-phenyl]-6-fluoro-3-methyl-naphthalen-2-yl}-acetic acid;
{4-[4-(3,5-Bis-trifluoromethyl-benzenesulfonyl)-phenyl]-6-fluoro-3-methyl-naphthalen-2-yl}-acetic acid;
{4-[4-(3,5-Dichloro-benzenesulfonyl)-phenyl]-6-fluoro-3-methyl-naphthalen-2-yl}-acetic acid;
{4-[4-(3,5-Difluoro-benzenesulfonyl)-phenyl]-6-fluoro-3-methyl-naphthalen-2-yl}-acetic acid;
{6-Chloro-4-[4-(2-chloro-benzenesulfonyl)-phenyl]-3-methyl-naphthalen-2-yl}-acetic acid;
{6-Chloro-4-[4-(3-chloro-benzenesulfonyl)-phenyl]-3-methyl-naphthalen-2-yl}-acetic acid;
{6-Chloro-4-[4-(4-chloro-benzenesulfonyl)-phenyl]-3-methyl-naphthalen-2-yl}-acetic acid;
{6-Chloro-3-methyl-4-[4-(2-trifluoromethyl-benzenesulfonyl)-phenyl]-naphthalen-2-yl}-acetic acid;
{6-Chloro-3-methyl-4-[4-(2-trifluoromethoxy-benzenesulfonyl)-phenyl]-naphthalen-2-yl}-acetic acid;
{6-Chloro-3-methyl-4-[4-(4-trifluoromethoxy-benzenesulfonyl)-phenyl]-naphthalen-2-yl}-acetic acid;
{6-Chloro-4-[4-(2,4-dichloro-benzenesulfonyl)-phenyl]-3-methyl-naphthalen-2-yl}-acetic acid;
{6-Chloro-4-[4-(2,5-dichloro-benzenesulfonyl)-phenyl]-3-methyl-naphthalen-2-yl}-acetic acid;
{6-Chloro-4-[4-(2,4-difluoro-benzenesulfonyl)-phenyl]-3-methyl-naphthalen-2-yl}-acetic acid;
{6-Chloro-4-[4-(2,6-difluoro-benzenesulfonyl)-phenyl]-3-methyl-naphthalen-2-yl}-acetic acid;
{4-[4-(3,5-Bis-trifluoromethyl-benzenesulfonyl)-phenyl]-6-chloro-3-methyl-naphthalen-2-yl}-acetic acid;
{6-Chloro-4-[4-(3,5-dichloro-benzenesulfonyl)-phenyl]-3-methyl-naphthalen-2-yl}-acetic acid;
{6-Chloro-4-[4-(3,5-difluoro-benzenesulfonyl)-phenyl]-3-methyl-naphthalen-2-yl}-acetic acid;
{6-Chloro-4-[4-(4-fluoro-phenylsulfamoyl)-phenyl]-3-methyl-naphthalen-2-yl}-acetic acid;
[6-Chloro-3-methyl-4-(4-p-tolylsulfamoyl-phenyl)-naphthalen-2-yl]-acetic acid;
{6-Chloro-3-methyl-4-[4-(4-trifluoromethoxy-phenylsulfamoyl)-phenyl]-naphthalen-2-yl}-acetic acid;
{6-Chloro-4-[4-(3-chloro-2-methyl-phenylsulfamoyl)-phenyl]-3-methyl-naphthalen-2-yl}-acetic acid;
{6-Chloro-4-[4-(3-chloro-phenylsulfamoyl)-phenyl]-3-methyl-naphthalen-2-yl}-acetic acid;
{6-Chloro-3-methyl-4-[4-(pyrrolidine-1-sulfonyl)-phenyl]-naphthalen-2-yl}-acetic acid;
{6-Chloro-3-methyl-4-[4-(piperidine-1-sulfonyl)-phenyl]-naphthalen-2-yl}-acetic acid;
[6-Chloro-4-(4-diethylsulfamoyl-phenyl)-3-methyl-naphthalen-2-yl]-acetic acid;
[6-Chloro-4-(4-cyclohexylsulfamoyl-phenyl)-3-methyl-naphthalen-2-yl]-acetic acid;
[6-Chloro-4-(4-isopropylsulfamoyl-phenyl)-3-methyl-naphthalen-2-yl]-acetic acid;
[4-(4-Benzylsulfamoyl-phenyl)-6-chloro-3-methyl-naphthalen-2-yl]-acetic acid;
{6-Chloro-4-[4-(4-methoxy-benzylsulfamoyl)-phenyl]-3-methyl-naphthalen-2-yl}-acetic acid;
(6-Chloro-4-{4-[isopropyl-(4-methoxy-benzyl)-sulfamoyl]-phenyl}-3-methyl-naphthalen-2-yl)-acetic acid;
{6-Fluoro-4-[4-(4-fluoro-phenylsulfamoyl)-phenyl]-3-methyl-naphthalen-2-yl}-acetic acid;
[6-Fluoro-3-methyl-4-(4-p-tolylsulfamoyl-phenyl)-naphthalen-2-yl]-acetic acid;
{6-Fluoro-3-methyl-4-[4-(4-trifluoromethoxy-phenylsulfamoyl)-phenyl]-naphthalen-2-yl}-acetic acid;
{4-[4-(3-Chloro-2-methyl-phenylsulfamoyl)-phenyl]-6-fluoro-3-methyl-naphthalen-2-yl}-acetic acid;
{4-[4-(3-Chloro-phenylsulfamoyl)-phenyl]-6-fluoro-3-methyl-naphthalen-2-yl}-acetic acid;
{6-Fluoro-3-methyl-4-[4-(pyrrolidine-1-sulfonyl)-phenyl]-naphthalen-2-yl}-acetic acid;
{6-Fluoro-3-methyl-4-[4-(piperidine-1-sulfonyl)-phenyl]-naphthalen-2-yl}-acetic acid;
[4-(4-Diethylsulfamoyl-phenyl)-6-fluoro-3-methyl-naphthalen-2-yl]-acetic acid;
[4-(4-Cyclohexylsulfamoyl-phenyl)-6-fluoro-3-methyl-naphthalen-2-yl]-acetic acid;
[6-Fluoro-4-(4-isopropylsulfamoyl-phenyl)-3-methyl-naphthalen-2-yl]-acetic acid;
[4-(4-Benzylsulfamoyl-phenyl)-6-fluoro-3-methyl-naphthalen-2-yl]-acetic acid;
{6-Fluoro-4-[4-(4-methoxy-benzylsulfamoyl)-phenyl]-3-methyl-naphthalen-2-yl}-acetic acid;
(6-Fluoro-4-{4-[isopropyl-(4-methoxy-benzyl)-sulfamoyl]-phenyl}-3-methyl-naphthalen-2-yl)-acetic acid;
[6-Fluoro-4-(4-methanesulfonyl-phenyl)-3-methyl-naphthalen-2-yl]-acetic acid;
{6-Chloro-3-methyl-4-[4-(morpholine-4-sulfonyl)-phenyl]-naphthalen-2-yl}-acetic acid;
{6-Chloro-4-[4-(2-hydroxy-ethylsulfamoyl)-phenyl]-3-methyl-naphthalen-2-yl}-acetic acid;
{6-Fluoro-4-[4-(2-hydroxy-ethylsulfamoyl)-phenyl]-3-methyl-naphthalen-2-yl}-acetic acid;

[6-Fluoro-4-(5-methanesulfonyl-pyridin-2-yl)-3-methyl-naphthalen-2-yl]-acetic acid;
[4-(4-Benzenesulfonylamino-phenyl)-6-fluoro-3-methyl-naphthalen-2-yl]-acetic acid;
{4-[4-(3,5-Bis-trifluoromethyl-benzenesulfonylamino)-phenyl]-6-fluoro-3-methyl-naphthalen-2-yl}-acetic acid;
[4-(4-Benzenesulfonylamino-phenyl)-6-chloro-3-methyl-naphthalen-2-yl]-acetic acid;
{6-Chloro-3-methyl-4-[4-(2-trifluoromethyl-benzenesulfonylamino)-phenyl]-naphthalen-2-yl}-acetic acid;
{6-Chloro-3-methyl-4-[4-(toluene-2-sulfonylamino)-phenyl]-naphthalen-2-yl}-acetic acid;
[4-(4-Acetylamino-phenyl)-6-chloro-3-methyl-naphthalen-2-yl]-acetic acid;
[4-(4-Benzoylamino-phenyl)-6-chloro-3-methyl-naphthalen-2-yl]-acetic acid; or
{6-Chloro-3-methyl-4-[4-(3-phenyl-ureido)-phenyl]-naphthalen-2-yl}-acetic acid.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

In another embodiment, the invention provides for the use of a compound according to formula (I) for the preparation of a medicament for the treatment or prophylaxis of a respiratory disorder.

In another embodiment, the invention provides for a compound according to formula (I) for the treatment or prophylaxis of a respiratory disorder.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

In another embodiment, provided is an invention as hereinbefore described.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme 1

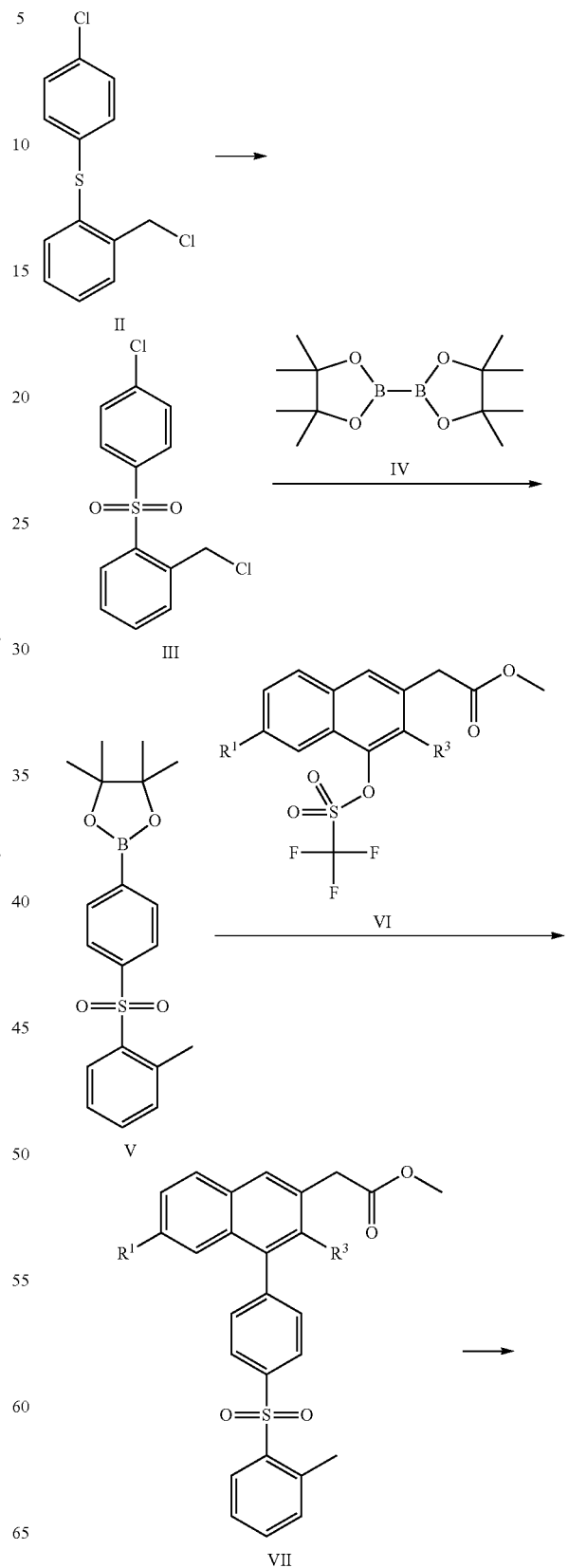

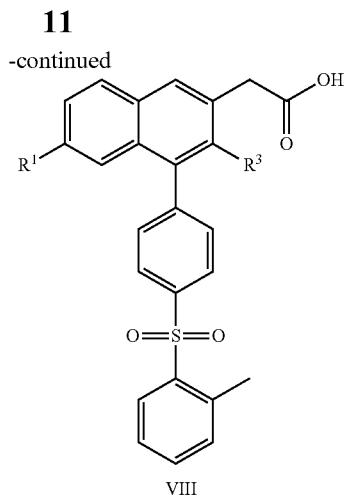

VIII

The compounds of the invention of formula VIII may be prepared according to Scheme 1. Starting with biarylsulfide II, an oxidation reaction can provide sulfone intermediate III. Reaction of III with bis(pinacoloto)diboron IV can generate the substituted phenylboronic acid V. Cross-coupling between V and the triflate intermediates VI can give the biaryl intermediates VII. Finally, hydrolysis of the methyl ester groups in VII can furnish the compounds of the invention of formula VIII.

The oxidation reaction of II to provide the sulfone intermediate III may be carried out in the presence of an excess of an oxidant such as m-chloroperoxybenzoic acid (mcpba) in an inert solvent such as methylene chloride. The reactions may be performed at temperatures between 10° C. and room temperature for several hours.

The conversion of intermediate III to the boronate ester V may be carried out in the presence of bis(pinacolato)diboron IV, potassium carbonate, and a palladium catalyst such as tetrakis(triphenylphosphine)palladium(0). The reaction may be carried out in an inert solvent such as dioxane at a temperature between 90° C. and 110° C. for a reaction time of approximately 60 hours.

The cross-coupling reactions between V and the triflate intermediate VI to give the biaryl intermediates VII may be carried out in the presence of palladium(II) acetate and a phosphine ligand such as 2-dicyclohexylphosphino-2',6'-dimethoxybiphenyl (S-Phos). The reaction may be carried out in the presence of a base such as potassium phosphate in a mixture of toluene and water at 125° C. for several hours.

Hydrolysis of ester compounds VII to give the compounds of the invention VIII can be accomplished in the presence of a base such as lithium hydroxide, in an inert solvent such as tetrahydrofuran, water, or mixtures thereof, at a temperature between room temperature and the reflux temperature for several hours.

Scheme 2

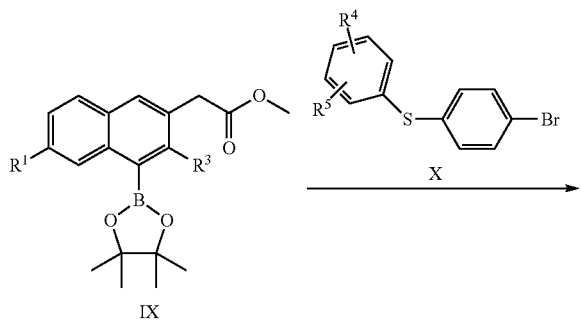

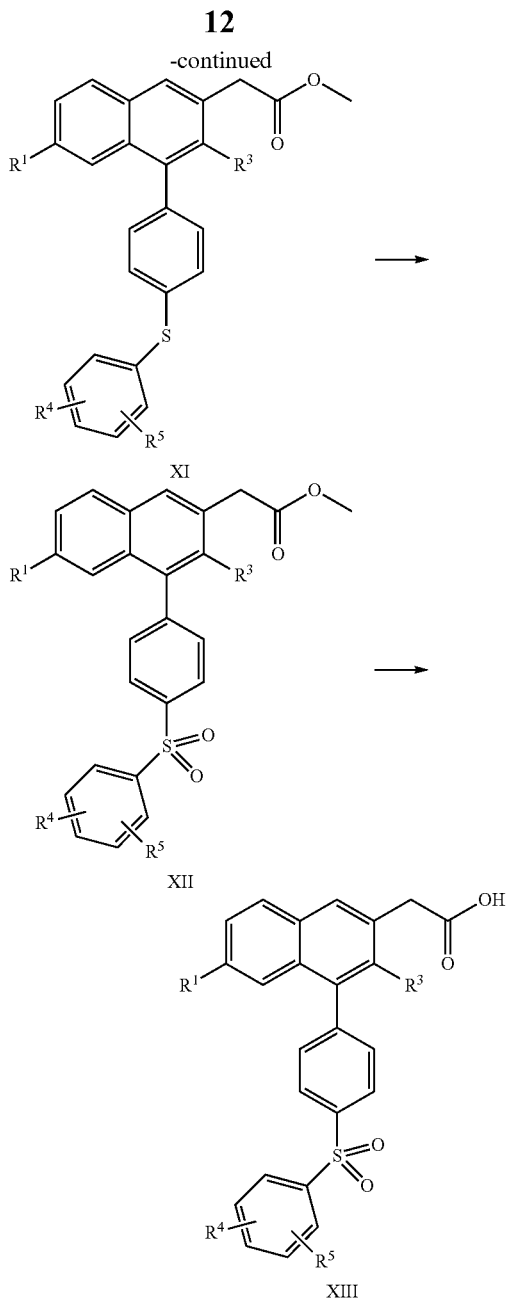

The compounds of the invention of formula XIII may be prepared according to Scheme 2. Starting with boronate esters IX, a cross coupling reaction with aryl bromides X affords the biaryl compounds XI. Oxidation provides the sulfones XII. Hydrolysis of the methyl ester group in XII affords the compounds of the invention of formula XIII.

The cross-coupling reactions between boronates IXX and aryl bromides X may be carried out in the presence of a palladium catalyst such as tetrakis(triphenylphosphine)-palladium(0) and an aqueous solution of a base such as sodium carbonate or sodium bicarbonate. The reactions may be carried out in a convenient solvent such as dimethoxyethane under reflux conditions for several hours.

The oxidation reactions of XI to provide the sulfone intermediates XII can be carried out in the presence of an excess of an oxidant such as m-chloroperoxybenzoic acid (mcpba) in an inert solvent such as methylene chloride. The reactions may be performed at room temperature for several hours.

Hydrolysis of ester compounds XII to give the compounds of the invention XIII can be accomplished in the presence of a base such as lithium hydroxide, in an inert solvent such as tetrahydrofuran, water, or mixtures thereof, at a temperature between room temperature and the reflux temperature for several hours.

Scheme 3

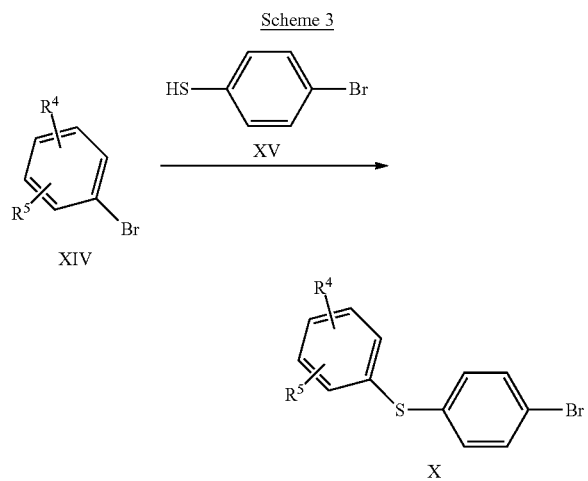

The aryl bromide intermediates X may be prepared from the substituted aryl bromides XIV and 4-bromo-thiophenol XV according to Scheme 3. This transformation may be carried out in the presence of a copper catalyst such as CuCl, an additive such as tetramethyl heptanedione, and a base such as cesium carbonate. The reaction may be carried out at elevated temperatures between 100° C. and 130° C. for several hours (Aicher, T. D. et. al. WO2006057860 A1 2006).

The compounds of the invention of formula XVIII may be prepared according to Scheme 4. Starting with boronates IX, a cross coupling reaction with aryl bromides XVI affords the biaryl compounds XVII. Hydrolysis of the methyl ester group in XVII affords the compounds of the invention of formula XVIII.

Scheme 4

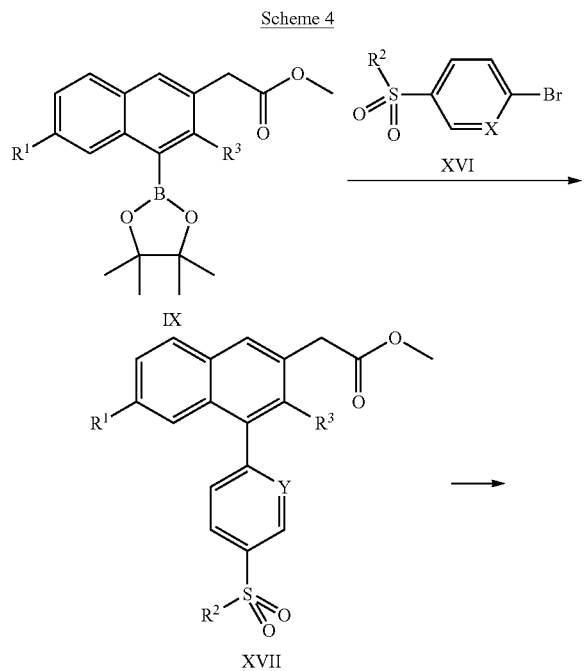

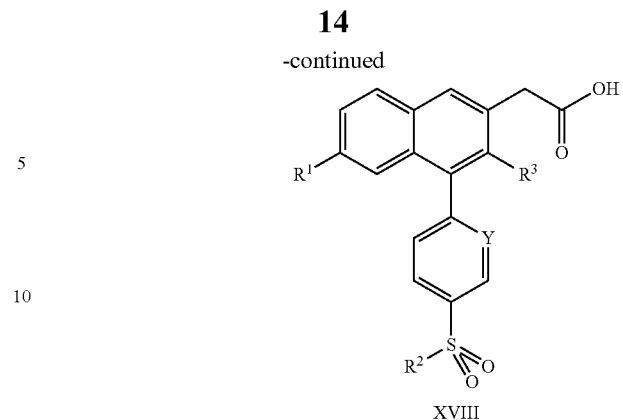

The cross-coupling reaction between boronate esters IX and aryl bromides XVI to provide the biaryl intermediates XVII may be carried out in the presence of a palladium catalyst such as tetrakis(triphenylphosphine)-palladium (0) or [1,1'-bis(diphenylphosphino)-ferrocene]dichloropalladium(II) and a base such as sodium carbonate. The reactions may be carried out in a convenient solvent such as dimethoxyethane, toluene, tetrahydrofuran (THF), or mixtures thereof, under reflux conditions for two hours to sixteen hours.

Hydrolysis of ester compounds XVII to give the compounds of the invention XVIII can be accomplished in the presence of a base such as lithium hydroxide, in an inert solvent such as tetrahydrofuran, water, or mixtures thereof, at a temperature between room temperature and the reflux temperature for several hours.

Scheme 5

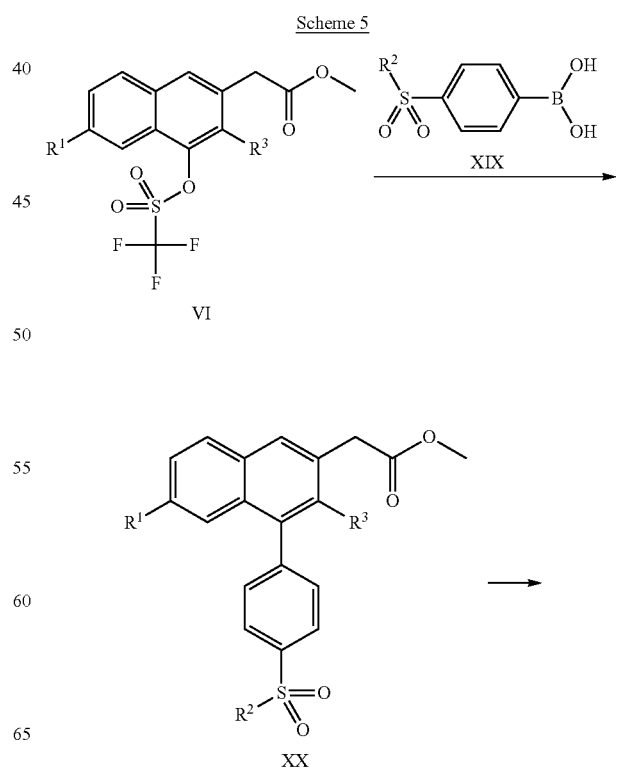

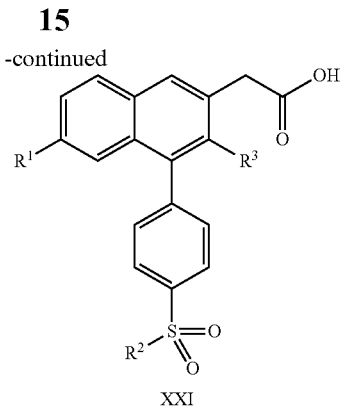

XXI

Compounds of the invention of formula XXI can be prepared according to scheme 5. Starting with triflates VI, a cross coupling reaction with boronic acids XIX generates the biaryl intermediates XX. Hydrolysis of the ester group in XX provides the compounds of the invention of formula XXI.

The cross-coupling reactions between triflates VI and aryl boronic acids XIX to provide the biaryl intermediates XX may be carried out in the presence of a palladium catalyst such as 1,1'-bis(diphenylphosphino)ferrocenedichloropalladium (II) or a mixture of palladium (II) acetate and a phosphine ligand such as triphenylphosphine. The reactions may be performed in the presence of a base such as cesium carbonate or sodium carbonate. The reactions may be carried out in a convenient solvent such as dimethoxyethane or N,N-dimethylformamide, and water may be added as a co-solvent. The reactions can proceed under reflux conditions for reaction times between two hours and 15 hours.

Hydrolysis of ester compounds XX to give the compounds of the invention XXI can be accomplished in the presence of a base such as lithium hydroxide, in an inert solvent such as tetrahydrofuran, water, or mixtures thereof, at a temperature between room temperature and the reflux temperature for several hours.

Scheme 6

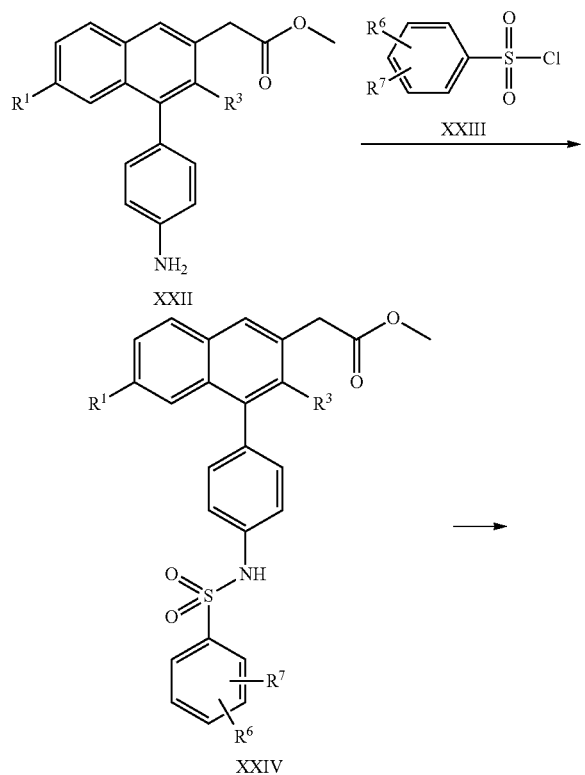

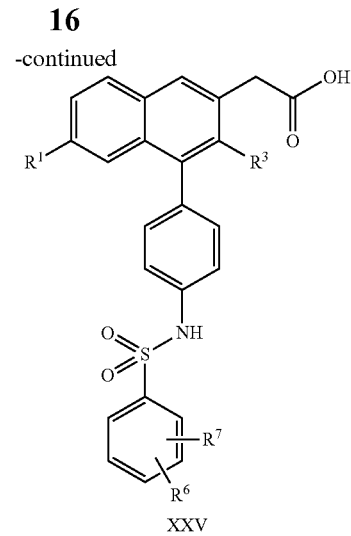

XXV

The compounds of the invention of formula XXV can be prepared as described above in Scheme 6. Starting from intermediates of formula XXII, sulfonylation with sulfonyl chlorides XXIII can furnish sulfonamides XXIV. Hydrolysis of the methyl ester group in XXIV provides the compounds of the invention of formula XXV.

The sulfonylation of XXII with sulfonyl chlorides XXIII to give compounds XXIV may be carried out in the presence of a base such as N,N-diisopropylethylamine and an inert solvent such as tetrahydrofuran. The reactions may be carried out at temperatures between 0° C. and room temperature for several hours.

Hydrolysis of ester compounds XXIV to give the compounds of the invention XXV can be accomplished in the presence of a base such as lithium hydroxide or sodium hydroxide in a solvent such as tetrahydrofuran, methanol, ethanol, water, or mixtures thereof, at a temperature between room temperature and the reflux temperature for several hours.

Scheme 7

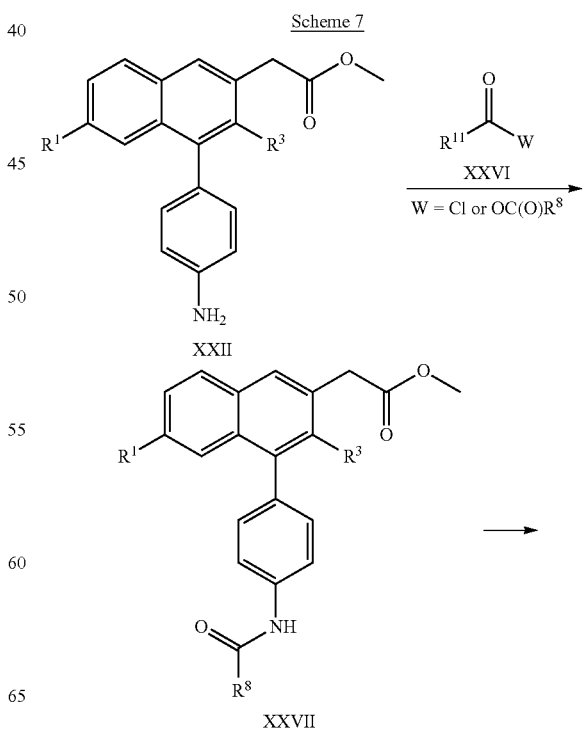

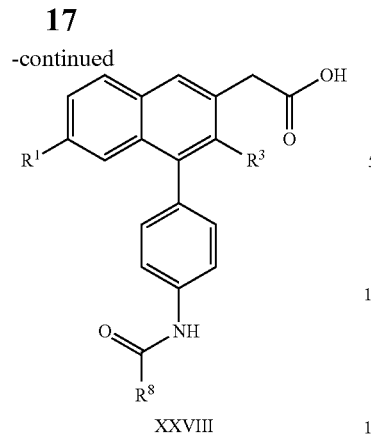

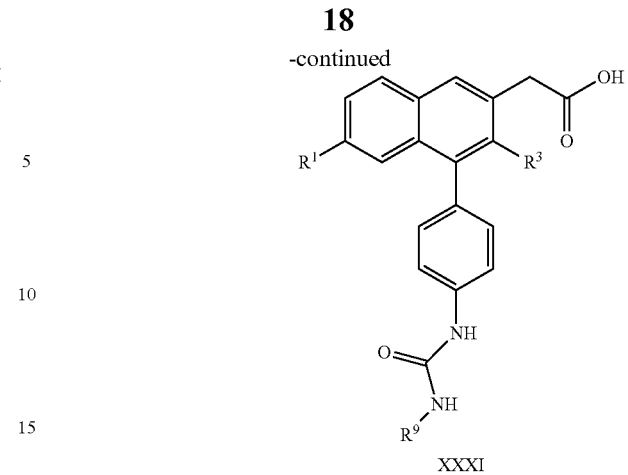

The compounds of the invention of formula XXVIII can be prepared as described above in Scheme 7. Starting from intermediates of formula XXII, acylation with an appropriate acid chloride or acid anhydride (XXVI) can give amides of type XXVII. Hydrolysis of the methyl ester group in XXVII provides the compounds of the invention of formula XXVIII.

The acylation of intermediate XXII can be carried out in the presence of a suitable acid chloride or acid anhydride and a base such as pyridine or N,N-diisopropylethylamine. The reactions may be performed neat or in the presence of an inert solvent such as methylene chloride at room temperature for reaction times between 10 minutes and several hours.

Hydrolysis of ester compounds XXVII to give the compounds of the invention XXVIII can be accomplished in the presence of a base such as lithium hydroxide or sodium hydroxide in a solvent such as tetrahydrofuran, methanol, ethanol, water, or mixtures thereof, at a temperature between room temperature and the reflux temperature for several hours.

The compounds of the invention of formula XXXI can be prepared as described above in Scheme 8. Starting from intermediates of formula XXII, reaction with isocyanates XXIX can generate the urea compounds XXX. Hydrolysis of the methyl ester group in XXX provides the compounds of the invention of formula XXXI.

The reaction of intermediates XXII with isocyanates XXIX can be accomplished in the presence of a solvent such as ethanol at room temperature for several hours.

Hydrolysis of ester compounds XXX to give the compounds of the invention XXXI can be accomplished in the presence of a base such as lithium hydroxide or sodium hydroxide in a solvent such as tetrahydrofuran, methanol, ethanol, water, or mixtures thereof, at a temperature between room temperature and the reflux temperature for several hours.

The naphthalene triflate intermediate VI can be prepared according to Scheme 9.

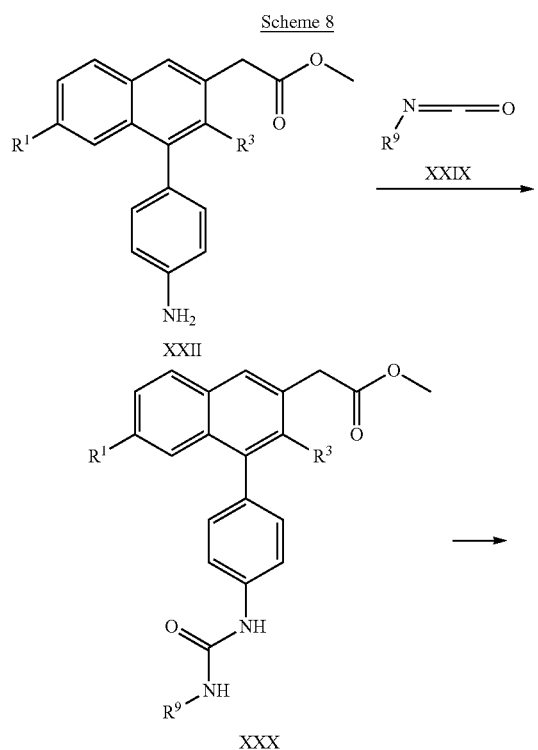

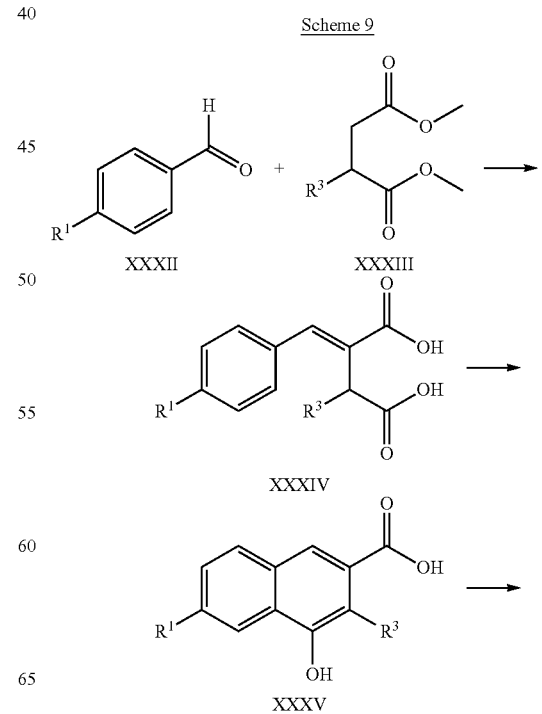

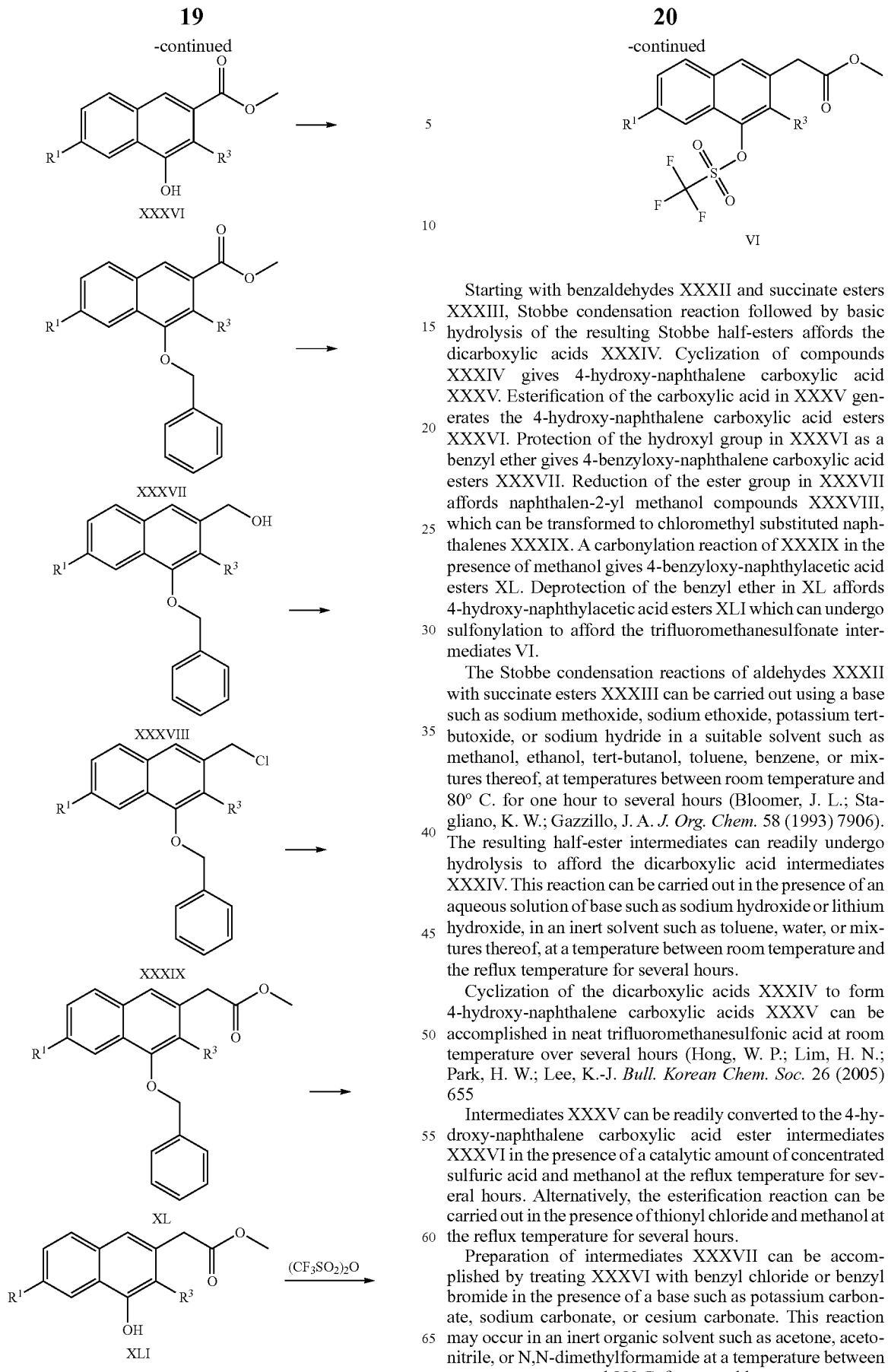

Starting with benzaldehydes XXXII and succinate esters XXXIII, Stobbe condensation reaction followed by basic hydrolysis of the resulting Stobbe half-esters affords the dicarboxylic acids XXXIV. Cyclization of compounds XXXIV gives 4-hydroxy-naphthalene carboxylic acid XXXV. Esterification of the carboxylic acid in XXXV generates the 4-hydroxy-naphthalene carboxylic acid esters XXXVI. Protection of the hydroxyl group in XXXVI as a benzyl ether gives 4-benzyloxy-naphthalene carboxylic acid esters XXXVII. Reduction of the ester group in XXXVII affords naphthalen-2-yl methanol compounds XXXVIII, which can be transformed to chloromethyl substituted naphthalenes XXXIX. A carbonylation reaction of XXXIX in the presence of methanol gives 4-benzyloxy-naphthylacetic acid esters XL. Deprotection of the benzyl ether in XL affords 4-hydroxy-naphthylacetic acid esters XLI which can undergo sulfonylation to afford the trifluoromethanesulfonate intermediates VI.

The Stobbe condensation reactions of aldehydes XXXII with succinate esters XXXIII can be carried out using a base such as sodium methoxide, sodium ethoxide, potassium tert-butoxide, or sodium hydride in a suitable solvent such as methanol, ethanol, tert-butanol, toluene, benzene, or mixtures thereof, at temperatures between room temperature and 80° C. for one hour to several hours (Bloomer, J. L.; Stagliano, K. W.; Gazzillo, J. A. *J. Org. Chem.* 58 (1993) 7906). The resulting half-ester intermediates can readily undergo hydrolysis to afford the dicarboxylic acid intermediates XXXIV. This reaction can be carried out in the presence of an aqueous solution of base such as sodium hydroxide or lithium hydroxide, in an inert solvent such as toluene, water, or mixtures thereof, at a temperature between room temperature and the reflux temperature for several hours.

Cyclization of the dicarboxylic acids XXXIV to form 4-hydroxy-naphthalene carboxylic acids XXXV can be accomplished in neat trifluoromethanesulfonic acid at room temperature over several hours (Hong, W. P.; Lim, H. N.; Park, H. W.; Lee, K.-J. *Bull. Korean Chem. Soc.* 26 (2005) 655

Intermediates XXXV can be readily converted to the 4-hydroxy-naphthalene carboxylic acid ester intermediates XXXVI in the presence of a catalytic amount of concentrated sulfuric acid and methanol at the reflux temperature for several hours. Alternatively, the esterification reaction can be carried out in the presence of thionyl chloride and methanol at the reflux temperature for several hours.

Preparation of intermediates XXXVII can be accomplished by treating XXXVI with benzyl chloride or benzyl bromide in the presence of a base such as potassium carbonate, sodium carbonate, or cesium carbonate. This reaction may occur in an inert organic solvent such as acetone, acetonitrile, or N,N-dimethylformamide at a temperature between room temperature and 80° C. for several hours.

Reduction of the ester group in XXXVII with lithium aluminum hydride gives the naphthalen-2-yl methanol compounds XXXVIII. This reaction can be carried out in an inert organic solvent such as tetrahydrofuran, diethyl ether, toluene, or mixtures thereof, at a temperature between 0° C. and 80° C. for several hours.

The chloromethyl naphthalene intermediates XXXIX can be prepared by the reaction of compounds XXXVIII with carbon tetrachloride and triphenylphosphine in an inert organic solvent such as toluene, acetonitrile, dichloromethane, N,N-dimethylformamide, or tetrahydrofuran at a temperature between 0° C. and 120° C. (or the reflux temperature) for several hours.

Conversion of chlorides XXXIX to the naphthylacetic acid esters XL can be accomplished by a palladium catalyzed carbonylation reaction under one atmosphere of carbon monoxide in the presence of a base such as potassium carbonate in methanol and optionally in the presence of a co-solvent such as tetrahydrofuran. This transformation can be carried out using a palladium catalyst such as bis(triphenylphosphine)dichloropalladium(II) at a temperature between room temperature and 90° C. for 10 minutes to several hours (Schoenberg, A.; Bartoletti, I.; Heck, R. F. *J. Org. Chem.* 39 (1974) 3318).

Removal of the benzyl protecting group in XL through catalytic hydrogenolysis affords the 4-hydroxy-naphthylacetic acid esters XLI. This reaction can be carried out under one atmosphere of hydrogen in the presence of a catalyst such as 10% palladium on carbon or 20% palladium hydroxide on carbon in a solvent such as methanol or ethanol at room temperature for several hours. Alternatively, the benzyl ether can be removed in the presence of boron trifluoride diethyl etherate. This reaction can be performed in acetonitrile using sodium iodide as an additive at temperatures between 0° C. to room temperature for reaction times between one hour to several hours (Vankar, Y. D.; Rao, T. *J. Chem. Research (S)* (1985) 232).

Compounds XLI can be converted to the trifluoromethanesulfonate esters VI through a reaction with trifluoromethanesulfonic anhydride in the presence of an amine base such as pyridine, triethylamine, or diisopropylethylamine and optionally in the presence of an inert solvent such as dichloromethane for several hours at temperatures between 0° C. and room temperature.

Scheme 10

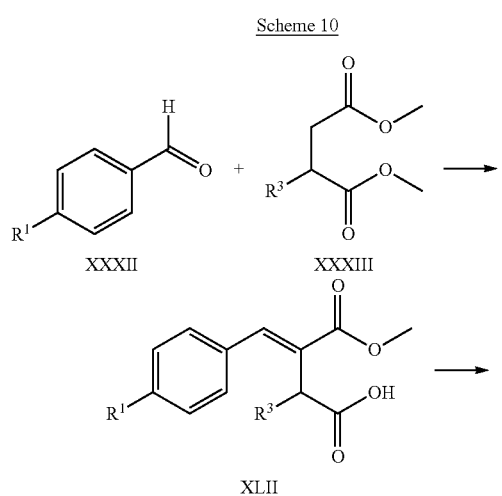

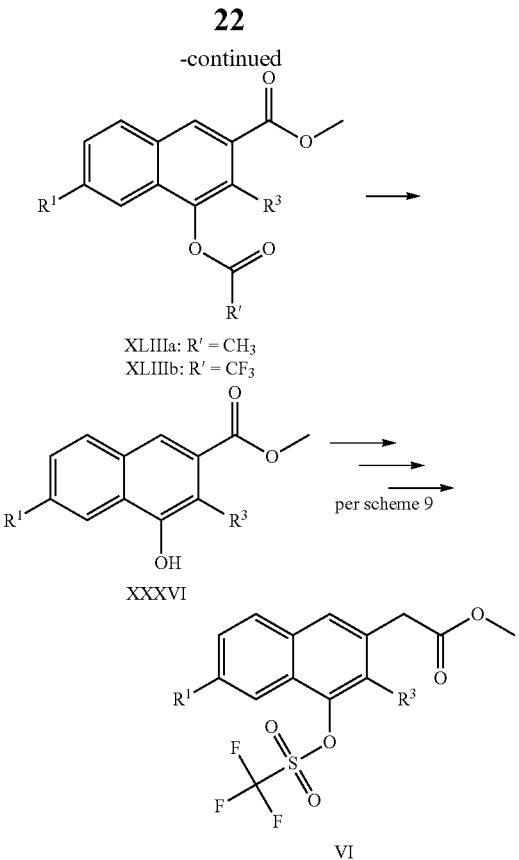

Alternatively, the triflate intermediates VI can be synthesized as described above in Scheme 10. Starting with benzaldehydes XXXII and succinate esters XXXIII, a Stobbe condensation reaction affords 3-carboalkoxy-4-phenyl-3-butenoic acids XLII. Benzannulation of compounds XLII gives 4-acetoxy-naphthalene carboxylic acid esters XLIIIa, or, alternatively, 4-trifluoroacetoxy-naphthalene carboxylic acid esters XLIIIb. Hydrolysis of the acetate ester in compounds XLIIIa or removal of the trifluoroacetate ester in XLIIIb generates the 4-hydroxy-naphthalene carboxylic acid esters XXXVI. Conversion of intermediate XXXVI to the trifluoromethanesulfonate intermediates VI can be carried out as described in Scheme 9.

Stobbe condensation reactions of XXXII with succinate esters XXXIII to give intermediates XLII can be carried out using a base such as sodium methoxide, sodium ethoxide, potassium tert-butoxide, or sodium hydride in a suitable solvent such as methanol, ethanol, tert-butanol, toluene, benzene, or mixtures thereof, at temperatures between room temperature and 80° C. for one hour to several hours (Bloomer, J. L.; Stagliano, K. W.; Gazzillo, J. A. *J. Org. Chem.* 58 (1993) 7906).

Cyclization of compounds XLII to produce 4-acetoxy-naphthalene carboxylic acid esters XLIIIa can be achieved in neat acetic anhydride using a base such as sodium acetate or potassium acetate at temperatures between 120° C. and 160° C. (or the reflux temperature) for several hours (El-Abbady, A. M.; El-Assal, L. S. *J. Chem. Soc.* (1959) 1024).

Selective hydrolysis of the acetate group in XLIIIa to give the 4-hydroxy-naphthalene carboxylic acid esters XXXVI can be accomplished in the presence of a base such as potassium carbonate, sodium carbonate, sodium bicarbonate, sodium methoxide or potassium tert-butoxide in a suitable solvent such as methanol, acetone, water, or mixtures thereof, at a temperature between 0° C. and 80° C. for several hours.

Alternatively, compounds XXXVI can be accessed through cyclization of compounds XLII in the presence of trifluoroacetic anhydride and triethylamine in an inert organic solvent such as tetrahydrofuran or dichloromethane at room temperature. The resulting 4-trifluoroacetoxy-naphthalene carboxylic acid esters XLIIIb can transformed into compounds XXXVI by a reaction with sodium borohydride in an alcohol solvent such as methanol at a temperature between 0° C. and room temperature (Fuganti, C.; Serra, S. *J. Chem. Research* (S) (1998) 638).

Conversion of intermediate XXXVI to the trifluoromethanesulfonate intermediates VI can be carried out as described in Scheme 9.

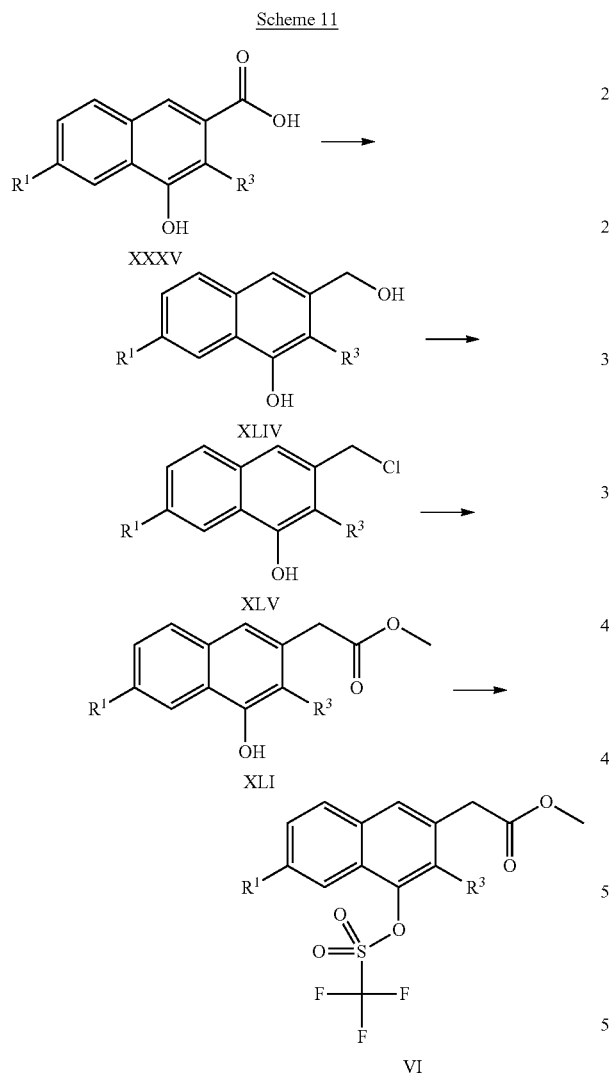

Alternatively, the naphthalene triflate intermediates VI can be prepared according to Scheme 11 above. Reduction of intermediate XXXV can provide the hydroxymethyl intermediates XLIV. A chlorination reaction to furnish compounds of type XLV can then be followed by a carbonylation reaction to afford intermediate XLI. A sulfonylation reaction of XLI affords the triflate intermediate VI.

Reduction of the carboxyl group in intermediates XXXV, which can be synthesized according to Scheme 9, can be accomplished in the presence of lithium aluminum hydride to afford the alcohols XLIV. This reaction can be carried out in an inert organic solvent such as tetrahydrofuran, diethyl ether, toluene or mixtures thereof, at a temperature between room temperature and 80° C. for several hours.

Transformation of alcohols XLIV into chlorides XLV can be accomplished using carbon tetrachloride in the presence of triphenylphosphine. This reaction can occur in an inert organic solvent such as tetrahydrofuran, acetonitrile, toluene, N,N-dimethylformamide, or dichloromethane, at a temperature between 0° C. and 120° C. for several hours.

Conversion of the chlorides XLV to the intermediates XLI can be accomplished by a palladium catalyzed carbonylation reaction under one atmosphere of carbon monoxide in the presence of a base such as potassium carbonate in methanol and optionally in the presence of a co-solvent such as tetrahydrofuran. This transformation can be carried out using a palladium catalyst such as bis(triphenylphosphine)dichloropalladium(II) at a temperature between room temperature and 90° C. for 10 minutes to several hours (Schoenberg, A.; Bartoletti, I.; Heck, R. F. *J. Org. Chem.* 39 (1974) 3318).

Compounds XLI can be converted to the trifluoromethanesulfonate esters VI through a reaction with trifluoromethanesulfonic anhydride in the presence of an amine base such as pyridine, triethylamine, or diisopropylethylamine and in the presence or absence of an inert solvent such as dichloromethane for several hours at temperatures between 0° C. and room temperature.

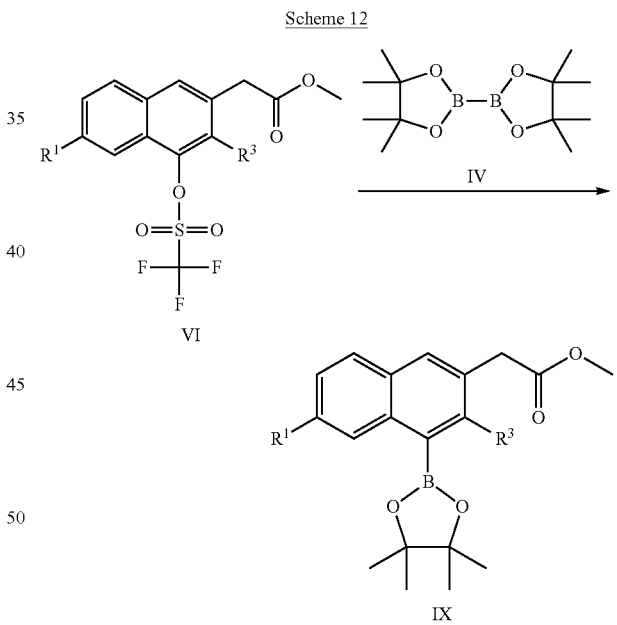

The boronate ester intermediates IX may be prepared according to Scheme 12. Starting with the trifluoromethanesulfonate intermediates VI described above in Schemes 9-11, a palladium catalyzed borylation reaction furnishes the boronate ester compounds IX. This reaction can be performed in the presence of bis(pinacolato)diboron IV, a base such as potassium acetate, a palladium catalyst such as dichloro 1,1'-bis(diphenylphosphino)ferrocene palladium(II), bis(triphenylphosphine)dichloro-palladium(II), or tetrakis(triphenylphosphine)palladium (0) and optionally in the presence of a phosphine ligand such as 1,1'-bis(diphenylphosphino)ferrocene. The reactions can be carried out in an anhydrous organic solvent such as 1,4-dioxane, N,N-dimethylformamide, or dimethyl sulfoxide at temperatures between 90° C. and 150° C. for reaction times between three hours and 24 hours (Ishiyama, T.; Murata, M.; Miyaura, N. *J. Org. Chem.* 60 (1995) 7508).

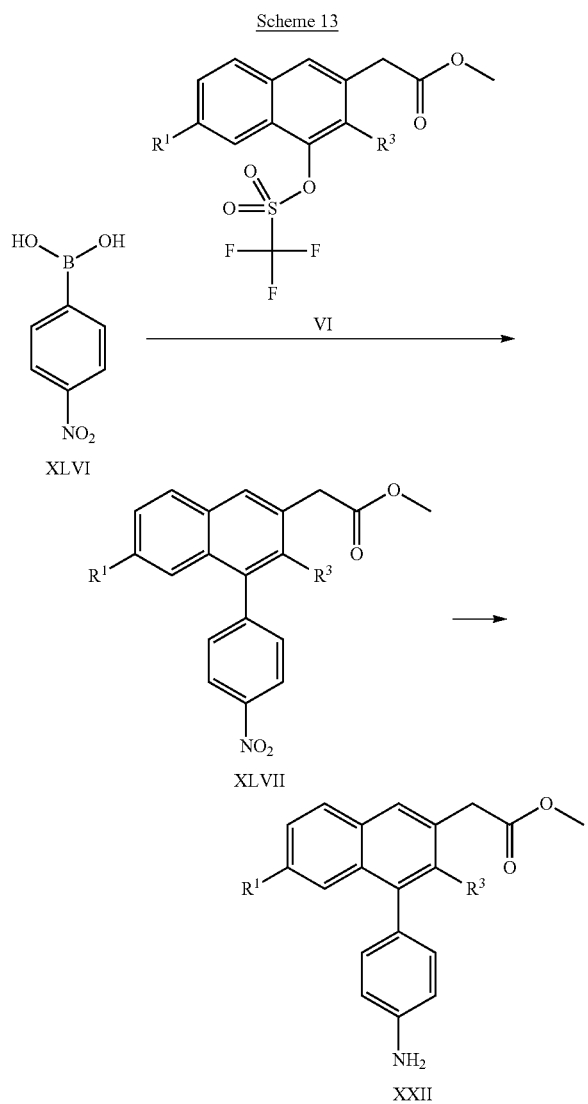

Scheme 13

Intermediate XXII may be prepared as described above in Scheme 13. Starting with 4-nitrophenyl boronic acid (XLVI) a cross coupling reaction with intermediates VI forms the biaryl intermediates XLVII. Reduction of the nitro group in XLVII can provide the amine intermediate XXII.

The cross-coupling reaction between XLVI and triflate VI to give XLVII may be carried out in the presence of a palladium catalyst such as [1,1'-bis(diphenylphosphino)-ferrocene]dichloropalladium(II) and a base such as cesium carbonate. The reaction can be performed in a solvent such as dimethoxyethane at 120° C. for reaction times up to 1 hour using a microwave reactor. Alternatively, the reaction may be carried out using conventional heating for longer reaction times.

The reduction of XLVII to give the amine intermediate XXII may be accomplished in the presence of zinc dust and ammonium chloride. The reaction may be carried out in a solvent such as methanol, tetrahydrofuran, water, or mixtures thereof, at room temperature for reaction times of approximately 10 minutes.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep $C_{18}$ column (5 μm, OBD™ 20×100 mm) from Waters Corporation, or a SunFire™ Prep $C_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex II FTICR with a 4.7 Tesla magnet (from Bruker Corporation), a Waters® Alliance® 2795-ZQ™ 2000 (from Waters Corporation), or an MDS Sciex™ API-2000™ n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.
Part I: Preparation of Starting Materials and Intermediates Preparation of (6-fluoro-3-methyl-4-trifluoromethanesulfonyloxy-naphthalen-2-yl)-acetic acid methyl ester 2-[1-(4-Fluoro-phenyl)-meth-(E)-ylidene]-3-methyl-succinic acid To a suspension of sodium hydride (60% in paraffin oil, 31 g, 775 mmol) in toluene (150 mL) was added a solution of 4-fluorobenzaldehyde (30 g, 242 mmol) and dimethyl methylsuccinate (58 g, 362 mmol) in toluene (150 mL) over 1 hour at 0° C. under nitrogen. The reaction was initiated by addition of a drop of methanol at room temperature and was stirred at room temperature for 2 hours. A 2.0 N aqueous NaOH solution (300 mL) was added slowly at 0° C. The resulting mixture was stirred at 110° C. for 4 hours. The mixture was then cooled to room temperature and the aqueous layer was diluted with water (300 mL) and washed with $Et_2O$ (2×300 mL). The aqueous phase was cooled in an ice-water bath. Addition of concentrated HCl was followed by extraction with ethyl acetate (2×100 mL). The combined organic extracts were washed with water (50 mL) followed by brine (50 mL). The organic phase was dried over anhydrous sodium sulfate and concentrated. The residue was crystallized from ethyl acetate-hexanes to give 2-[1-(4-fluoro-phenyl)-meth-(E)-ylidene]-3-methyl succinic acid. The procedure above was repeated using a separate amount of 4-fluorobenzaldehyde (30 g, 242 mmol). The products of the two reactions were combined to provide 2-[1-(4-fluoro-phenyl)-meth-(E)-ylidene]-3-methyl succinic acid as a pale yellow solid (28 g, 24% overall). MS calcd. for $C_{12}H_{12}FO_4$ [(M+H)$^+$] 239, obsd. 239.2.

6-Fluoro-4-hydroxy-3-methyl-naphthalene-2-carboxylic acid

A solution of 2-[1-(4-fluoro-phenyl)-meth-(E)-ylidene]-3-methyl succinic acid (28 g, 118 mmol) in trifluoromethanesulfonic acid (140 mL) was stirred at room temperature for 16 h. The resulting mixture was carefully poured into ice cooled water with continuous stirring to give a solid precipitate, which was filtered, washed with water and dried in vacuo to yield 6-fluoro-4-hydroxy-3-methyl-naphthalene-2-carboxylic acid (28 g, >100% crude) as yellow solid. This crude product was used in the next step without further purification. MS calcd. for $C_{12}H_8FO_3$ [(M−H)$^-$] 219, obsd. 218.9.

6-Fluoro-4-hydroxy-3-methyl-naphthalene-2-carboxylic acid methyl ester

To a 0° C. solution of crude 6-fluoro-4-hydroxy-3-methyl-naphthalene-2-carboxylic acid (28 g, approx. 118 mmol) in MeOH (240 mL) was added concentrated sulfuric acid (18.9 mL, 382 mmol) dropwise. The reaction mixture was then warmed to room temperature and refluxed overnight. After this time, the methanol was distilled off under reduced pressure, and the crude mixture was diluted with ethyl acetate. This solution was washed with saturated aqueous $NaHCO_3$. The organic phase was dried over $Na_2SO_4$, filtered and concentrated under reduced pressure to give the crude product. Silica gel column chromatography (6% ethyl acetate-hexane) afforded 6-fluoro-4-hydroxy-3-methyl-naphthalene-2-carboxylic acid methyl ester (14.8 g, 54%) as a light yellow solid. MS calcd. for $C_{13}H_{12}FO_3$ [(M+H)$^+$] 235, obsd. 235.2.

4-Benzyloxy-6-fluoro-3-methyl-naphthalene-2-carboxylic acid methyl ester

To a solution of 6-fluoro-4-hydroxy-3-methyl-naphthalene-2-carboxylic acid methyl ester (21.7 g, 92.7 mmol) in dry DMF (250 mL) was added $K_2CO_3$ (17.9 g, 130 mmol), benzyl bromide (13 mL, 111 mmol) and $Bu_4NI$ (0.250 g) at room temperature under nitrogen. The reaction mixture was stirred for 3 hours at room temperature. The reaction mixture was diluted with water and extracted with ethyl acetate. The combined organic extracts were washed with water, brine, dried over anhydrous sodium sulfate and concentrated to give the crude product, which was purified using silica gel column chromatography (2-5% ethyl acetate-hexane) to yield 4-benzyloxy-6-fluoro-3-methyl-naphthalene-2-carboxylic acid methyl ester (25.4 g, 84%) as an off-white solid. MS calcd. for $C_{20}H_{18}FO_3$ [(M+H)$^+$] 325, obsd. 325.1.

(4-Benzyloxy-6-fluoro-3-methyl-naphthalen-2-yl)-methanol

To a suspension of $LiAlH_4$ (8.8 g, 235 mmol) in dry THF (120 mL) was added a solution of 4-benzyloxy-6-fluoro-3-methyl-naphthalene-2-carboxylic acid methyl ester (25.4 g, 78.3 mmol) in THF (180 mL) dropwise at 0° C. under nitrogen. The reaction mixture was stirred at room temperature for 3 hours. After this time, the reaction mixture was cooled to 0° C. and quenched carefully by addition of cold water (10 mL) followed by 15% NaOH solution (10 mL) and additional water. The resulting solution was stirred for one hour, then filtered through a sintered glass funnel. The filter pad was washed with THF (50 mL). The combined filtrates were dried over $Na_2SO_4$, filtered, and concentrated to afford (4-benzyloxy-6-fluoro-3-methyl-naphthalen-2-yl)-methanol (21.5 g, 92%, crude) as a white solid. The crude product was used in the next step without further purification. MS calcd. for $C_{19}H_{16}FO_2$ [(M−H)$^-$] 295, obsd. 294.9.

Benzyloxy-3-chloromethyl-7-fluoro-2-methyl-naphthalene

To a solution of triphenylphosphine (41.6 g, 159 mmol) in dry THF (190 mL) was added $CCl_4$ (59 mL). The reaction mixture was stirred for 10 minutes and (4-benzyloxy-6-fluoro-3-methyl-naphthalen-2-yl)-methanol (21.5 g, 72.6 mmol) was introduced as a solid at room temperature under nitrogen. The resulting solution was refluxed for 2 hours. The solvent was distilled off under reduced pressure, and the residue was diluted with water. The resulting mixture was extracted twice with ethyl acetate. The combined organic extracts were washed with water and brine, dried over anhydrous sodium sulfate, filtered, and concentrated. Silica gel column chromatography (100-200 mesh, 5% ethyl acetate in hexanes) provided 1-benzyloxy-3-chloromethyl-7-fluoro-2-methyl-naphthalene (18.5 g, 81%) as an off-white solid.

(4-Benzyloxy-6-fluoro-3-methyl-naphthalen-2-yl)-acetic acid methyl ester

To a stirred solution of 1-benzyloxy-3-chloromethyl-7-fluoro-2-methyl-naphthalene (18.5 g, 58.9 mmol) in a THF-methanol mixture (2:3; 500 mL) was added $K_2CO_3$ (8.94 g, 64.7 mmol) and $PdCl_2(PPh_3)_2$ (2.06 g, 2.96 mmol) at room temperature. The solution was degassed by purging with argon for 5 minutes. The reaction mixture was stirred under a balloon of carbon monoxide overnight at room temperature. After this time, the reaction progress was monitored by TLC (5% ethyl acetate in hexanes). The reaction mixture was concentrated, and the obtained crude residue was diluted with water and extracted with ethyl acetate. The combined organic extracts were washed with water and brine, dried over anhydrous sodium sulfate, filtered, and concentrated to give a crude product. Silica gel chromatography (100-200 mesh, 5% ethyl acetate-hexanes) yielded (4-benzyloxy-6-fluoro-3-methyl-naphthalen-2-yl)-acetic acid methyl ester (5.5 g, 28%) as a pale yellow solid. MS calcd. for $C_{21}H_{20}FO_3$ [(M+H)$^+$] 339, obsd. 339.0.

(6-Fluoro-4-hydroxy-3-methyl-naphthalen-2-yl)-acetic acid methyl ester

To a stirred solution of (4-benzyloxy-6-fluoro-3-methyl-naphthalen-2-yl)-acetic acid methyl ester (15.8 g, 46.7 mmol) in MeOH (150 mL) was added 10% palladium on carbon (2.4 g). The resulting mixture was vigorously stirred under a balloon of hydrogen overnight. The reaction mixture was filtered through celite. The filtrate was concentrated to give the crude product, which was purified by silica gel chromatography (10% ethyl acetate in hexanes) to yield (6-fluoro-4-hydroxy-3-methyl-naphthalen-2-yl)-acetic acid methyl ester (9.5 g, 82%) as a white solid. MS calcd. for $C_{14}H_{14}FO_3$ $[(M+H)^+]$ 249, obsd. 249.1.

(6-Fluoro-3-methyl-4-trifluoromethanesulfonyloxy-naphthalen-2-yl)-acetic acid methyl ester A light yellow solution of (6-fluoro-4-hydroxy-3-methyl-naphthalen-2-yl)-acetic acid methyl ester (12.2 g, 49.1 mmol) in methylene chloride (500 mL) was cooled to 0° C. using an ice-acetone bath. Pyridine (5.17 mL, 63.9 mmol) was added and then trifluoromethanesulfonic acid anhydride (20.8 g, 73.7 mmol) was added dropwise to the cold solution over 40 minutes. The resulting light yellow solution was stirred for two hours at 0° C. before being warmed to room temperature. The reaction mixture was stirred for another 30 minutes at room temperature. The mixture was quenched with water (300 mL) and the two layers were separated. The aqueous layer was extracted with dichloromethane (200 mL). The combined organic layers were washed with brine, dried over anhydrous $MgSO_4$, filtered, and concentrated to give the crude product as a light yellow solid. The crude product was dissolved in dichloromethane (~50 mL) with heating and then the mixture was diluted with hexanes (~100 mL). Some of the solvent was removed by heating with a heat gun. The resulting light brown solution was stored in the freezer for 15 hours. A white solid precipitated, which was collected by filtration and washed with hexanes. After air drying, (6-fluoro-3-methyl-4-trifluoromethanesulfonyloxy-naphthalen-2-yl)-acetic acid methyl ester (14.32 g, 77%) was isolated. $^1$H NMR (400 MHz, DMSO-$d_6$) δ ppm 7.83 (dd, J=9.03, 5.52 Hz, 1 H), 7.75 (s, 1 H), 7.65 (dd, J=10.29, 2.51 Hz, 1 H), 7.31 (td, J=8.60, 2.38 Hz, 1 H), 3.85 (s, 2 H), 3.74 (s, 3 H).

Preparation of (6-chloro-3-methyl-4-trifluoromethanesulfonyloxy-naphthalen-2-yl)-acetic acid methyl ester

2-(4-Chloro-benzylidene)-3-methyl-succinic acid

After careful addition of absolute methanol (0.1 mL) to a suspension of sodium hydride (60% in mineral oil, 16 g, 0.40 mol) in anhydrous toluene (200 mL), a solution of 4-chloro-benzaldehyde (28 g, 0.20 mol) and 2-methyl-succinic acid dimethyl ester (48 g, 0.30 mol) in anhydrous toluene (100 mL) was added dropwise at room temperature under a stream of nitrogen. After being stirred at room temperature for 2 hours, the resulting mixture was diluted by addition of 2 N sodium hydroxide (200 mL) dropwise. The mixture was heated to 80° C., and stirred at this temperature for 2 hours. After cooling to room temperature, the aqueous layer was separated, washed with ethyl acetate (100 mL×3), then acidified with 2 N hydrochloric acid to pH 2 and extracted with ethyl acetate (150 mL×3). The combined organic layers were dried over sodium sulfate, and concentrated in vacuo. The residue was precipitated from ethyl acetate/petroleum ether (10:1) to give 2-(4-chloro-benzylidene)-3-methyl-succinic acid (13.4 g, 26%) as a yellow solid.

6-Chloro-4-hydroxy-3-methyl-naphthalene-2-carboxylic acid

To a flask containing trifluoromethanesulfonic acid (40 mL), 2-(4-chloro-benzylidene)-3-methyl-succinic acid (14.0 g, 55 mmol) was added in portions. After being stirred at room temperature for 18 hours, the resulting mixture was poured onto ice-water, and stirred for 15 minutes. The formed precipitate was collected by filtration, and dissolved in ethyl acetate (150 mL). The solution was dried over sodium sulfate, and concentrated in vacuo. The residue was precipitated from ethyl acetate/petroleum ether (1:10) to afford 6-chloro-4-hydroxy-3-methyl-naphthalene-2-carboxylic acid (12.7 g, 98%) as a pink solid.

7-Chloro-3-hydroxymethyl-2-methyl-naphthalen-1-ol

To a slurry of lithium aluminum hydride (4.1 g, 108 mmol) in tetrahydrofuran (80 mL) was added a solution of 6-chloro-4-hydroxy-3-methyl-naphthalene-2-carboxylic acid (12.7 g, 54 mmol) in tetrahydrofuran (80 mL) at 0° C. under a nitrogen atmosphere. After being heated at 60° C. for 5 hours, the resulting mixture was cooled to 0° C. and treated with 1 N hydrochloric acid to quench the reaction. The aqueous layer was extracted with ethyl acetate (100 mL×4). The combined organic layers were washed with brine (200 mL×2), dried over sodium sulfate and concentrated in vacuo to give 7-chloro-3-hydroxymethyl-2-methyl-naphthalen-1-ol (8.5 g, 71%) as a white solid.

7-Chloro-3-chloromethyl-2-methyl-naphthalen-1-ol

To a solution of triphenylphosphine (20 g, 76 mmol) in anhydrous tetrahydrofuran (165 mL) was added carbon tetrachloride (50 mL). After the mixture was stirred at room temperature for 20 minutes, 7-chloro-3-hydroxymethyl-2-methyl-naphthalen-1-ol (8.4 g, 37.7 mmol) was added as a solid under a nitrogen atmosphere. After being stirred at reflux for 2 hours, the resulting mixture was cooled to room temperature, and concentrated in vacuo. The residue was purified by column chromatography (elution with 5% ethyl acetate in petroleum ether) to afford 7-chloro-3-chloromethyl-2-methyl-naphthalen-1-ol (8.7 g, 96%) as a white solid.

(6-Chloro-4-hydroxy-3-methyl-naphthalen-2-yl)-acetic acid methyl ester

A flask containing 7-chloro-3-chloromethyl-2-methyl-naphthalen-1-ol (8.64 g, 36 mmol), bis(triphenylphosphine)dichloropalladium(II) (1.26 g, 1.8 mmol) and potassium carbonate (5.2 g, 37.8 mmol) was evacuated and then filled with carbon monoxide (balloon). Methanol (30 mL) and tetrahydrofuran (60 mL) were added by means of a syringe. After being stirred at room temperature under a carbon monoxide atmosphere overnight, the resulting mixture was diluted with water (100 mL), and extracted with ethyl acetate (100 mL). The organic layer was washed with water (50 mL×2). The combined aqueous layers were extracted with ethyl acetate (150 mL), and the combined organic layers were dried over sodium sulfate and concentrated in vacuo. The residue was purified by column chromatography (elution with 20% ethyl acetate in petroleum ether) to afford (6-chloro-4-hydroxy-3-methyl-naphthalen-2-yl)-acetic acid methyl ester (7.0 g, 74%) as an orange solid.

(6-Chloro-3-methyl-4-trifluoromethanesulfonyloxy-naphthalen-2-yl)-acetic acid methyl ester Triethylamine (3.72 mL, 27 mmol) was added to a stirred solution of (6-chloro-4-hydroxy-3-methyl-naphthalen-2-yl)-acetic acid methyl ester (1.4 g, 5.3 mmol) in dichloromethane (5 mL) at room temperature under nitrogen. After stirring for 5 minutes, trifluoromethanesulfonic anhydride (3.58 mL, 21.3 mmol) was added, and stirring continued for 16 hours at room temperature. The reaction mixture was diluted with dichloromethane. This solution was washed with water followed by a saturated aqueous solution of sodium bicarbonate and finally brine. The organic phase was dried, and then concentrated under reduced pressure to give the crude product. Silica gel column chromatography (ethyl acetate-hexane) afforded (6-chloro-3-methyl-4-trifluoromethanesulfonyloxy-naphthalen-2-yl)-acetic acid methyl ester (1.8 g, 86%) as a solid. MS calcd. for $C_{15}H_{11}ClF_3O_5S$ [(M−H)$^−$] 395, obsd. 395.2.

Preparation of [6-fluoro-3-methyl-4-(4,4,5,5-tetramethyl-[1,3,2]-dioxaborolan-2-yl)-naphthalen-2-yl]-acetic acid methyl ester A solution of (6-fluoro-3-methyl-4-trifluoromethanesulfonyloxy-naphthalen-2-yl)-acetic acid methyl ester (0.500 g, 1.31 mmol) in DMF (10 mL) was deoxygenated by purging with argon through the solution for 5 minutes at room temperature. Bis(pinacolato)diboron (0.668 g, 2.63 mmol), tetrakis(triphenylphosphine)palladium (0.151 g, 0.13 mmol) and potassium acetate (0.774 g, 7.9 mmol) were added simultaneously to the reaction flask solution at room temperature. The reaction mixture was heated at 90° C. under argon for 16 hours. The reaction mixture cooled to room temperature and then poured into ice-water and extracted twice with ethyl acetate. The collected organic phases were washed with water and brine, dried over anhydrous sodium sulfate and concentrated under reduced pressure to give the crude product. Silica gel column chromatography (5% ethyl acetate-hexane) provided [6-fluoro-3-methyl-4-(4,4,5,5-tetramethyl-[1,3,2]-dioxaborolan-2-yl)-naphthalen-2-yl]-acetic acid methyl ester (0.380 g, 80%) as a solid. MS calcd. for $C_{20}H_{25}BFO_4$ [(M+H)$^+$] 359, obsd. 359.1.

Preparation of [6-chloro-3-methyl-4-(4,4,5,5-tetramethyl-[1,3,2]-dioxaborolan-2-yl)-naphthalen-2-yl]-acetic acid methyl ester A solution of (6-chloro-3-methyl-4-trifluoromethanesulfonyloxy-naphthalen-2-yl)-acetic acid methyl ester (1.7 g, 4.28 mmol) in DMF (20 mL) was deoxygenated by purging with argon through the solution for 5 minutes at room temperature. Bis(pinacolato)diboron (2.21 g, 8.7 mmol), tetrakis(triphenylphosphine)palladium (0.5 g, 0.43 mmol) and potassium acetate (2.56 g, 25.7 mmol) were added simultaneously to the reaction flask solution at room temperature. The reaction mixture was heated at 90° C. under argon for 16 hours. The reaction mixture cooled to room temperature, poured into ice-water and extracted twice with ethyl acetate. The collected organic phases were washed with water and brine, dried over anhydrous sodium sulfate and concentrated under reduced pressure to give the crude product. Silica gel column chromatography (5% ethyl acetate-hexane) provided [6-chloro-3-methyl-4-(4,4,5,5-tetramethyl-[1,3,2]-dioxaborolan-2-yl)-naphthalen-2-yl]-acetic acid methyl ester (1.32 g, 83%) as a solid. MS calcd. for $C_{20}H_{25}BClO_4$ [(M+H)$^+$] 375, obsd. 375.1.

Though the $^1$H NMR spectra of the 1-bromo-4-(phenylsulfanyl)-benzene intermediates described below indicate that a pure compound was formed, the products actually contain a mixture of two compounds as confirmed by the presence of two products in GC/MS. The mixture was used in the next steps without further purification.

l) Preparation of 1-bromo-4-(2-chlorophenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. To this mixture was added 2-chloro-iodobenzene (0.63 g, 2.64 mmol). Copper(I) chloride (0.131 g, 1.32 mmol), tetramethyl heptanedione (0.14 mL, 0.66 mmol) and cesium carbonate (1.70 g, 5.22 mmol) were added. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(2-chlorophenylsulfanyl)-benzene (0.44 g). MS calcd. for $C_{12}H_8BrS$ [(M−Cl)] 265, obsd. 265.

m) Preparation of 1-bromo-4-(3-chlorophenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. After this time, 3-chloro-iodobenzene (0.63 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(3-chlorophenylsulfanyl)-benzene (0.7 g). MS calcd. for $C_{12}H_7BrClS$ [M−H] 298, obsd. 298.

n) Preparation of 1-bromo-4-(4-chlorophenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. After this time, 4-chloro-iodobenzene (0.63 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(2-chlorophenylsulfanyl)-benzene (0.35 g). MS calcd. for $C_{12}H_9BrClS$ [(M+H)$^+$] 300, obsd. 300.

Preparation of 1-bromo-4-(2-(trifluoromethyl)phenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. After this time, 2-iodobenzotrifluoride (0.72 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(2-(trifluoromethyl)phenylsulfanyl)-benzene (0.64 g) as a colorless liquid.

Preparation of 1-bromo-4-(2-(trifluoromethoxy)phenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. After this time, 2-(trifluoromethoxy)iodobenzene (0.73 g, 2.53 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(2-(trifluoromethoxy)phenylsulfanyl)benzene (0.72 g) as a solid.

Preparation of 1-bromo-4-(4-(trifluoromethoxy)phenylsulfanyl)-benzene

N-Methyl-2-pyrrolidone (10 mL) was added to 4-bromothiophenol (0.500 g, 2.64 mmol) in a sealed tube and the mixture was purged with argon for 5 minutes. After this time, 4-trifluoromethoxy-iodobenzene (0.73 g, 2.53 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-bromo-4-(4-(trifluoromethoxy)phenyl-sulfanyl)benzene (0.62 g) as a liquid.

Preparation of 1-(4-bromo-phenylsulfanyl)-2,4-dichloro-benzene

N-Methyl-2-pyrrolidone (10 mL) was added to 4-bromothiophenol (0.500 g, 2.64 mmol) in a sealed tube and the mixture was purged with argon for 5 minutes. After this time, 2,4-dichloroiodobenzene (0.72 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-2,4-dichloro-benzene (0.7 g).

Preparation of 1-(4-bromo-phenylsulfanyl)-2,5-dichloro-benzene

N-Methyl-2-pyrrolidone (10 mL) was added to 4-bromothiophenol (0.500 g, 2.64 mmol) in a sealed tube and the mixture was purged with argon for 5 minutes. After this time, 2,5-dichloroiodobenzene (0.72 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-2,5-dichloro-benzene (0.7 g).

Preparation of 1-(4-bromo-phenylsulfanyl)-2,4-difluoro-benzene

N-Methyl-2-pyrrolidone (10 mL) was added to 4-bromothiophenol (0.500 g, 2.64 mmol) in a sealed tube and the mixture was purged with argon for 5 minutes. After this time, 2,4-difluoroiodobenzene (0.63 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-2,4-difluorobenzene (0.56 g). MS calcd. for $C_{12}H_8BrF_2S$ [(M+H)$^+$] 302, obsd. 302.

Preparation of 1-(4-bromo-phenylsulfanyl)-2,6-difluoro-benzene

N-Methyl-2-pyrrolidone (10 mL) was added to 4-bromothiophenol (0.500 g, 2.64 mmol) in a sealed tube and the mixture was purged with argon for 5 minutes. After this time, 2,4-difluoroiodobenzene (0.63 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-2,6-difluorobenzene (0.29 g).

Preparation of 1-(4-bromo-phenylsulfanyl)-3,5-bis-trifluoromethyl-benzene

N-Methyl-2-pyrrolidone (10 mL) was added to 4-bromothiophenol (0.500 g, 2.64 mmol) in a sealed tube and the mixture was purged with argon for 5 minutes. After this time, 3,5-bis(trifluoromethyl)iodobenzene (0.89 g, 2.64 mmol), CuCl (0.131 g, 1.32 mmol), tetramethyl heptanedione (0.14 mL, 0.66 mmol) and cesium carbonate (1.70 g, 5.28 mmol)

were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-3,5-bis(trifluoromethyl)benzene (0.44 g). MS calcd. for $C_{14}H_8BrF_6S$ [(M+H)$^+$] 402, obsd. 402.

Preparation of
1-(4-bromo-phenylsulfanyl)-3,5-dichloro-benzene

N-Methyl-2-pyrrolidone (10 mL) was added to 4-bromothiophenol (0.500 g, 2.64 mmol) in a sealed tube and the mixture was purged with argon for 5 minutes. After this time, 3,5-dichloroiodobenzene (0.72 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-3,5-dichloro-benzene (0.7 g). MS calcd. for $C_{12}H_8BrCl_2S$ [(M+H)$^+$] 334, obsd. 334.

Preparation of
1-(4-bromo-phenylsulfanyl)-3,5-difluoro-benzene

N-Methyl-2-pyrrolidone (10 mL) was added to 4-bromothiophenol (0.500 g, 2.64 mmol) in a sealed tube and the mixture was purged with argon for 5 minutes. After this time, 3,5-difluoroiodobenzene (0.63 g, 2.64 mmol), CuCl (0.131 g, 1.32 mmol), tetramethyl heptanedione (0.14 mL, 0.66 mmol) and cesium carbonate (1.70 g, 5.28 mmol) were added to the reaction mixture. The reaction mixture was stirred at 130° C. under argon for 2 hours. The reaction mixture was cooled to room temperature, diluted with ethyl acetate, and filtered through a celite bed. The filtrate was washed with water and brine, dried over anhydrous sodium sulfate and concentrated under reduced pressure to yield the crude product. Silica gel chromatography (neat hexanes) provided impure 1-(4-bromo-phenylsulfanyl)-3,5-difluorobenzene (0.622 g). MS calcd. for $C_{12}H_8BrF_2S$ [(M+H)$^+$] 302, obsd. 302.

Preparation of
4-bromo-N-(2-hydroxy-ethyl)-benzenesulfonamide

To a stirred solution of 4-bromo-benzenesulfonyl chloride (1.00 g, 3.92 mmol) in methylene chloride (25 mL) was added N,N-dimethylaminopyridine (0.608 g, 4.98 mmol). The reaction mixture was cooled to 0° C., and ethanolamine (0.287 g, 4.70 mmol) was added dropwise. After stirring for 30 minutes, the reaction mixture was quenched with water (15 mL). The resulting mixture was extracted with methylene chloride (3×25 mL). The combined organic layers were dried over anhydrous sodium sulfate and concentrated under reduced pressure to give the crude product. Purification using silica gel chromatography (100-200 mesh, 10-15% ethyl acetate-hexane) provided 4-bromo-N-(2-hydroxy-ethyl)-benzenesulfonamide. MS calcd. for $C_8H_{11}BrNO_3S$ [(M+H)$^+$] 281, obsd. 282.2.

Preparation of [4-(4-Amino-phenyl)-6-fluoro-3-methyl-naphthalen-2-yl]-acetic acid methyl ester

[6-Fluoro-3-methyl-4-(4-nitro-phenyl)-naphthalen-2-yl]acetic acid methyl ester

To a mixture of (6-fluoro-3-methyl-4-trifluoromethanesulfonyloxy-naphthalen-2-yl)-acetic acid methyl ester (500 mg, 1.31 mmol), 4-nitrophenylboronic acid (658.5 mg, 3.94 mmol) and cesium carbonate (865.6 mg, 2.63 mmol) in dimethoxyethane (5 mL) was added [1,1'-bis(diphenylphosphino)ferrocene]dichloropalladium(II) (144.3 mg, 0.2 mmol) at room temperature under nitrogen. The resulting mixture was reacted using a microwave reactor (Personal Chemistry) at 120° C. for 30 minutes. Ethyl acetate (50 mL) was added and the organic layer was washed with water (30 ml) and brine solution (20 mL). The organic layers were dried over anhydrous magnesium sulfate, filtered, and concentrated in vacuo to give the crude product which was purified using an ISCO (90 g) column, eluting with 5-15% ethyl acetate in hexanes, to give [6-fluoro-3-methyl-4-(4-nitro-phenyl)-naphthalen-2-yl]-acetic acid methyl ester (197 mg, 42%) as a light yellow solid. $^1$H NMR (300 MHz, CDCl$_3$), δ ppm 8.40 (d, J=8.6 Hz, 2 H), 7.82 (dd, J=8.9, 5.7 Hz, 1 H), 7.77 (s, 1 H), 7.46 (d, J=8.6 Hz, 2 H), 7.21 (td, J=8.9, 2.4 Hz, 1 H), 6.76 (dd, J=11.2, 2.4 Hz, 1 H), 3.87 (s, 2 H), 3.74 (s, 3 H), 2.14 (s, 3 H). HRMS calcd. for $C_{20}H_{15}FNO_4$ [(M−H)$^−$] 352.0990, obsd. 352.0990.

[4-(4-Amino-phenyl)-6-fluoro-3-methyl-naphthalen-2-yl]acetic acid methyl ester

To a suspension of [6-fluoro-3-methyl-4-(4-nitro-phenyl)-naphthalen-2-yl]-acetic acid methyl ester (190 mg, 0.54 mmol) in methanol (3 mL) was added THF (2 mL). Then, zinc dust (287.1 mg, 4.4 mmol), and ammonium chloride (287.8 mg, 5.38 mmol) were added followed by water (1.3 mL). The reaction mixture was stirred at room temperature for 30 minutes. Solid was filtered and washed with ethyl acetate (20 mL). The solution was concentrated to remove organic solvent, and then diluted with water (25 mL). The mixture was extracted with ethyl acetate (2×20 mL). The combined organic extracts were washed with brine solution (30 mL) and dried over anhydrous magnesium sulfate. Filtration of the drying agent and concentration of the solvent under vacuum gave [4-(4-amino-phenyl)-6-fluoro-3-methyl-naphthalen-2-yl]-acetic acid methyl ester (118 mg, 67.7%) as a light brown solid. $^1$H NMR (300 MHz, CDCl$_3$) δ ppm 7.71-7.83 (m, 1 H), 7.69 (s, 1 H), 7.27 (s, 1 H), 7.10-7.22 (m, 1 H), 6.93-7.09 (m, 3 H), 6.83 (d, J=7.8 Hz, 1H), 3.86 (s, 2 H), 3.78 (br. s, 2 H), 3.74 (s, 3 H), 2.19 (s, 3 H). HRMS calcd. for $C_{20}H_{19}FNO_2$ [(M+H)$^+$] 324.1395, obsd. 324.1392.

Preparation of [4-(4-Amino-phenyl)-6-chloro-3-methyl-naphthalen-2-yl]-acetic acid methyl ester

[6-Chloro-3-methyl-4-(4-nitro-phenyl)-naphthalen-2-yl]acetic acid methyl ester

To a mixture of (6-chloro-3-methyl-4-trifluoromethanesulfonyloxy-naphthalen-2-yl)-acetic acid methyl ester (200 mg, 0.5 mmol), 4-nitrophenylboronic acid (170 mg, 1.1 mmol) and cesium carbonate (331 mg, 1 mmol) in dimethoxyethane (3 mL) was added [1,1'-bis(diphenylphosphino)ferrocene]dichloropalladium(II) (55.3 mg, 0.07 mmol) at room temperature under nitrogen. The resulting mixture was reacted using a microwave reactor (Personal Chemistry) at 120° C. for 30 minutes. Ethyl acetate (10 mL) was added and the organic layer was washed with water (20 mL) and brine solution (20 mL). The organic layers were dried over anhydrous magnesium sulfate, filtered, and concentrated in vacuo to give the crude product which was purified by using an ISCO (40 g) column chromatography eluting with 5-15% ethyl acetate in hexanes to give [6-chloro-3-methyl-4-(4-nitro-phenyl)-naphthalen-2-yl]-acetic acid methyl ester (138 mg, 74%) as a light yellow solid. $^1$H NMR (300 MHz, CDCl$_3$), δ ppm 8.40 (d, J=8.6 Hz, 2 H), 7.82 (dd, J=8.9, 5.7 Hz, 1 H), 7.77 (s, 1 H), 7.46 (d, J=8.6 Hz, 2 H), 7.21 (td, J=8.9, 2.4 Hz, 1 H), 6.76 (dd, J=11.2, 2.4 Hz, 1 H), 3.87 (s, 2 H), 3.74 (s, 3 H), 2.14 (s, 3 H). HRMS calcd. for $C_{20}H_{15}ClNO_4$ [(M–H)$^-$] 368.0695, obsd. 368.0695.

[4-(4-Amino-phenyl)-6-chloro-3-methyl-naphthalen-2-yl]acetic acid methyl ester

To a suspension of [6-chloro-3-methyl-4-(4-nitro-phenyl)-naphthalen-2-yl]-acetic acid methyl ester (133 mg, 0.36 mmol) in methanol (2 mL) was added THF (2 mL). Then, zinc dust (192.1 mg, 2.9 mmol) and ammonium chloride (192.6 mg, 3.6 mmol) were added followed by water (0.9 mL). The reaction mixture was stirred at room temperature for 10 minutes and TLC analysis of the mixture indicated the absence of starting material. The resulting solids were filtered and washed with ethyl acetate (20 mL). The solution was concentrated to remove organic solvent, then diluted with water (20 mL) and the mixture was extracted with ethyl acetate (2×20 mL). The combined organic extracts were washed with brine solution (30 mL) and dried over anhydrous magnesium sulfate. Filtration of the drying agent and concentration of the solvent under vacuum gave [4-(4-amino-phenyl)-6-chloro-3-methyl-naphthalen-2-yl]-acetic acid methyl ester (120 mg, 97.9%) as a light brown oil which solidified slowly. $^1$H NMR (300 MHz, DMSO-d$_6$) δ ppm 7.90 (d, J=8.7 Hz, 1 H), 7.79 (s, 1 H), 7.43 (dd, J=8.7, 1.9 Hz, 1 H), 7.27 (d, J=1.9 Hz, 1 H), 6.85 (d, J=8.2 Hz, 2 H), 6.72 (d, J=8.2 Hz, 2 H), 5.26 (s, 2 H), 3.93 (s, 2 H), 3.64 (s, 3 H), 2.09 (s, 3 H). HRMS calcd. for $C_{20}H_{18}ClNO_2$ [(M+H)$^+$] 340.1099, obsd. 340.1097.

Part II: Preparation of Certain Embodiments

Example 1

{6-Fluoro-3-methyl-4-[4-(toluene-2-sulfonyl)-phenyl]-naphthalen-2-yl}-acetic acid

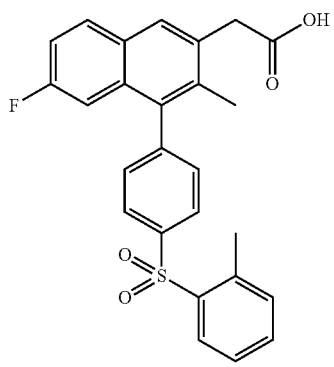 [SMILES: Cc1ccccc1S(=O)(=O)c1ccc(-c2c(C)c(CC(=O)O)cc3ccc(F)cc23)cc1]

1-(Chloromethyl)-2-[(4-chlorophenyl)-sulfonyl]benzene

To a solution of 1-(chloromethyl)-2-[(4-chlorophenyl)-sulfanyl]benzene (980 mg, 3.25 mmol) in dichloromethane (40 mL) was added m-chloroperbenzoic acid (2.5 g) at –10° C. The resulting suspension was stirred for 30 minutes and then slowly warmed to room temperature. The resulting clear solution was stirred for 15 hours at which time a solid had precipitated. The reaction mixture was then diluted with water and the dichloromethane was removed under vacuum. Then, the organic compound was extracted into ethyl acetate (2×50 mL) and the combined extracts were washed with water and brine solution. The organic layer was dried over anhydrous MgSO$_4$. Filtration and concentration gave the crude residue which was purified using an ISCO (40 g) column, eluting with 0-30% ethyl acetate in hexanes, to give 1.0 g (91%) of 1-(chloromethyl)-2-[(4-chlorophenyl)-sulfonyl]benzene. $^1$H NMR (300 MHz, CDCl$_3$) δ ppm 8.18 (d, J=7.5 Hz, 1 H), 7.85 (d, J=8.7 Hz, 2 H), 7.61-7.67 (m, 2 H), 7.52-7.59 (m, 1 H), 7.50 (d, J=8.7 Hz, 2 H), 4.99 (s, 2 H). HRMS calcd. for $C_{13}H_{11}Cl_2O_2S$ [(M–H)$^-$] 299.9779, obsd. 299.9779.

4,4,5,5-Tetramethyl-2-[4-(toluene-2-sulfonyl)-phenyl]-[1,3,2]dioxaborolane

To a mixture of bis(pinacolato)diboron (240 mg, 0.95 mmol), potassium carbonate (263 mg, 1.9 mmol), and tetrakis(triphenylphosphine)palladium(0) (73 mg, 0.063 mmol) was added a solution of 1-(chloromethyl)-2-[(4-chlorophenyl)-sulfonyl]benzene (190 mg, 0.57 mmol) in dioxane (12 mL) at room temperature. The resulting suspension was heated to 102° C. and stirred for 60 hours. The initial light brown color reaction mixture changed to a dark brown solution within 2-3 hours. The reaction mixture was cooled to room temperature, and saturated ammonium chloride and ethyl acetate were added. The two layers were separated and the aqueous layer was extracted one more time with ethyl acetate. The combined organic extracts were washed with water and brine solution. The organic layer was dried over anhydrous MgSO$_4$. Filtration and concentration gave a crude residue which was purified using an ISCO (40 g) column, eluting with 0-20% ethyl acetate in hexanes, to give 4,4,5,5-tetramethyl-2-[4-(toluene-2-sulfonyl)-phenyl]-[1,3,2]dioxaborolane (55 mg) as a light brown paste. $^1$H NMR spectrum of this compound indicates that it is ~50% pure with unknown impurities. This material was used directly in the next step without further purification. MS calcd. for $C_{22}H_{26}BNO_4S$ [(M+CH$_3$CN)$^+$] 400.0, obsd. 400.3.

{6-Fluoro-3-methyl-4-[4-(toluene-2-sulfonyl)-phenyl]-naphthalen-2-yl}-acetic acid methyl ester To a mixture of 4,4,5,5-tetramethyl-2-[4-(toluene-2-sulfonyl)-phenyl]-[1,3,2]dioxaborolane (50 mg, 0.14 mmol), (6-fluoro-3-methyl-4-trifluoromethanesulfonyloxy-naphthalen-2-yl)-acetic acid methyl ester (73 mg, 0.19 mmol), K$_3$PO$_4$ (81 mg, 0.38 mmol), palladium(II) acetate (14 mg, 0.06 mmol), and 2-dicyclohexylphosphino-2',6'-dimethoxy-biphenyl (49 mg, 0.12 mmol) were added anhydrous toluene (4 mL) and water (400 uL) at room temperature. The resulting light brown solution was heated to 125° C. for 15 hours. The reaction mixture was cooled to room temperature and diluted with brine solution and ethyl acetate. The two layers were separated and the aqueous layer was extracted with ethyl acetate and the combined extracts were washed with brine solution. The organic layer was dried over anhydrous MgSO$_4$. Filtration and concentration gave a crude residue which was purified using an ISCO (40 g) column, eluting with 0-40% ethyl acetate in hexanes, to give {6-fluoro-3-methyl-4-[4-(toluene-2-sulfonyl)-phenyl]-naphthalen-2-yl}-acetic acid methyl ester (20 mg, 31%). $^1$H NMR (300 MHz, CDCl$_3$) δ ppm 8.31 (d, J=7.5 Hz, 1 H), 8.01 (d, J=7.8 Hz, 2 H), 7.80 (dd, J=8.5, 6.0 Hz, 1 H), 7.75 (s, 1 H), 7.50-7.62 (m, 1 H), 7.47 (d, J=7.5 Hz, 1 H), 7.40 (d, J=7.8 Hz, 2 H), 7.32 (d, J=7.2 Hz, 1 H), 7.19 (td, J=8.5, 2.0 Hz, 1 H), 6.72 (d, J=10.9 Hz, 1 H), 3.85

(s, 2 H), 3.73 (s, 3 H), 2.56 (s, 3 H), 2.09 (s, 3 H). HRMS calcd. for $C_{27}H_{24}FO_4S$ [(M+H)$^+$] 463.1374, obsd. 463.1373.

{6-Fluoro-3-methyl-4-[4-(toluene-2-sulfonyl)-phenyl]-naphthalen-2-yl}-acetic acid To a solution of {6-fluoro-3-methyl-4-[4-(toluene-2-sulfonyl)-phenyl]-naphthalen-2-yl}-acetic acid methyl ester (20 mg, 0.04 mmol) in THF (5 mL) was added a solution of lithium hydroxide monohydrate (19.3 mg, 0.46 mmol) in water (1 mL) at room temperature. The resulting clear solution was stirred for 15 hours and then THF was removed under vacuum. Water (30 mL) was added and the mixture was acidified with 1.0N hydrochloric acid. The resulting solids were collected by filtration and washed with water and hexanes. After drying in air, {6-fluoro-3-methyl-4-[4-(toluene-2-sulfonyl)-phenyl]-naphthalen-2-yl}-acetic acid (10 mg, 52%) was isolated as off-white solid. $^1$H NMR (400 MHz, Methanol-d$_4$) δ ppm 8.27 (d, J=7.9 Hz, 1 H), 8.04 (d, J=8.2 Hz, 2 H), 7.88 (dd, J=8.8, 6.0 Hz, 1 H), 7.81 (s, 1 H), 7.61 (t, J=7.5 Hz, 1 H), 7.48-7.55 (m, 1 H), 7.48 (d, J=8.2 Hz, 2 H), 7.40 (d, J=7.5 Hz, 1 H), 7.22 (td, J=8.8, 2.1 Hz, 1H), 6.65 (dd, J=11.2, 2.1 Hz, 1 H), 3.86 (s, 2 H), 2.52 (s, 3 H), 2.11 (s, 3 H). HRMS (ES-) calcd. for $C_{26}H_{20}FO_4S$ [(M-H)$^-$] 447.1072, obsd. 447.1070.

Example 2

{4-[4-(2-Chloro-benzenesulfonyl)-phenyl]-6-fluoro-3-methyl-naphthalen-2-yl}-acetic acid

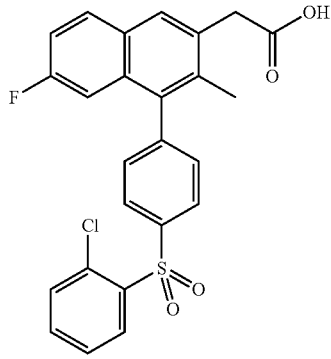 [SMILES: Cc1c(CC(=O)O)cc2ccc(F)cc2c1-c1ccc(S(=O)(=O)c2ccccc2Cl)cc1]

{4-[4-(2-Chloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.56 mmol) in dimethoxyethane (5 mL) was purged with argon for 5 minutes at room temperature. Tetrakis(triphenylphosphine)-palladium(0) (0.032 g, 0.028 mmol), impure 1-bromo-4-(2-chlorophenylsulfanyl)-benzene (0.334 g) and 1.0 M aqueous sodium bicarbonate (5 mL, 5 mmol) were added simultaneously to the reaction mixture under argon. The reaction mixture was refluxed for 2 hours and then cooled to room temperature. Water was added and the resulting mixture was extracted twice with ethyl acetate. The combined organic extracts were washed with water and brine, dried over anhydrous sodium sulfate, and concentrated under reduced pressure to give a crude product, which was purified using flash chromatography (0-3% ethyl acetate in hexanes) to give {4-[4-(2-chloro-phenylsulfanyl)-phenyl]-6-fluoro-3-methyl-naphthalen-2-yl}-acetic acid methyl ester (0.07 g, 28%) as a solid.

{4-[4-(2-Chloro-benzenesulfonyl)-phenyl]-6-fluoro-3-methyl-naphthalen-2-yl}-acetic acid methyl ester m-Chloroperoxybenzoic acid (0.1 g, approx. 0.6 mmol) was added to a stirred solution of {4-[4-(2-chloro-phenylsulfanyl)-phenyl]-6-fluoro-3-methyl-naphthalen-2-yl}-acetic acid methyl ester (0.07 g, 0.15 mmol) in dichloromethane (5 mL). The reaction mixture was stirred for 16 hours at room temperature. The reaction mixture was diluted with dichloromethane and washed with water, followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(2-chloro-benzenesulfonyl)-phenyl]-6-fluoro-3-methyl-naphthalen-2-yl}-acetic acid methyl ester (0.045 g, 60%) as a solid. MS calcd. for $C_{26}H_{21}ClFO_4S$ [(M+H)$^+$] 483, obsd. 483.0.

{4-[4-(2-Chloro-benzenesulfonyl)-phenyl]-6-fluoro-3-methyl-naphthalen-2-yl}-acetic acid Lithium hydroxide monohydrate (0.016 g, 0.38 mmol) was added to a stirred solution of {4-[4-(2-chloro-benzenesulfonyl)-phenyl]-6-fluoro-3-methyl-naphthalen-2-yl}-acetic acid methyl ester (0.045 g, 0.09 mmol) in a 3:1 THF—H$_2$O mixture (4 mL). The reaction mixture was stirred for 16 hours at room temperature. The THF was distilled off under reduced pressure. The crude residue was diluted with water, and acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(2-chloro-benzenesulfonyl)-phenyl]-6-fluoro-3-methyl-naphthalen-2-yl}-acetic acid (0.031 g, 71%) as a solid. $^1$H NMR (400 MHz, DMSO-d$_6$) δ ppm 12.42-12.50 (m, 1 H), 8.37-8.41 (m, 1 H), 8.08 (d, J=7.80 Hz, 2 H), 8.01 (dd, J=8.80, 6.40 Hz, 1 H), 7.91 (s, 1 H), 7.70-7.82 (m, 4 H), 7.53 (d, J=7.80 Hz, 2 H), 7.35-7.41 (m, 1 H), 6.62 (dd, J=11.00, 2.60 Hz, 1 H), 3.84 (s, 2 H), 2.05 (s, 3 H). MS calcd. for $C_{25}H_{17}ClFO_4S$ [(M-H)$^-$] 467, obsd. 467.3.

Example 3

{4-[4-(3-Chloro-benzenesulfonyl)-phenyl]-6-fluoro-3-methyl-naphthalen-2-yl}-acetic acid

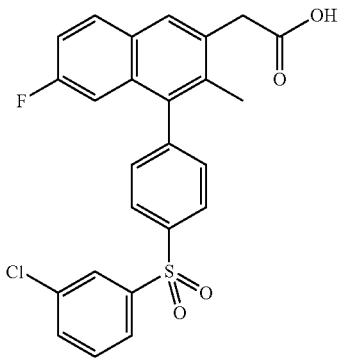 [SMILES: Cc1c(CC(=O)O)cc2ccc(F)cc2c1-c1ccc(S(=O)(=O)c2cccc(Cl)c2)cc1]

{4-[4-(3-Chloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)-palladium(0) (0.032 g, 0.028 mmol), impure 1-bromo-4-(3-chlorophenylsulfanyl)-benzene (0.25 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was purified using flash chromatography (0-3% ethyl acetate in hexanes) to give {4-[4-(3-chloro-phenylsulfanyl)-phenyl]-6-fluoro-3-methyl-naphthalen-2-yl}-acetic acid methyl ester (0.1 g, 40%) as a solid. MS calcd. for $C_{26}H_{21}ClFO_2S$ [(M+H)$^+$] 451, obsd. 451.1.

{4-[4-(3-Chloro-benzenesulfonyl)-phenyl]-6-fluoro-3-methyl-naphthalen-2-yl}-acetic acid methyl ester m-Chloroperoxybenzoic acid (0.19 g, approx. 1.11 mmol) was added to a stirred solution of {4-[4-(3-chloro-phenylsulfanyl)-phenyl]-6-fluoro-3-methyl-naphthalen-2-yl}-acetic acid methyl ester (0.1 g, 0.22 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(3-chloro-benzenesulfonyl)-phenyl]-6-fluoro-3-methyl-naphthalen-2-yl}-acetic acid methyl ester (0.063 g, 59%) as a solid. MS calcd. for $C_{26}H_{21}ClFO_4S$ [(M+H)$^+$] 483, obsd. 483.0.

{4-[4-(3-Chloro-benzenesulfonyl)-phenyl]-6-fluoro-3-methyl-naphthalen-2-yl}-acetic acid Lithium hydroxide monohydrate (0.022 g, 0.52 mmol) was added to a stirred solution of {4-[4-(3-chloro-benzenesulfonyl)-phenyl]-6-fluoro-3-methyl-naphthalen-2-yl}-acetic acid methyl ester (0.063 g, 0.12 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(3-chloro-benzenesulfonyl)-phenyl]-6-fluoro-3-methyl-naphthalen-2-yl}-acetic acid (0.031 g, 51%) as a solid. $^1$H NMR (400 MHz, DMSO-d$_6$) δ ppm 12.47 (br. s, 1 H) 8.19 (d, J=8.20 Hz, 2 H) 8.13 (t, J=2.10 Hz, 1 H) 8.05 (d, J=7.60 Hz, 1 H) 8.00 (dd, J=8.90, 5.80 Hz, 1 H) 7.91 (s, 1 H) 7.84 (d, J=7.60 Hz, 1 H) 7.72 (t, J=8.10 Hz, 1 H) 7.54 (d, J=8.10 Hz, 2 H) 7.38 (td, J=8.30, 2.60 Hz, 1 H) 6.64 (dd, J=10.90, 2.40 Hz, 1 H) 3.84 (s, 2 H) 2.03 (s, 3 H). MS calcd. for $C_{25}H_{18}ClFO_4S$ [(M−H)$^−$] 467, obsd. 467.3.

Example 4

{4-[4-(4-Chloro-benzenesulfonyl)-phenyl]-6-fluoro-3-methyl-naphthalen-2-yl}-acetic acid

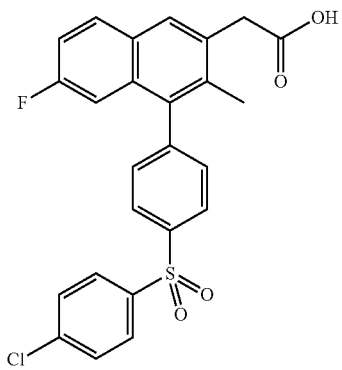 [SMILES: Cc1c(CC(=O)O)cc2ccc(F)cc2c1-c1ccc(S(=O)(=O)c2ccc(Cl)cc2)cc1]

{4-[4-(4-Chloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-bromo-4-(4-chlorophenylsulfanyl)-benzene (0.25 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(4-chlorophenylsulfanyl)-phenyl]-6-fluoro-3-methyl-naphthalen-2-yl}-acetic acid methyl ester (0.094 g, 37%) as a solid. MS calcd. for $C_{26}H_{21}ClFO_2S$ [(M+H)$^+$] 451, obsd. 451.0.

{4-[4-(4-Chloro-benzenesulfonyl)-phenyl]-6-fluoro-3-methyl-naphthalen-2-yl}-acetic acid methyl ester m-Chloroperoxybenzoic acid (0.172 g, approx. 1.0 mmol) was added to a stirred solution of {4-[4-(4-chloro-phenylsulfanyl)-phenyl]-6-fluoro-3-methyl-naphthalen-2-yl}-acetic acid methyl ester (0.094 g, 0.2 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(4-chloro-benzenesulfonyl)-phenyl]-6-fluoro-3-methyl-naphthalen-2-yl}-acetic acid methyl ester (0.037 g, 38%) as a solid.

{4-[4-(4-Chloro-benzenesulfonyl)-phenyl]-6-fluoro-3-methyl-naphthalen-2-yl}-acetic acid Lithium hydroxide monohydrate (0.013 g, 0.30 mmol) was added to a stirred solution of {4-[4-(4-chloro-benzenesulfonyl)-phenyl]-6-fluoro-3-methyl-naphthalen-2-yl}-acetic acid methyl ester (0.037 g, 0.076 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(4-chloro-benzenesulfonyl)-phenyl]-6-fluoro-3-methyl-naphthalen-2-yl}-acetic acid (0.035 g, 98%) as a solid. $^1$H NMR (400 MHz, DMSO-d$_6$) δ ppm 12.48 (br. s., 1 H) 8.14 (d, J=7.82 Hz, 2 H) 8.09 (d, J=8.80 Hz, 2 H) 7.97-8.04 (m, 1 H) 7.90 (s, 1 H) 7.77 (d, J=7.82 Hz, 2 H) 7.53 (d, J=7.83 Hz, 2 H) 7.38 (td, J=8.30, 2.40 Hz, 1 H) 6.63 (d, J=10.76 Hz, 1H) 3.83 (s, 2 H) 2.02 (s, 3 H). MS calcd. for C$_{25}$H$_{18}$ClFO$_4$S [(M−H)$^−$] 467, obsd. 467.3.

Example 5

{6-Fluoro-3-methyl-4-[4-(2-trifluoromethyl-benzenesulfonyl)-phenyl]-naphthalen-2-yl}-acetic acid

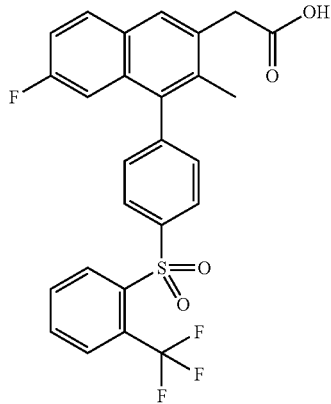 [SMILES: Cc1c(CC(=O)O)cc2ccc(F)cc2c1-c1ccc(S(=O)(=O)c2ccccc2C(F)(F)F)cc1]

{6-Fluoro-3-methyl-4-[4-(2-trifluoromethyl-phenylsulfanyl)-phenyl]-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-bromo-4-(2-(trifluoromethyl)-phenylsulfanyl)-benzene (0.279 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product. Flash chromatography (0-3% ethyl acetate in hexanes) provided {6-fluoro-3-methyl-4-[4-(2-trifluoromethyl-phenylsulfanyl)-phenyl]-naphthalen-2-yl}-acetic acid methyl ester (0.088 g, 32%) as a solid. MS calcd. for C$_{27}$H$_{19}$F$_4$O$_2$S [(M−H)$^−$] 483, obsd. 483.0.

{6-Fluoro-3-methyl-4-[4-(2-trifluoromethyl-benzenesulfonyl)-phenyl]-naphthalen-2-yl}-acetic acid methyl ester m-Chloroperoxybenzoic acid (0.156 g, approx. 0.90 mmol) was added to a stirred solution of {6-fluoro-3-methyl-4-[4-(2-trifluoromethyl-phenylsulfanyl)-phenyl]-naphthalen-2-yl}-acetic acid methyl ester (0.088 g, 0.18 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-fluoro-3-methyl-4-[4-(2-trifluoromethyl-benzenesulfonyl)-phenyl]-naphthalen-2-yl}-acetic acid methyl ester (0.047 g, 50%) as a solid. MS calcd. for C$_{27}$H$_{21}$F$_4$O$_4$S [(M+H)$^+$] 517, obsd. 517.2.

{6-Fluoro-3-methyl-4-[4-(2-trifluoromethyl-benzenesulfonyl)-phenyl]-naphthalen-2-yl}-acetic acid Lithium hydroxide monohydrate (0.015 g, 0.36 mmol) was added to a stirred solution of {6-fluoro-3-methyl-4-[4-(2-trifluoromethyl-benzenesulfonyl)-phenyl]-naphthalen-2-yl}-acetic acid methyl ester (0.047 g, 0.091 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-fluoro-3-methyl-4-[4-(2-trifluoromethyl-benzenesulfonyl)-phenyl]-naphthalen-2-yl}-acetic acid (0.031 g, 68%) as a solid. $^1$H NMR (400 MHz, DMSO-d$_6$) δ ppm 12.49 (br. s., 1 H) 8.57 (d, J=7.83 Hz, 1 H) 7.98-8.13 (m, 6 H) 7.90 (s, 1 H) 7.53 (d, J=8.31 Hz, 2 H) 7.38 (td, J=8.80, 2.40 Hz, 1 H) 6.61 (dd, J=11.00, 2.50 Hz, 1 H) 3.84 (s, 2 H) 2.03 (s, 3 H) MS calcd. for C$_{26}$H$_{17}$F$_4$O$_4$S [(M−H)$^−$] 501, obsd. 501.0.

Example 6

{6-Fluoro-3-methyl-4-[4-(2-trifluoromethoxy-benzenesulfonyl)-phenyl]-naphthalen-2-yl}-acetic acid

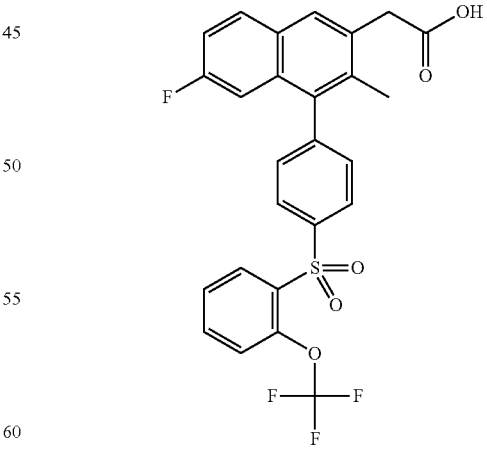

{6-Fluoro-3-methyl-4-[4-(2-trifluoromethoxy-phenylsulfanyl)-phenyl]-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-bromo-4-(2-(trifluoromethoxy)phenylsulfanyl)benzene (0.214 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-fluoro-3-methyl-4-[4-(2-trifluoromethoxyphenylsulfanyl)-phenyl]-naphthalen-2-yl}-acetic acid methyl ester (0.089 g, 32%) as a solid. MS calcd. for $C_{27}H_{19}F_4O_3S$ [(M–H)⁻] 499, obsd. 499.1.

{6-Fluoro-3-methyl-4-[4-(2-trifluoromethoxy-benzenesulfonyl)-phenyl]-naphthalen-2-yl}-acetic acid methyl ester m-Chloroperoxybenzoic acid (0.153 g, approx. 0.89 mmol) was added to a stirred solution of {6-fluoro-3-methyl-4-[4-(2-trifluoromethoxy-phenylsulfanyl)-phenyl]-naphthalen-2-yl}-acetic acid methyl ester (0.089 g, 0.178 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-fluoro-3-methyl-4-[4-(2-trifluoromethoxy-benzenesulfonyl)-phenyl]-naphthalen-2-yl}-acetic acid methyl ester (0.038 g, 40%) as a solid. MS calcd. for $C_{27}H_{19}F_4O_5S$ [(M–H)⁻] 531, obsd. 531.1.

{6-Fluoro-3-methyl-4-[4-(2-trifluoromethoxy-benzenesulfonyl)-phenyl]-naphthalen-2-yl}-acetic acid Lithium hydroxide monohydrate (0.012 g, 0.28 mmol) was added to a stirred solution of {6-fluoro-3-methyl-4-[4-(2-trifluoromethoxy-benzenesulfonyl)-phenyl]-naphthalen-2-yl}-acetic acid methyl ester (0.038 g, 0.071 mmol) in a 3:1 THF—H₂O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-fluoro-3-methyl-4-[4-(2-trifluoromethoxy-benzenesulfonyl)-phenyl]-naphthalen-2-yl}-acetic acid (0.034 g, 92%) as a solid. ¹H NMR (400 MHz, DMSO-d₆) δ ppm 12.49 (br. s., 1 H) 8.35 (d, J=7.82 Hz, 1 H) 8.06 (d, J=7.82 Hz, 2 H) 7.97-8.03 (m, 1 H) 7.91 (br. s., 2 H) 7.74 (t, J=7.90 Hz, 1 H) 7.59-7.67 (m, 1 H) 7.55 (d, J=7.82 Hz, 2 H) 7.38 (t, J=8.20 Hz, 1 H) 6.60 (d, J=10.80 Hz, 1 H) 3.84 (s, 2 H) 2.04 (s, 3 H). MS calcd. for $C_{26}H_{17}F_4O_5S$ [(M–H)⁻] 517, obsd. 517.3.

Example 7

{6-Fluoro-3-methyl-4-[4-(4-trifluoromethoxy-benzenesulfonyl)-phenyl]-naphthalen-2-yl}-acetic acid

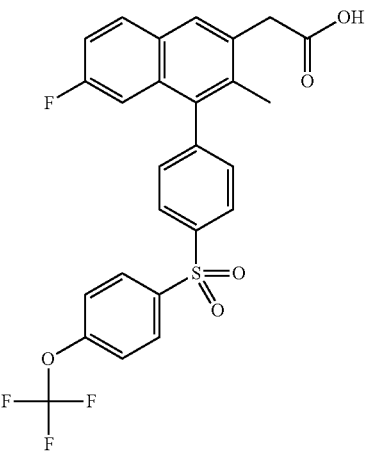 [SMILES: Cc1c(CC(=O)O)cc2ccc(F)cc2c1-c1ccc(S(=O)(=O)c2ccc(OC(F)(F)F)cc2)cc1]

{6-Fluoro-3-methyl-4-[4-(4-trifluoromethoxy-phenylsulfanyl)-phenyl]-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-bromo-4-(4-(trifluoromethoxy)phenylsulfanyl)benzene (0.214 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-fluoro-3-methyl-4-[4-(4-trifluoromethoxyphenylsulfanyl)-phenyl]-naphthalen-2-yl}-acetic acid methyl ester (0.154 g, 55%) as a solid.

{6-Fluoro-3-methyl-4-[4-(4-trifluoromethoxy-benzenesulfonyl)-phenyl]-naphthalen-2-yl}-acetic acid methyl ester m-Chloroperoxybenzoic acid (0.27 g, approx. 1.54 mmol) was added to a stirred solution of {6-fluoro-3-methyl-4-[4-(2-trifluoromethoxy-phenylsulfanyl)-phenyl]-naphthalen-2-yl}-acetic acid methyl ester (0.154 g, 0.30 mmol) in dichloromethane (5 mL). The reaction mixture was stirred for 16 hours at room temperature. The mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-fluoro-3-methyl-4-[4-(4-trifluoromethoxy-benzenesulfonyl)-phenyl]-naphthalen-2-yl}-acetic acid methyl ester (0.032 g, 20%) as a solid. MS calcd. for $C_{27}H_{19}F_4O_5S$ [(M–H)⁻] 531, obsd. 531.4.

{6-Fluoro-3-methyl-4-[4-(4-trifluoromethoxy-benzenesulfonyl)-phenyl]-naphthalen-2-yl}-acetic acid Lithium hydroxide monohydrate (0.011 g, 0.26 mmol) was added to a stirred solution of {6-fluoro-3-methyl-4-[4-(4-trifluoromethoxy-benzenesulfonyl)-phenyl]-naphthalen-2-yl}-acetic acid methyl ester (0.032 g, 0.06 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-fluoro-3-methyl-4-[4-(4-trifluoromethoxy-benzenesulfonyl)-phenyl]-naphthalen-2-yl}-acetic acid (0.027 g, 87%) as a solid. $^1$H NMR (400 MHz, DMSO-d$_6$) δ ppm 12.48 (br. s, 1 H) 8.23 (d, J=8.90 Hz, 2 H) 8.16 (d, J=8.30 Hz, 2 H) 7.97-8.05 (m, 1 H) 7.90 (s, 1 H) 7.68 (d, J=8.70 Hz, 2 H) 7.54 (d, J=8.80 Hz, 2H) 7.34-7.43 (m, 1H) 6.63 (d, J=10.90 Hz, 1 H) 3.83 (s, 2 H) 2.03 (s, 3 H) MS calcd. for C$_{26}$H$_{17}$F$_4$O$_5$S [(M–H)$^-$] 517, obsd. 517.3.

Example 8

{4-[4-(2,4-Dichloro-benzenesulfonyl)-phenyl]-6-fluoro-3-methyl-naphthalen-2-yl}-acetic acid

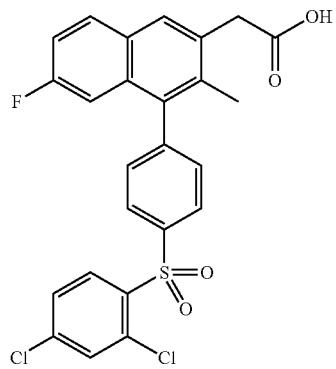 [SMILES: Cc1c(CC(=O)O)cc2ccc(F)cc2c1-c1ccc(S(=O)(=O)c2ccc(Cl)cc2Cl)cc1]

{4-[4-(2,4-Dichloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-2,4-dichlorobenzene (0.2 g, 0.61 mmol) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(2,4-dichloro-phenylsulfanyl)-phenyl]-6-fluoro-3-methyl-naphthalen-2-yl}-acetic acid methyl ester (0.077 g, 29%) as a solid.

{4-[4-(2,4-Dichloro-benzenesulfonyl)-phenyl]-6-fluoro-3-methyl-naphthalen-2-yl}-acetic acid methyl ester m-Chloroperoxybenzoic acid (0.1 g, approx. 0.58 mmol) was added to a stirred solution of {4-[4-(2,4-dichloro-phenylsulfanyl)-phenyl]-6-fluoro-3-methyl-naphthalen-2-yl}-acetic acid methyl ester (0.06 g, 0.12 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(2,4-dichlorobenzenesulfonyl)-phenyl]-6-fluoro-3-methyl-naphthalen-2-yl}-acetic acid methyl ester (0.028 g, 44%) as a solid.

{4-[4-(2,4-Dichloro-benzenesulfonyl)-phenyl]-6-fluoro-3-methyl-naphthalen-2-yl}-acetic acid Lithium hydroxide monohydrate (0.009 g, 0.22 mmol) was added to a stirred solution of {4-[4-(2,4-dichlorobenzenesulfonyl)-phenyl]-6-fluoro-3-methyl-naphthalen-2-yl}-acetic acid methyl ester (0.028 g, 0.054 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(2,4-dichlorobenzenesulfonyl)-phenyl]-6-fluoro-3-methyl-naphthalen-2-yl}-acetic acid (0.018 g, 66%) as a solid. $^1$H NMR (400 MHz, DMSO-d$_6$) δ ppm 12.49 (br. s., 1 H) 8.37 (d, J=7.82 Hz, 1 H) 8.09 (d, J=7.82 Hz, 2 H) 8.01 (dd, J=9.00, 6.70 Hz, 1H) 7.96 (s, 1 H) 7.91 (s, 1 H) 7.83 (d, J=8.80 Hz, 1 H) 7.54 (d, J=7.82 Hz, 2 H) 7.39 (t, J=8.00 Hz, 1 H) 6.63 (d, J=10.76 Hz, 1 H) 3.84 (s, 2 H) 2.05 (s, 3 H) MS calcd. for C$_{25}$H$_{16}$Cl$_2$FO$_4$S [(M–H)$^-$] 501, obsd. 501.2.

Example 9

{4-[4-(2,5-Dichloro-benzenesulfonyl)-phenyl]-6-fluoro-3-methyl-naphthalen-2-yl}-acetic acid

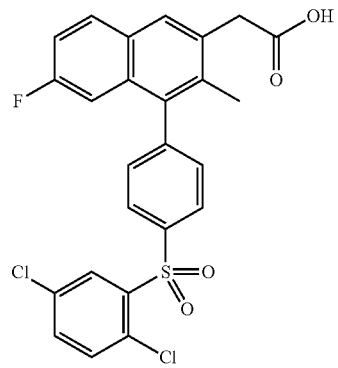 [SMILES: Cc1c(CC(=O)O)cc2ccc(F)cc2c1-c1ccc(S(=O)(=O)c2cc(Cl)ccc2Cl)cc1]

{4-[4-(2,5-Dichloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-2,5-dichlorobenzene (0.2 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(2,5-dichloro-phenylsulfanyl)-phenyl]-6-fluoro-3-methyl-naphthalen-2-yl}-acetic acid methyl ester (0.089 g, 33%) as a solid.

{4-[4-(2,5-Dichloro-benzenesulfonyl)-phenyl]-6-fluoro-3-methyl-naphthalen-2-yl}-acetic acid methyl ester m-Chloroperoxybenzoic acid (0.15 g, approx. 0.87 mmol) was added to a stirred solution of {4-[4-(2,5-dichloro-phenylsulfanyl)-phenyl]-6-fluoro-3-methyl-naphthalen-2-yl}-acetic acid methyl ester (0.085 g, 0.17 mmol) in dichloromethane (5 mL). The reaction mixture was stirred for 16 hours at room temperature. The mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(2,5-dichlorobenzenesulfonyl)-phenyl]-6-fluoro-3-methyl-naphthalen-2-yl}-acetic acid methyl ester (0.033 g, 37%) as a solid.

{4-[4-(2,5-Dichloro-benzenesulfonyl)-phenyl]-6-fluoro-3-methyl-naphthalen-2-yl}-acetic acid Lithium hydroxide monohydrate (0.011 g, 0.26 mmol) was added to a stirred solution of {4-[4-(2,5-dichlorobenzenesulfonyl)-phenyl]-6-fluoro-3-methyl-naphthalen-2-yl}-acetic acid methyl ester (0.033 g, 0.063 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(2,5-dichlorobenzenesulfonyl)-phenyl]-6-fluoro-3-methyl-naphthalen-2-yl}-acetic acid (0.027 g, 84%) as a solid. $^1$H NMR (400 MHz, DMSO-d$_6$) δ ppm 12.52 (br. s, 1 H) 8.33 (s, 1 H) 8.16 (d, J=7.82 Hz, 2 H) 7.99 (s, 1 H) 7.85-7.93 (m, 2 H) 7.77 (d, J=8.80 Hz, 1 H) 7.55 (d, J=8.80 Hz, 2 H) 7.49 (d, J=8.80 Hz, 1 H) 6.95 (s, 1 H) 3.86 (s, 2 H) 2.05 (s, 3 H) MS calcd. for C$_{25}$H$_{16}$Cl$_2$FO$_4$S [(M−H)$^-$] 501, obsd. 501.2.

Example 10

{4-[4-(2,4-Difluoro-benzenesulfonyl)-phenyl]-6-fluoro-3-methyl-naphthalen-2-yl}-acetic acid

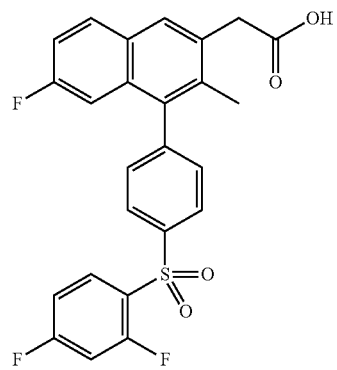 [SMILES: Cc1c(CC(=O)O)cc2ccc(F)cc2c1-c1ccc(S(=O)(=O)c2ccc(F)cc2F)cc1]

{4-[4-(2,4-Difluoro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-2,4-difluorobenzene (0.184 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(2,4-difluoro-phenylsulfanyl)-phenyl]-6-fluoro-3-methyl-naphthalen-2-yl}-acetic acid methyl ester (0.082 g, 33%) as a solid.

{4-[4-(2,4-Difluoro-benzenesulfonyl)-phenyl]-6-fluoro-3-methyl-naphthalen-2-yl}-acetic acid methyl ester m-Chloroperoxybenzoic acid (0.15 g, approx. 0.90 mmol) was added to a stirred solution of {4-[4-(2,4-difluoro-phenylsulfanyl)-phenyl]-6-fluoro-3-methyl-naphthalen-2-yl}-acetic acid methyl ester (0.082 g, 0.18 mmol) in dichloromethane (5 mL). The reaction mixture was stirred for 16 hours at room temperature. The mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(2,4-difluorobenzenesulfonyl)-phenyl]-6-fluoro-3-methyl-naphthalen-2-yl}-acetic acid methyl ester (0.028 g, 32%) as a solid. MS calcd. for C$_{26}$H$_{18}$F$_3$O$_4$S [(M−H)$^-$] 483, obsd. 483.3.

{4-[4-(2,4-Difluoro-benzenesulfonyl)-phenyl]-6-fluoro-3-methyl-naphthalen-2-yl}-acetic acid Lithium hydroxide monohydrate (0.01 g, 0.23 mmol) was added to a stirred solution of {4-[4-(2,4-difluorobenzenesulfonyl)-phenyl]-6-fluoro-3-methyl-naphthalen-2-yl}-acetic acid methyl ester (0.028 g, 0.057 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(2,4-difluorobenzenesulfonyl)-phenyl]-6-fluoro-3-methyl-naphthalen-2-yl}-acetic acid (0.02 g, 74%) as a solid. $^1$H NMR (400 MHz, DMSO-d$_6$) δ ppm 12.50 (br. S, 1 H) 8.23 (q, J=7.60 Hz, 1 H) 8.12 (d, J=7.82 Hz, 2 H) 8.01 (dd, J=9.40, 6.20 Hz, 1H) 7.91 (s, 1 H) 7.63 (t, J=9.40 Hz, 1 H) 7.56 (d, J=8.31 Hz, 2 H) 7.45 (t, J=8.60 Hz, 1 H) 7.39 (td, J=9.00, 2.60 Hz, 1 H) 6.64 (dd, J=11.00, 2.40 Hz, 1 H) 3.84 (s, 2 H) 2.04 (s, 3 H). MS calcd. for C$_{25}$H$_{16}$F$_3$O$_4$S [(M−H)$^-$] 469, obsd. 469.3.

Example 11

{4-[4-(2,6-Difluoro-benzenesulfonyl)-phenyl]-6-fluoro-3-methyl-naphthalen-2-yl}-acetic acid

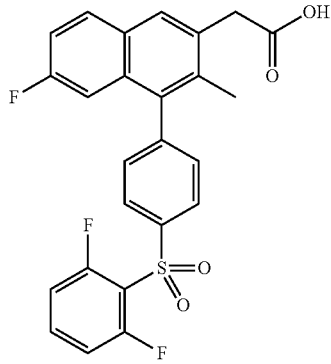 [SMILES: Cc1c(CC(=O)O)cc2ccc(F)cc2c1-c1ccc(S(=O)(=O)c2c(F)cccc2F)cc1]

{4-[4-(2,6-Difluoro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.1 g, 0.28 mmol) in dimethoxyethane (4 mL) was purged with argon for 5 minutes at room temperature. Tetrakis(triphenylphosphine)palladium(0) (0.032 g, 0.028 mmol), impure 1-(4-bromo-phenylsulfanyl)-2,6-difluorobenzene (0.084 g) and 2.0 M aqueous sodium carbonate (1 mL, 2 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(2,6-difluoro-phenylsulfanyl)-phenyl]-6-fluoro-3-methyl-naphthalen-2-yl}-acetic acid methyl ester (0.027 g, 21%) as a solid.

{4-[4-(2,6-Difluoro-benzenesulfonyl)-phenyl]-6-fluoro-3-methyl-naphthalen-2-yl}-acetic acid methyl ester m-Chloroperoxybenzoic acid (0.114 g, approx. 0.66 mmol) was added to a stirred solution of {4-[4-(2,6-difluoro-phenylsulfanyl)-phenyl]-6-fluoro-3-methyl-naphthalen-2-yl}-acetic acid methyl ester (0.06 g, 0.13 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(2,6-difluorobenzenesulfonyl)-phenyl]-6-fluoro-3-methyl-naphthalen-2-yl}-acetic acid methyl ester (0.031 g, 48%) as a solid. MS calcd. for C$_{26}$H$_{18}$F$_3$O$_4$S [(M−H)$^-$] 483, obsd. 483.4.

{4-[4-(2,6-Difluoro-benzenesulfonyl)-phenyl]-6-fluoro-3-methyl-naphthalen-2-yl}-acetic acid Lithium hydroxide monohydrate (0.011 g, 0.26 mmol) was added to a stirred solution of {4-[4-(2,6-difluorobenzenesulfonyl)-phenyl]-6-fluoro-3-methyl-naphthalen-2-yl}-acetic acid methyl ester (0.031 g, 0.064 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(2,6-difluorobenzenesulfonyl)-phenyl]-6-fluoro-3-methyl-naphthalen-2-yl}-acetic acid (0.024 g, 80%) as a solid. The final product was isolated with a significant amount of water as an impurity. $^1$H NMR (300 MHz, DMSO-d$_6$) δ ppm 8.17 (d, J=7.91 Hz, 2 H), 8.01 (dd, J=9.23, 6.22 Hz, 1 H), 7.91 (s, 1 H), 7.80-7.88 (m, 1 H), 7.58 (d, J=8.48 Hz, 2 H), 7.39 (t, J=9.04 Hz, 3 H), 6.64 (d, J=11.87 Hz, 1 H), 3.83 (s, 2 H), 2.04 (s, 3 H). MS calcd. for C$_{25}$H$_{16}$F$_3$O$_4$S [(M−H)$^-$] 469, obsd. 469.2.

Example 12

{4-[4-(3,5-Bis-trifluoromethyl-benzenesulfonyl)-phenyl]-6-fluoro-3-methyl-naphthalen-2-yl}-acetic acid

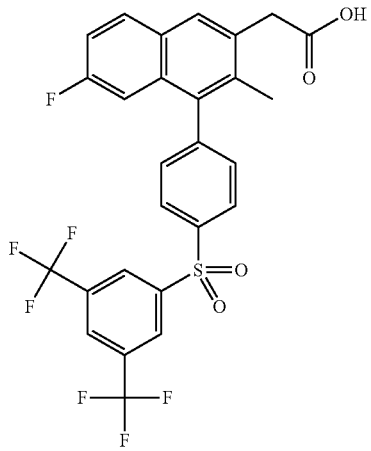 [SMILES: Cc1c(CC(=O)O)cc2ccc(F)cc2c1-c1ccc(S(=O)(=O)c2cc(C(F)(F)F)cc(C(F)(F)F)c2)cc1]

{4-[4-(3,5-Bis-trifluoromethyl-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-3,5-bis-trifluoromethyl-benzene (0.29 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(3,5-bis-trifluoromethyl-phenylsulfanyl)-phenyl]-6-fluoro-3-methyl-naphthalen-2-yl}-acetic acid methyl ester (0.115 g, 37%) as a solid.

{4-[4-(3,5-Bis-trifluoromethyl-benzenesulfonyl)-phenyl]-6-fluoro-3-methyl-naphthalen-2-yl}-acetic acid methyl ester m-Chloroperoxybenzoic acid (0.18 g, approx. 1.04 mmol) was added to a stirred solution of {4-[4-(2,6-difluoro-phenylsulfanyl)-phenyl]-6-fluoro-3-methyl-naphthalen-2-yl}-acetic acid methyl ester (0.115 g, 0.2 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(3,5-bis-trifluoromethyl-benzenesulfonyl)-phenyl]-6-fluoro-3-methyl-naphthalen-2-yl}-acetic acid methyl ester (0.043 g, 36%) as a solid. MS calcd. for $C_{28}H_{18}F_7O_4S$ [(M−H)$^-$] 583, obsd. 583.0.

{4-[4-(3,5-Bis-trifluoromethyl-benzenesulfonyl)-phenyl]-6-fluoro-3-methyl-naphthalen-2-yl}-acetic acid Lithium hydroxide monohydrate (0.012 g, 0.29 mmol) was added to a stirred solution of {4-[4-(3,5-bis-trifluoromethyl-benzenesulfonyl)-phenyl]-6-fluoro-3-methyl-naphthalen-2-yl}-acetic acid methyl ester (0.043 g, 0.074 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(3,5-bis-trifluoromethyl-benzenesulfonyl)-phenyl]-6-fluoro-3-methyl-naphthalen-2-yl}-acetic acid (0.035 g, 84%) as a solid. $^1$H NMR (400 MHz, DMSO-d$_6$) δ ppm 12.47 (br. s., 1 H) 8.71 (s, 2 H) 8.58 (s, 1 H) 8.34 (d, J=7.82 Hz, 2 H) 8.00 (dd, J=8.60, 6.20 Hz, 1 H) 7.90 (s, 1 H) 7.56 (d, J=7.82 Hz, 2 H) 7.37 (br. t, J=8.80, 8.80 Hz, 1 H) 6.64 (d, J=10.27 Hz, 1 H) 3.83 (s, 2 H) 2.03 (s, 3 H) MS calcd. for $C_{27}H_{16}F_7O_4S$ [(M−H)$^-$] 569, obsd. 569.0.

Example 13

{4-[4-(3,5-Dichloro-benzenesulfonyl)-phenyl]-6-fluoro-3-methyl-naphthalen-2-yl}-acetic acid

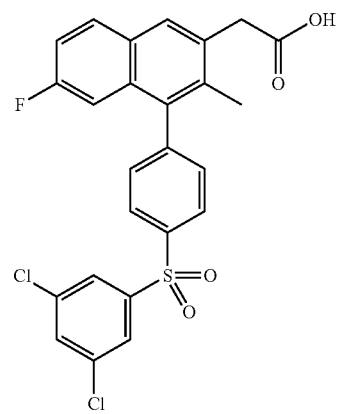

{4-[4-(3,5-Dichloro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-3,5-dichlorobenzene (0.2 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(3,5-dichloro-phenylsulfanyl)-phenyl]-6-fluoro-3-methyl-naphthalen-2-yl}-acetic acid methyl ester (0.083 g, 31%) as a solid.

{4-[4-(3,5-Dichloro-benzenesulfonyl)-phenyl]-6-fluoro-3-methyl-naphthalen-2-yl}-acetic acid methyl ester m-Chloroperoxybenzoic acid (0.15 g, approx. 0.85 mmol) was added to a stirred solution of {4-[4-(3,5-dichloro-phenylsulfanyl)-phenyl]-6-fluoro-3-methyl-naphthalen-2-yl}-acetic acid methyl ester (0.083 g, 0.17 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(3,5-dichlorobenzenesulfonyl)-phenyl]-6-fluoro-3-methyl-naphthalen-2-yl}-acetic acid methyl ester (0.039 g, 44%) as a solid.

{4-[4-(3,5-Dichloro-benzenesulfonyl)-phenyl]-6-fluoro-3-methyl-naphthalen-2-yl}-acetic acid Lithium hydroxide monohydrate (0.013 g, 0.30 mmol) was added to a stirred solution of {4-[4-(3,5-dichlorobenzenesulfonyl)-phenyl]-6-fluoro-3-methyl-naphthalen-2-yl}-acetic acid methyl ester (0.039 g, 0.075 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(3,5-dichlorobenzenesulfonyl)-phenyl]-6-fluoro-3-methyl-naphthalen-2-yl}-acetic acid (0.026 g, 69%) as a solid. $^1$H NMR (400 MHz, DMSO-d$_6$) δ ppm 12.48 (br. s, 1 H) 8.25 (d, J=8.31 Hz, 2 H) 8.15 (s, 2 H) 8.07 (s, 1 H) 8.00 (dd, J=8.80, 6.20 Hz, 1H) 7.90 (s, 1 H) 7.55 (d, J=8.31 Hz, 2 H) 7.38 (t, J=9.00 Hz, 1 H) 6.66 (d, J=11.74 Hz, 1 H) 3.83 (s, 2 H) 2.04 (s, 3 H). MS calcd. for C$_{25}$H$_{16}$Cl$_2$FO$_4$S [(M−H)$^−$] 501, obsd. 501.0.

Example 14

{4-[4-(3,5-Difluoro-benzenesulfonyl)-phenyl]-6-fluoro-3-methyl-naphthalen-2-yl}-acetic acid

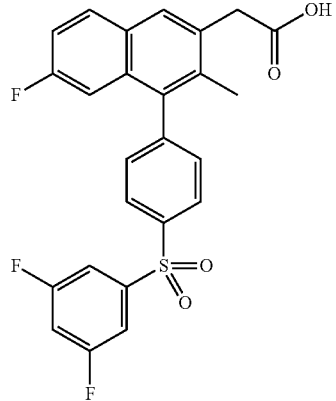 [SMILES: Cc1c(CC(=O)O)cc2ccc(F)cc2c1-c1ccc(S(=O)(=O)c2cc(F)cc(F)c2)cc1]

{4-[4-(3,5-Difluoro-phenylsulfanyl)-phenyl]-6-fluoro-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.2 g, 0.55 mmol) in dimethoxyethane (5 mL) was purged with argon for 5 minutes at room temperature. Tetrakis(triphenylphosphine)palladium(0) (0.032 g, 0.028 mmol), impure 1-(4-bromo-phenylsulfanyl)-3,5-difluorobenzene (0.184 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {4-[4-(3,5-difluoro-phenylsulfanyl)-phenyl]-6-fluoro-3-methyl-naphthalen-2-yl}-acetic acid methyl ester (0.09 g, 36%) as a solid. MS calcd. for C$_{26}$H$_{18}$F$_3$O$_2$S [(M−H)$^−$] 451, obsd. 451.2.

{4-[4-(3,5-Difluoro-benzenesulfonyl)-phenyl]-6-fluoro-3-methyl-naphthalen-2-yl}-acetic acid methyl ester m-Chloroperoxybenzoic acid (0.17 g, approx. 0.99 mmol) was added to a stirred solution of {4-[4-(3,5-difluoro-phenylsulfanyl)-phenyl]-6-fluoro-3-methyl-naphthalen-2-yl}-acetic acid methyl ester (0.09 g, 0.19 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(3,5-difluorobenzenesulfonyl)-phenyl]-6-fluoro-3-methyl-naphthalen-2-yl}-acetic acid methyl ester (0.055 g, 57%) as a solid.

{4-[4-(3,5-Difluoro-benzenesulfonyl)-phenyl]-6-fluoro-3-methyl-naphthalen-2-yl}-acetic acid Lithium hydroxide monohydrate (0.019 g, 0.45 mmol) was added to a stirred solution of {4-[4-(3,5-difluorobenzenesulfonyl)-phenyl]-6-fluoro-3-methyl-naphthalen-2-yl}-acetic acid methyl ester (0.055 g, 0.11 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(3,5-difluorobenzenesulfonyl)-phenyl]-6-fluoro-3-methyl-naphthalen-2-yl}-acetic acid (0.051 g, 96%) as a solid. $^1$H NMR (400 MHz, DMSO-d$_6$) δ ppm 12.48 (br. s., 1 H) 8.22 (d, J=7.82 Hz, 2 H) 7.97-8.05 (m, 1 H) 7.87-7.92 (m, 3 H) 7.74 (t, J=9.29 Hz, 1 H) 7.55 (d, J=7.82 Hz, 2 H) 7.35-7.42 (m, 1 H) 6.66 (d, J=11.74 Hz, 1 H) 3.84 (s, 2 H) 2.03 (s, 3 H) MS calcd. for C$_{25}$H$_{16}$F$_3$O$_4$S [(M−H)$^−$] 469, obsd. 469.4.

Example 15

{6-Chloro-4-[4-(2-chloro-benzenesulfonyl)-phenyl]-3-methyl-naphthalen-2-yl}-acetic acid

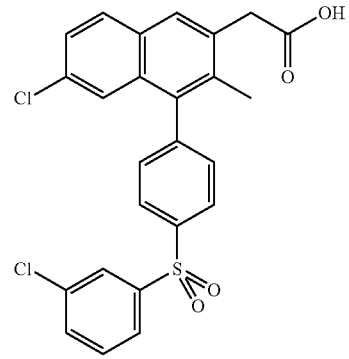 [SMILES: Cc1c(CC(=O)O)cc2ccc(Cl)cc2c1-c1ccc(S(=O)(=O)c2cccc(Cl)c2)cc1]

{6-Chloro-4-[4-(2-chloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-bromo-4-(2-chlorophenylsulfanyl)-benzene (0.165 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(2-chloro-phenylsulfanyl)-phenyl]-3-methyl-naphthalen-2-yl}-acetic acid methyl ester (0.051 g, 20%) as a solid. MS calcd. for $C_{26}H_{21}Cl_2O_2S$ $[(M+H)^+]$ 467, obsd. 467.3.

{6-Chloro-4-[4-(2-chloro-benzenesulfonyl)-phenyl]-3-methyl-naphthalen-2-yl}-acetic acid methyl ester m-Chloroperoxybenzoic acid (0.094 g, approx. 0.55 mmol) was added to a stirred solution of {6-chloro-4-[4-(2-chloro-phenylsulfanyl)-phenyl]-3-methyl-naphthalen-2-yl}-acetic acid methyl ester (0.051 g, 0.1 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(2-chloro-benzenesulfonyl)-phenyl]-3-methyl-naphthalen-2-yl}-acetic acid methyl ester (0.041 g, 75%) as a solid. MS calcd. for $C_{26}H_{21}Cl_2O_4S$ $[(M+H)^+]$ 499, obsd. 499.0.

{6-Chloro-4-[4-(2-chloro-benzenesulfonyl)-phenyl]-3-methyl-naphthalen-2-yl}-acetic acid Lithium hydroxide monohydrate (0.014 g, 0.32 mmol) was added to a stirred solution of {6-chloro-4-[4-(2-chloro-benzenesulfonyl)-phenyl]-3-methyl-naphthalen-2-yl}-acetic acid methyl ester (0.041 g, 0.082 mmol) in a 3:1 THF—$H_2O$ mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(2-chloro-benzenesulfonyl)-phenyl]-3-methyl-naphthalen-2-yl}-acetic acid (0.031 g, 78%) as a solid. $^1$H NMR (400 MHz, DMSO-$d_6$) δ ppm 12.49 (br. s., 1 H), 8.39 (d, J=7.82 Hz, 1 H), 8.09 (d, J=7.82 Hz, 2 H), 7.97 (d, J=8.80 Hz, 1 H), 7.91 (s, 1 H), 7.68-7.84 (m, 3 H), 7.54 (d, J=7.82 Hz, 2 H), 7.49 (d, J=8.80 Hz, 1 H), 6.95 (s, 1 H), 3.85 (s, 2H), 2.05 (s, 3 H). MS calcd. for $C_{25}H_{17}Cl_2O_4S$ [(M−H)] 483, obsd. 483.4.

Example 16

{6-Chloro-4-[4-(,3-chloro-benzenesulfonyl)-phenyl]-3-methyl-naphthalen-2-yl acetic acid

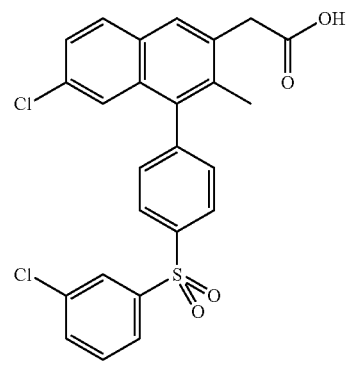 [SMILES: Cc1c(CC(=O)O)cc2ccc(Cl)cc2c1-c1ccc(S(=O)(=O)c2cccc(Cl)c2)cc1]

{6-Chloro-4-[4-(3-chloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-bromo-4-(3-chlorophenylsulfanyl)-benzene (0.159 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(3-chloro-phenylsulfanyl)-phenyl]-3-methyl-naphthalen-2-yl}-acetic acid methyl ester (0.065 g, 26%) as a solid.

{6-Chloro-4-[4-(3-chloro-benzenesulfonyl)-phenyl]-3-methyl-naphthalen-2-yl acetic acid methyl ester m-Chloroperoxybenzoic acid (0.119 g, approx. 0.69 mmol) was added to a stirred solution of {6-chloro-4-[4-(3-chloro-phenylsulfanyl)-phenyl]-3-methyl-naphthalen-2-yl}-acetic acid methyl ester (0.065 g, 0.14 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(3-chloro-benzenesulfonyl)-phenyl]-3-methyl-naphthalen-2-yl acetic acid methyl ester (0.02 g, 29%) as a solid. MS calcd. for $C_{26}H_{19}Cl_2O_4S$ $[(M-H)^-]$ 497, obsd. 497.3.

{6-Chloro-4-[4-(3-chloro-benzenesulfonyl)-phenyl]-3-methyl-naphthalen-2-yl acetic acid Lithium hydroxide monohydrate (0.007 g, 0.16 mmol) was added to a stirred solution of {6-chloro-4-[4-(3-chloro-benzenesulfonyl)-phenyl]-3-methyl-naphthalen-2-yl acetic acid methyl ester (0.020 g, 0.04 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(3-chloro-benzenesulfonyl)-phenyl]-3-methyl-naphthalen-2-yl acetic acid (0.018 g, 93%) as a solid. $^1$H NMR (400 MHz, DMSO-d$_6$) δ ppm 12.48 (br. s, 1 H) 8.20 (d, J=7.82 Hz, 2 H) 8.14 (s, 1 H) 8.06 (d, J=6.85 Hz, 1 H) 7.97 (d, J=8.80 Hz, 1 H) 7.91 (s, 1 H) 7.85 (d, J=8.20 Hz, 1 H) 7.73 (t, J=7.80 Hz, 1 H) 7.55 (d, J=7.83 Hz, 2 H) 7.48 (d, J=8.80 Hz, 1 H) 6.95 (s, 1 H) 3.84 (s, 2 H) 2.02 (s, 3 H) MS calcd. for C$_{25}$H$_{17}$Cl$_2$O$_4$S [(M–H)$^-$] 483, obsd. 482.3.

Example 17

{6-Chloro-4-[4-(4-chloro-benzenesulfonyl)-phenyl]-3-methyl-naphthalen-2-yl}-acetic acid

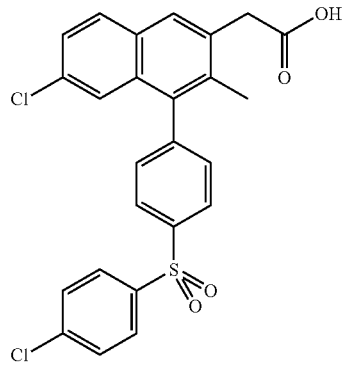 [SMILES: Cc1c(CC(=O)O)cc2ccc(Cl)cc2c1-c1ccc(S(=O)(=O)c2ccc(Cl)cc2)cc1]

{6-Chloro-4-[4-(4-chloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-bromo-4-(4-chlorophenylsulfanyl)-benzene (0.24 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(4-chloro-phenylsulfanyl)-phenyl]-3-methyl-naphthalen-2-yl}-acetic acid methyl ester (0.089 g, 34%) as a solid.

{6-Chloro-4-[4-(4-chloro-benzenesulfonyl)-phenyl]-3-methyl-naphthalen-2-yl}-acetic acid methyl ester m-Chloroperoxybenzoic acid (0.164 g, approx. 0.95 mmol) was added to a stirred solution of {6-chloro-4-[4-(4-chloro-phenylsulfanyl)-phenyl]-3-methyl-naphthalen-2-yl}-acetic acid methyl ester (0.089 g, 0.19 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(4-chloro-benzenesulfonyl)-phenyl]-3-methyl-naphthalen-2-yl}-acetic acid methyl ester (0.043 g, 45%) as a solid. MS calcd. for C$_{26}$H$_{19}$Cl$_2$O$_4$S [(M–H)$^-$] 497, obsd. 496.9.

{6-Chloro-4-[4-(4-chloro-benzenesulfonyl)-phenyl]-3-methyl-naphthalen-2-yl}-acetic acid Lithium hydroxide monohydrate (0.015 g, 0.35 mmol) was added to a stirred solution of {6-chloro-4-[4-(4-chloro-benzenesulfonyl)-phenyl]-3-methyl-naphthalen-2-yl}-acetic acid methyl ester (0.043 g, 0.086 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(4-chloro-benzenesulfonyl)-phenyl]-3-methyl-naphthalen-2-yl}-acetic acid (0.039 g, 93%) as a solid. $^1$H NMR (400 MHz, DMSO-d$_6$) δ ppm 12.50 (br. s., 1 H) 8.15 (d, J=7.82 Hz, 2 H) 8.10 (d, J=7.82 Hz, 2 H) 7.97 (d, J=8.80 Hz, 1 H) 7.91 (s, 1 H) 7.77 (d, J=7.82 Hz, 2 H) 7.54 (d, J=7.82 Hz, 2 H) 7.48 (d, J=8.80 Hz, 1 H) 6.95 (s, 1 H) 3.84 (s, 2 H) 2.01 (s, 3 H) MS calcd. for C$_{25}$H$_{17}$Cl$_2$O$_4$S [(M–H)$^-$] 483, obsd. 482.8.

Example 18

{6-Chloro-3-methyl-4-[4-(2-trifluoromethyl-benzenesulfonyl)-phenyl]-naphthalen-2-yl}-acetic acid

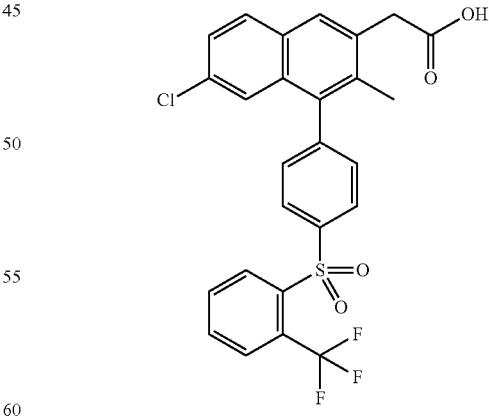

{6-Chloro-3-methyl-4-[4-(2-trifluoromethyl-phenylsulfanyl)-phenyl]-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.25 g, 0.67 mmol) in dimethoxyethane (5 mL) was purged with argon for 5 minutes at room temperature. Tetrakis(triphenylphosphine)palladium(0) (0.038 g, 0.033 mmol), crude 1-bromo-4-(2-(trifluoromethyl)phenylsulfanyl)-benzene (0.27 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-3-methyl-4-[4-(2-trifluoromethyl-phenylsulfanyl)-phenyl]-naphthalen-2-yl}-acetic acid methyl ester (0.045 g, 16%) as a solid.

{6-Chloro-3-methyl-4-[4-(2-trifluoromethyl-benzenesulfonyl)-phenyl]-naphthalen-2-yl}-acetic acid methyl ester m-Chloroperoxybenzoic acid (0.077 g, approx. 0.45 mmol) was added to a stirred solution of {6-chloro-3-methyl-4-[4-(2-trifluoromethyl-phenylsulfanyl)-phenyl]-naphthalen-2-yl}-acetic acid methyl ester (0.045 g, 0.09 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) provided {6-chloro-3-methyl-4-[4-(2-trifluoromethyl-benzenesulfonyl)-phenyl]-naphthalen-2-yl}-acetic acid methyl ester (0.039 g, 82%) as a solid. MS calcd. for $C_{27}H_{21}ClF_3O_4S$ [(M+H)$^+$] 533, obsd. 533.3.

{6-Chloro-3-methyl-4-[4-(2-trifluoromethyl-benzenesulfonyl)-phenyl]-naphthalen-2-yl}-acetic acid Lithium hydroxide monohydrate (0.013 g, 0.29 mmol) was added to a stirred solution of {6-chloro-3-methyl-4-[4-(2-trifluoromethyl-benzenesulfonyl)-phenyl]-naphthalen-2-yl}-acetic acid methyl ester (0.039 g, 0.073 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes gave {6-chloro-3-methyl-4-[4-(2-trifluoromethyl-benzenesulfonyl)-phenyl]-naphthalen-2-yl}-acetic acid (0.035 g, 92%) as a solid. $^1$H NMR (400 MHz, DMSO-d$_6$) δ ppm 12.49 (br. s, 1 H) 8.58 (d, J=6.85 Hz, 1 H) 7.93-8.13 (m, 6 H) 7.91 (s, 1 H) 7.53 (d, J=8.80 Hz, 2 H) 7.48 (d, J=8.80 Hz, 1 H) 6.93 (s, 1 H) 3.85 (s, 2 H) 2.03 (s, 3 H) MS calcd. for $C_{26}H_{17}ClF_3O_4S$ [(M–H)$^-$] 517, obsd. 517.3.

Example 19

{6-Chloro-3-methyl-4-[4-(2-trifluoromethoxy-benzenesulfonyl)-phenyl]-naphthalen-2-yl}-acetic acid

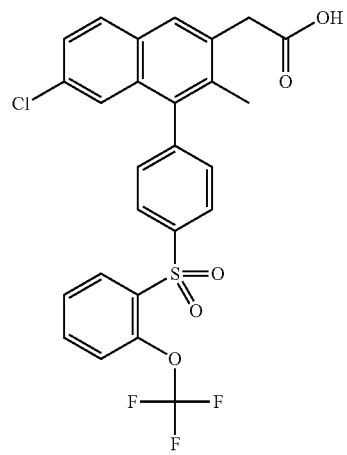 [SMILES: Cc1c(CC(=O)O)cc2ccc(Cl)cc2c1-c1ccc(S(=O)(=O)c2ccccc2OC(F)(F)F)cc1]

{6-Chloro-3-methyl-4-[4-(2-trifluoromethoxy-phenylsulfanyl)-phenyl]-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude1-bromo-4-(2-(trifluoro-methoxy)phenylsulfanyl)benzene (0.195 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to provide {6-chloro-3-methyl-4-[4-(2-trifluoromethoxyphenylsulfanyl)-phenyl]-naphthalen-2-yl}-acetic acid methyl ester (0.043 g, 15%) as a solid. MS calcd. for $C_{27}H_{21}ClF_3O_3S$ [(M+H)$^+$] 517, obsd. 517.2.

{6-Chloro-3-methyl-4-[4-(2-trifluoromethoxy-benzenesulfonyl)-phenyl]-naphthalen-2-yl}-acetic acid methyl ester m-Chloroperoxybenzoic acid (0.072 g, approx. 0.41 mmol) was added to a stirred solution of {6-chloro-3-methyl-4-[4-(2-trifluoromethoxy-phenylsulfanyl)-phenyl]-naphthalen-2-yl}-acetic acid methyl ester (0.043 g, 0.083 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-3-methyl-4-[4-(2-trifluoromethoxy-benzenesulfonyl)-phenyl]-naphthalen-2-yl}-acetic acid methyl ester (0.032 g, 70%) as a solid. MS calcd. for $C_{27}H_{21}ClF_3O_5S$ [(M+H)$^+$] 549, obsd. 548.9.

{6-Chloro-3-methyl-4-[4-(2-trifluoromethoxy-benzenesulfonyl)-phenyl]-naphthalen-2-yl}-acetic acid Lithium hydroxide monohydrate (0.01 g, 0.23 mmol) was added to a stirred solution of {6-chloro-3-methyl-4-[4-(2-trifluoromethoxy-benzenesulfonyl)-phenyl]-naphthalen-2-yl}-acetic acid methyl ester (0.032 g, 0.058 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-3-methyl-4-[4-(2-trifluoromethoxy-benzenesulfonyl)-phenyl]-naphthalen-2-yl}-acetic acid (0.035 g, 92%) as a solid. $^1$H NMR (400 MHz, DMSO-d$_6$) δ ppm 12.50 (br. s, 1 H) 8.36 (d, J=7.82 Hz, 1 H) 8.06 (d, J=8.80 Hz, 2 H) 7.88-7.99 (m, 3 H) 7.74 (t, J=7.80 Hz, 1 H) 7.62 (d, J=8.10 Hz, 1 H) 7.55 (d, J=7.83 Hz, 2 H) 7.48 (d, J=7.82 Hz, 1 H) 6.94 (s, 1 H) 3.84 (s, 2 H) 2.05 (s, 3 H) MS calcd. for C$_{26}$H$_{19}$ClF$_3$O$_5$S [(M+H)$^+$] 535, obsd. 535.3.

Example 20

{6-Chloro-3-methyl-4-[4-(4-trifluoromethoxy-benzenesulfonyl)-phenyl]-naphthalen-2-yl}-acetic acid

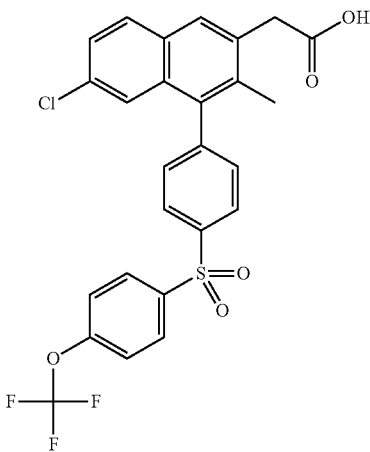 [SMILES: Cc1c(CC(=O)O)cc2ccc(Cl)cc2c1-c1ccc(S(=O)(=O)c2ccc(OC(F)(F)F)cc2)cc1]

{6-Chloro-3-methyl-4-[4-(4-trifluoromethoxy-phenylsulfanyl)-phenyl]-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-bromo-4-(4-(trifluoro-methoxy)phenylsulfanyl)benzene (0.334 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to obtain {6-chloro-3-methyl-4-[4-(4-trifluoromethoxyphenylsulfanyl)-phenyl]-naphthalen-2-yl}-acetic acid methyl ester (0.127 g, 44%) as a solid.

{6-Chloro-3-methyl-4-[4-(4-trifluoromethoxy-benzenesulfonyl)-phenyl]-naphthalen-2-yl}-acetic acid methyl ester m-Chloroperoxybenzoic acid (0.211 g, approx. 1.23 mmol) was added to a stirred solution of {6-chloro-3-methyl-4-[4-(2-trifluoromethoxy-phenylsulfanyl)-phenyl]-naphthalen-2-yl}-acetic acid methyl ester (0.127 g, 0.24 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-3-methyl-4-[4-(4-trifluoromethoxy-benzenesulfonyl)-phenyl]-naphthalen-2-yl}-acetic acid methyl ester (0.07 g, 52%) as a solid. MS calcd. for C$_{27}$H$_{19}$ClF$_3$O$_5$S [(M–H)$^-$] 547, obsd. 547.4.

{6-Chloro-3-methyl-4-[4-(4-trifluoromethoxy-benzenesulfonyl)-phenyl]-naphthalen-2-yl}-acetic acid Lithium hydroxide monohydrate (0.021 g, 0.50 mmol) was added to a stirred solution of {6-chloro-3-methyl-4-[4-(4-trifluoromethoxy-benzenesulfonyl)-phenyl]-naphthalen-2-yl}-acetic acid methyl ester (0.07 g, 0.13 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-3-methyl-4-[4-(4-trifluoromethoxy-benzenesulfonyl)-phenyl]-naphthalen-2-yl}-acetic acid (0.048 g, 70%) as a solid. $^1$H NMR (400 MHz, DMSO-d$_6$) δ ppm 12.49 (br. s., 1 H) 8.23 (d, J=8.80 Hz, 2 H) 8.17 (d, J=7.82 Hz, 2 H) 7.97 (d, J=8.80 Hz, 1 H) 7.91 (s, 1 H) 7.68 (d, J=7.82 Hz, 2 H) 7.55 (d, J=8.80 Hz, 2 H) 7.48 (d, J=7.82 Hz, 1 H) 6.94 (s, 1 H) 3.85 (s, 2 H) 2.02 (s, 3 H). MS calcd. for C$_{26}$H$_{17}$ClF$_3$O$_5$S [(M–H)$^-$] 533, obsd. 533.4.

Example 21

{6-Chloro-4-[4-(2,4-dichloro-benzenesulfonyl)-phenyl]-3-methyl-naphthalen-2-yl}-acetic acid

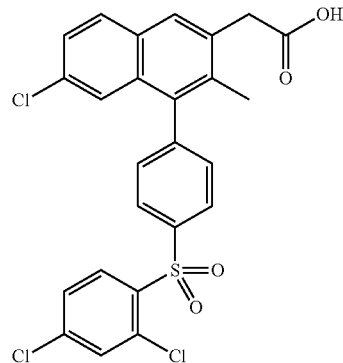 [SMILES: Cc1c(CC(=O)O)cc2ccc(Cl)cc2c1-c1ccc(S(=O)(=O)c2ccc(Cl)cc2Cl)cc1]

{6-Chloro-4-[4-(2,4-dichloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-(4-bromo-phenylsulfanyl)-2,4-dichlorobenzene (0.196 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(2,4-dichloro-phenylsulfanyl)-phenyl]-3-methyl-naphthalen-2-yl}-acetic acid methyl ester (0.10 g, 36%) as a solid.

{6-Chloro-4-[4-(2,4-dichloro-benzenesulfonyl)-phenyl]-3-methyl-naphthalen-2-yl}-acetic acid methyl ester m-Chloroperoxybenzoic acid (0.173 g, approx. 1.0 mmol) was added to a stirred solution of {6-chloro-4-[4-(2,4-dichloro-phenylsulfanyl)-phenyl]-3-methyl-naphthalen-2-yl}-acetic acid methyl ester (0.1 g, 0.2 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(2,4-dichloro-benzenesulfonyl)-phenyl]-3-methyl-naphthalen-2-yl}-acetic acid methyl ester (0.04 g, 37%) as a solid. MS calcd. for $C_{26}H_{18}Cl_3O_4S$ [(M–H)$^-$] 531, obsd. 531.2.

{6-Chloro-4-[4-(2,4-dichloro-benzenesulfonyl)-phenyl]-3-methyl-naphthalen-2-yl}-acetic acid Lithium hydroxide monohydrate (0.013 g, 0.30 mmol) was added to a stirred solution of {6-chloro-4-[4-(2,4-dichloro-benzenesulfonyl)-phenyl]-3-methyl-naphthalen-2-yl}-acetic acid (0.04 g, 0.07 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(2,4-dichloro-benzenesulfonyl)-phenyl]-3-methyl-naphthalen-2-yl}-acetic acid (0.035 g, 90%) as a solid. $^1$H NMR (400 MHz, DMSO-d$_6$) δ ppm 12.46 (br. s, 1 H) 8.38 (d, J=8.80 Hz, 1 H) 8.10 (d, J=7.82 Hz, 2 H) 7.94-8.00 (m, 2 H) 7.91 (s, 1 H) 7.83 (d, J=8.80 Hz, 1 H) 7.55 (d, J=7.83 Hz, 2 H) 7.49 (d, J=8.80 Hz, 1 H) 6.96 (s, 1 H) 3.86 (s, 2 H) 2.04 (s, 3 H). MS calcd. for $C_{25}H_{16}Cl_3O_4S$ [(M–H)$^-$] 517, obsd. 517.2.

Example 22

{6-Chloro-4-[4-(2,5-dichloro-benzenesulfonyl)-phenyl]-3-methyl-naphthalen-2-yl}-acetic acid

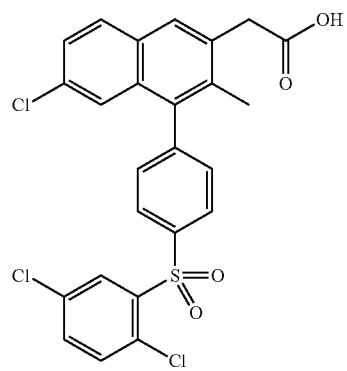 [SMILES: Cc1c(CC(=O)O)cc2ccc(Cl)cc2c1-c1ccc(S(=O)(=O)c2cc(Cl)ccc2Cl)cc1]

{6-Chloro-4-[4-(2,5-dichloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-(4-bromo-phenylsulfanyl)-2,5-dichlorobenzene (0.334 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(2,5-dichloro-phenylsulfanyl)-phenyl]-3-methyl-naphthalen-2-yl}-acetic acid methyl ester (0.076 g, 28%) as a solid.

{6-Chloro-4-[4-(2,5-dichloro-benzenesulfonyl)-phenyl]-3-methyl-naphthalen-2-yl}-acetic acid methyl ester m-Chloroperoxybenzoic acid (0.13 g, approx. 0.76 mmol) was added to a stirred solution of {6-chloro-4-[4-(2,5-dichloro-phenylsulfanyl)-phenyl]-3-methyl-naphthalen-2-yl}-acetic acid methyl ester (0.076 g, 0.15 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(2,5-dichloro-benzenesulfonyl)-phenyl]-3-methyl-naphthalen-2-yl}-acetic acid methyl ester (0.037 g, 46%) as a solid. MS calcd. for $C_{26}H_{20}Cl_3O_4S$ [(M+H)$^+$] 533, obsd. 533.4.

{6-Chloro-4-[4-(2,5-dichloro-benzenesulfonyl)-phenyl]-3-methyl-naphthalen-2-yl}-acetic acid Lithium hydroxide monohydrate (0.012 g, 0.27 mmol) was added to a stirred solution of {6-chloro-4-[4-(2,5-dichloro-benzenesulfonyl)-phenyl]-3-methyl-naphthalen-2-yl}-acetic acid methyl ester (0.037 g, 0.06 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] through the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(2,5-dichloro-benzenesulfonyl)-phenyl]-3-methyl-naphthalen-2-yl}-acetic acid (0.031 g, 86%) as a solid. $^1$H NMR (400 MHz, DMSO-d$_6$) δ ppm 12.52 (br. s, 1 H) 8.33 (s, 1 H) 8.16 (d, J=7.82 Hz, 2 H) 7.99 (s, 1 H) 7.85-7.93 (m, 2 H) 7.77 (d, J=8.80 Hz, 1 H) 7.55 (d, J=8.80 Hz, 2 H) 7.49 (d, J=8.80 Hz, 1 H) 6.95 (s, 1 H) 3.86 (s, 2 H) 2.05 (s, 3 H) MS calcd. for C$_{25}$H$_{16}$Cl$_3$O$_4$S [(M−H)$^−$] 517, obsd. 517.3.

Example 23

{6-Chloro-4-[4-(2,4-difluoro-benzenesulfonyl)-phenyl]-3-methyl-naphthalen-2-yl}-acetic acid

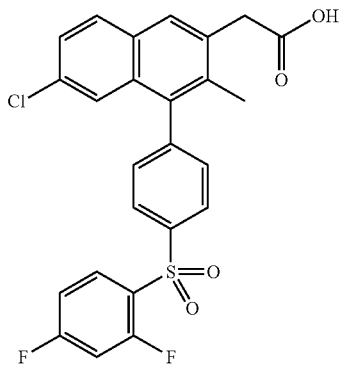 [SMILES: Cc1c(CC(=O)O)cc2ccc(Cl)cc2c1-c1ccc(S(=O)(=O)c2ccc(F)cc2F)cc1]

{6-Chloro-4-[4-(2,4-difluoro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-(4-bromo-phenylsulfanyl)-2,4-difluorobenzene (0.176 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(2,4-difluoro-phenylsulfanyl)-phenyl]-3-methyl-naphthalen-2-yl}-acetic acid methyl ester (0.04 g, 16%) as a solid.

{6-Chloro-4-[4-(2,4-difluoro-benzenesulfonyl)-phenyl]-3-methyl-naphthalen-2-yl}-acetic acid methyl ester m-Chloroperoxybenzoic acid (0.074 g, approx. 0.42 mmol) was added to a stirred solution {6-chloro-4-[4-(2,4-difluoro-phenylsulfanyl)-phenyl]-3-methyl-naphthalen-2-yl}-acetic acid methyl ester (0.04 g, 0.08 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(2,4-difluoro-benzenesulfonyl)-phenyl]-3-methyl-naphthalen-2-yl}-acetic acid methyl ester (0.032 g, 75%) as a solid. MS calcd. for C$_{26}$H$_{18}$ClF$_2$O$_4$S [(M−H)$^−$] 499, obsd. 499.1.

{6-Chloro-4-[4-(2,4-difluoro-benzenesulfonyl)-phenyl]-3-methyl-naphthalen-2-yl}-acetic acid Lithium hydroxide monohydrate (0.01 g, 0.26 mmol) was added to a stirred solution of {6-chloro-4-[4-(2,4-difluoro-benzenesulfonyl)-phenyl]-3-methyl-naphthalen-2-yl}-acetic acid methyl ester (0.032 g, 0.064 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(2,4-difluoro-benzenesulfonyl)-phenyl]-3-methyl-naphthalen-2-yl}-acetic acid (0.031 g, 100%) as a solid. $^1$H NMR (400 MHz, DMSO-d$_6$) δ ppm 12.50 (br. s, 1 H) 8.19-8.28 (m, 1 H) 8.13 (d, J=7.82 Hz, 2 H) 7.97 (d, J=8.80 Hz, 1 H) 7.92 (s, 1 H) 7.60-7.68 (m, 1 H) 7.57 (d, J=7.82 Hz, 2 H) 7.41-7.52 (m, 2 H) 6.96 (s, 1 H) 3.85 (s, 2 H) 2.03 (s, 3 H) MS calcd. for C$_{25}$H$_{16}$ClF$_2$O$_4$S [(M−H)$^−$] 485, obsd. 485.3.

Example 24

{6-Chloro-4-[4-(2,6-difluoro-benzenesulfonyl)-phenyl]-3-methyl-naphthalen-2-yl}-acetic acid

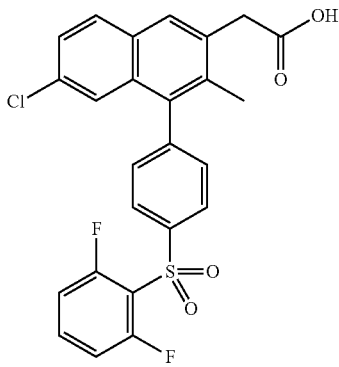 [SMILES: Cc1c(CC(=O)O)cc2ccc(Cl)cc2c1-c1ccc(S(=O)(=O)c2c(F)cccc2F)cc1]

{6-Chloro-4-[4-(2,6-difluoro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.18 g, 0.48 mmol) in dimethoxyethane (4 mL) was purged with argon for 5 minutes at room temperature. Tetrakis(triphenylphosphine)palladium(0) (0.055 g, 0.048 mmol), crude 1-(4-bromo-phenylsulfanyl)-2,6-difluorobenzene (0.14 g) and 2.0 M aqueous sodium carbonate (1 mL, 2 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(2,6-difluoro-phenylsulfanyl)-phenyl]-3-methyl-naphthalen-2-yl}-acetic acid methyl ester (0.035 g, 13%) as a solid.

{6-Chloro-4-[4-(2,6-difluoro-benzenesulfonyl)-phenyl]-3-methyl-naphthalen-2-yl}-acetic acid methyl ester m-Chloroperoxybenzoic acid (0.064 g, approx. 0.37 mmol) was added to a stirred solution of {6-chloro-4-[4-(2,6-difluoro-phenylsulfanyl)-phenyl]-3-methyl-naphthalen-2-yl}-acetic acid methyl ester (0.035 g, 0.074 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(2,6-difluoro-benzenesulfonyl)-phenyl]-3-methyl-naphthalen-2-yl}-acetic acid methyl ester (0.032 g, 87%) as a solid.

{6-Chloro-4-[4-(2,6-difluoro-benzenesulfonyl)-phenyl]-3-methyl-naphthalen-2-yl}-acetic acid Lithium hydroxide monohydrate (0.01 g, 0.26 mmol) was added to a stirred solution of {6-chloro-4-[4-(2,6-difluoro-benzenesulfonyl)-phenyl]-3-methyl-naphthalen-2-yl}-acetic acid methyl ester (0.032 g, 0.064 mmol) in a 3:1 THF—H$_2$O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(2,6-difluoro-benzenesulfonyl)-phenyl]-3-methyl-naphthalen-2-yl}-acetic acid (0.029 g, 93%) as a solid. $^1$H NMR (400 MHz, DMSO-d$_6$) δ ppm 12.43 (br. s, 1 H) 8.18 (d, J=7.83 Hz, 2 H) 7.98 (d, J=8.30 Hz, 1 H) 7.92 (s, 1 H) 7.81-7.89 (m, 1 H) 7.59 (d, J=7.82 Hz, 2 H) 7.49 (dd, J=8.80, 1.90 Hz, 1 H) 7.35-7.44 (m, 2 H) 6.97 (s, 1 H) 3.85 (s, 2 H) 2.04 (s, 3 H). MS calcd. for C$_{25}$H$_{16}$ClF$_2$O$_4$S [(M–H)$^-$] 485, obsd. 485.2.

Example 25

{4-[4-(3,5-Bis-trifluoromethyl-benzenesulfonyl)-phenyl]-6-chloro-3-methyl-naphthalen-2-yl}-acetic acid

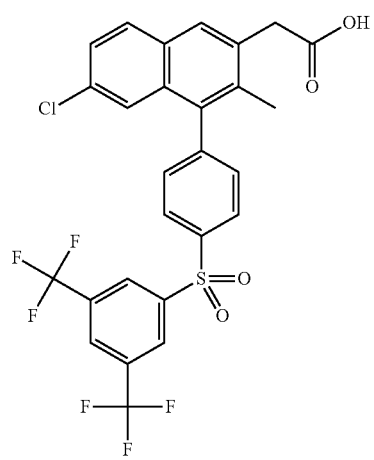 [SMILES: Cc1c(CC(=O)O)cc2ccc(Cl)cc2c1-c1ccc(S(=O)(=O)c2cc(C(F)(F)F)cc(C(F)(F)F)c2)cc1]

{4-[4-(3,5-Bis-trifluoromethyl-phenylsulfanyl)-phenyl]-6-chloro-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-(4-bromo-phenylsulfanyl)-3,5-bis-trifluoromethyl-benzene (0.334 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to provide {4-[4-(3,5-bis-trifluoromethyl-phenylsulfanyl)-phenyl]-6-chloro-3-methyl-naphthalen-2-yl}-acetic acid methyl ester (0.083 g, 27%) as a solid.

{4-[4-(3,5-Bis-trifluoromethyl-benzenesulfonyl)-phenyl]-6-chloro-3-methyl-naphthalen-2-yl}-acetic acid methyl ester m-Chloroperoxybenzoic acid (0.064 g, approx. 0.37 mmol) was added to a stirred solution of {4-[4-(2,6-difluoro-phenylsulfanyl)-phenyl]-6-chloro-3-methyl-naphthalen-2-yl}-acetic acid methyl ester (0.083 g, 0.146 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {4-[4-(3,5-bis-trifluoromethyl-benzenesulfonyl)-phenyl]-6-chloro-3-methyl-naphthalen-2-yl}-acetic acid methyl ester (0.038 g, 44%) as a solid. MS calcd. for $C_{28}H_{18}ClF_6O_4S$ [(M−H)⁻] 599, obsd. 599.2.

{4-[4-(3,5-Bis-trifluoromethyl-benzenesulfonyl)-phenyl]-6-chloro-3-methyl-naphthalen-2-yl}-acetic acid Lithium hydroxide monohydrate (0.011 g, 0.26 mmol) was added to a stirred solution of {4-[4-(3,5-bis-trifluoromethyl-benzenesulfonyl)-phenyl]-6-chloro-3-methyl-naphthalen-2-yl}-acetic acid methyl ester (0.038 g, 0.063 mmol) in a 3:1 THF—H₂O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {4-[4-(3,5-bis-trifluoromethyl-benzenesulfonyl)-phenyl]-6-chloro-3-methyl-naphthalen-2-yl}-acetic acid (0.031 g, 84%) as a solid. ¹H NMR (400 MHz, DMSO-d₆) δ ppm 12.49 (br. s, 1 H) 8.71 (s, 2 H) 8.59 (s, 1 H) 8.35 (d, J=7.82 Hz, 2 H) 7.97 (d, J=8.40 Hz, 1 H) 7.91 (s, 1 H) 7.58 (d, J=7.82 Hz, 2 H) 7.48 (d, J=8.60 Hz, 1 H) 6.95 (s, 1 H) 3.84 (s, 2 H) 2.03 (s, 3 H). MS calcd. for $C_{27}H_{16}ClF_6O_4S$ [(M−H)⁻] 585, obsd. 585.3.

Example 26

{6-Chloro-4-[4-(3,5-dichloro-benzenesulfonyl)-phenyl]-3-methyl-naphthalen-2-yl}-acetic acid

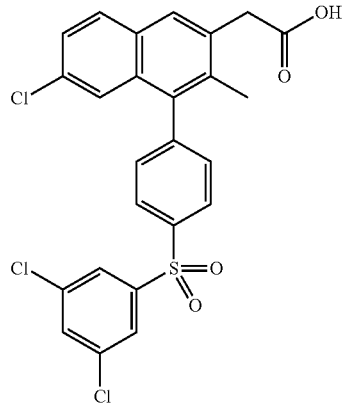 [SMILES: Cc1c(CC(=O)O)cc2ccc(Cl)cc2c1-c1ccc(S(=O)(=O)c2cc(Cl)cc(Cl)c2)cc1]

{6-Chloro-4-[4-(3,5-dichloro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)-palladium(0) (0.031 g, 0.027 mmol), crude 1-(4-bromo-phenylsulfanyl)-3,5-dichlorobenzene (0.195 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(3,5-dichloro-phenylsulfanyl)-phenyl]-3-methyl-naphthalen-2-yl}-acetic acid methyl ester (0.117 g, 42%) as a solid.

{6-Chloro-4-[4-(3,5-dichloro-benzenesulfonyl)-phenyl]-3-methyl-naphthalen-2-yl}-acetic acid methyl ester m-Chloroperoxybenzoic acid (0.2 g, approx. 1.16 mmol) was added to a stirred solution of {4-[4-(3,5-dichloro-phenylsulfanyl)-phenyl]-6-chloro-3-methyl-naphthalen-2-yl}-acetic acid methyl ester (0.117 g, 0.23 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(3,5-dichloro-benzenesulfonyl)-phenyl]-3-methyl-naphthalen-2-yl}-acetic acid methyl ester (0.065 g, 52%) as a solid. MS calcd. for $C_{26}H_{20}Cl_3O_4S$ [(M+H)⁺] 533, obsd. 533.3.

{6-Chloro-4-[4-(3,5-dichloro-benzenesulfonyl)-phenyl]-3-methyl-naphthalen-2-yl}-acetic acid Lithium hydroxide monohydrate (0.020 g, 0.48 mmol) was added to a stirred solution of {6-chloro-4-[4-(3,5-dichloro-benzenesulfonyl)-phenyl]-3-methyl-naphthalen-2-yl}-acetic acid methyl ester (0.065 g, 0.122 mmol) in a 3:1 THF—H₂O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(3,5-dichloro-benzenesulfonyl)-phenyl]-3-methyl-naphthalen-2-yl}-acetic acid (0.058 g, 92%) as a solid. ¹H NMR (400 MHz, DMSO-d₆) δ ppm 12.48 (br. s, 1 H) 8.26 (d, J=8.80 Hz, 2H) 8.15 (s, 2 H) 8.05-8.08 (m, 1 H) 7.97 (d, J=8.80 Hz, 1 H) 7.91 (s, 1 H) 7.56 (d, J=8.80 Hz, 2 H) 7.48 (d, J=8.60 Hz, 1 H)

6.97 (s, 1 H) 3.84 (s, 2 H) 2.03 (s, 3H). MS calcd. for $C_{25}H_{16}Cl_3O_4S$ [(M–H)⁻] 517, obsd. 517.1.

Example 27

{6-Chloro-4-[4-(3,5-difluoro-benzenesulfonyl)-phenyl]-3-methyl-naphthalen-2-yl}-acetic acid

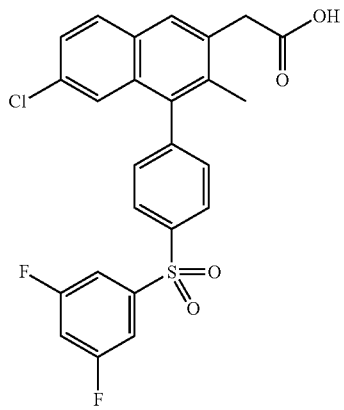 [SMILES: Cc1c(CC(=O)O)cc2ccc(Cl)cc2c1-c1ccc(S(=O)(=O)c2cc(F)cc(F)c2)cc1]

{6-Chloro-4-[4-(3,5-difluoro-phenylsulfanyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.2 g, 0.53 mmol) in dimethoxyethane (5 mL) was purged with argon for 5 minutes at room temperature. Tetrakis(triphenylphosphine)palladium(0) (0.031 g, 0.027 mmol), crude 1-(4-bromo-phenylsulfanyl)-3,5-difluorobenzene (0.176 g) and 1.0 M aqueous sodium bicarbonate (5 mL, 5 mmol) were added simultaneously to the reaction mixture under argon. The reaction mixture was refluxed for 2 hours and then brought to room temperature. Water was added and the resulting mixture was extracted twice with ethyl acetate. The combined organic extracts were washed with water and brine, dried over anhydrous sodium sulfate, and concentrated under reduced pressure to give the crude product, which was finally purified using flash chromatography (0-3% ethyl acetate in hexanes) to give {6-chloro-4-[4-(3,5-difluoro-phenylsulfanyl)-phenyl]-3-methyl-naphthalen-2-yl}-acetic acid methyl ester (0.14 g, 53%) as a solid. MS calcd. for $C_{26}H_{18}ClF_2O_2S$ [(M–H)⁻] 467, obsd. 467.2.

{6-Chloro-4-[4-(3,5-difluoro-benzenesulfonyl)-phenyl]-3-methyl-naphthalen-2-yl}-acetic acid methyl ester m-Chloroperoxybenzoic acid (2.62 g, approx. 1.49 mmol) was added to a stirred solution of {6-chloro-4-[4-(3,5-difluoro-phenylsulfanyl)-phenyl]-3-methyl-naphthalen-2-yl}-acetic acid methyl ester (0.14 g, 0.29 mmol) in dichloromethane (5 mL). The reaction mixture was stirred for 16 hours at room temperature. The reaction mixture was diluted with dichloromethane and washed with water followed by an aqueous solution of sodium sulfite. The organic phase was dried over anhydrous sodium sulfate and concentrated in vacuo to give the crude product. Flash chromatography (Biotage column, 5-10% ethyl acetate in hexanes) afforded {6-chloro-4-[4-(3,5-difluoro-benzenesulfonyl)-phenyl]-3-methyl-naphthalen-2-yl}-acetic acid methyl ester (0.057 g, 38%) as a solid. MS calcd. for $C_{26}H_{18}ClF_2O_4S$ [(M–H)⁻] 499, obsd. 499.2.

{6-Chloro-4-[4-(3,5-difluoro-benzenesulfonyl)-phenyl]-3-methyl-naphthalen-2-yl}-acetic acid Lithium hydroxide monohydrate (0.019 g, 0.46 mmol) was added to a stirred solution of {6-chloro-4-[4-(3,5-difluoro-benzenesulfonyl)-phenyl]-3-methyl-naphthalen-2-yl}-acetic acid methyl ester (0.057 g, 0.114 mmol) in a 3:1 THF—H₂O mixture (4 mL). The reaction mixture was stirred for 16 hours at room temperature. The THF was distilled off under reduced pressure, and the crude residue was diluted with water, acidified [pH~2] via the drop-wise addition of an aqueous solution of hydrochloric acid (6.0 N). The mixture was extracted twice with ethyl acetate. The combined organic layers were washed with water and brine, dried over anhydrous sodium sulfate and concentrated under reduced pressure to give the crude product. Trituration with hexanes afforded {6-chloro-4-[4-(3,5-difluoro-benzenesulfonyl)-phenyl]-3-methyl-naphthalen-2-yl}-acetic acid (0.043 g, 77%) as a solid. ¹H NMR (400 MHz, DMSO-d₆) δ ppm 12.51 (br. s, 1 H) 8.23 (d, J=7.82 Hz, 2 H) 7.97 (d, J=8.80 Hz, 1 H) 7.86-7.93 (m, 3 H) 7.70-7.78 (m, 1 H) 7.56 (d, J=8.80 Hz, 2 H) 7.48 (d, J=8.80 Hz, 1 H) 6.96 (s, 1 H) 3.85 (s, 2 H) 2.03 (s, 3 H) MS calcd. for $C_{25}H_{16}ClF_2O_4S$ [(M–H)⁻] 485, obsd. 485.2.

Example 28

{6-Chloro-4-[4-(4-fluoro-phenylsulfamoyl)-phenyl]-3-methyl-naphthalen-2-yl}-acetic acid

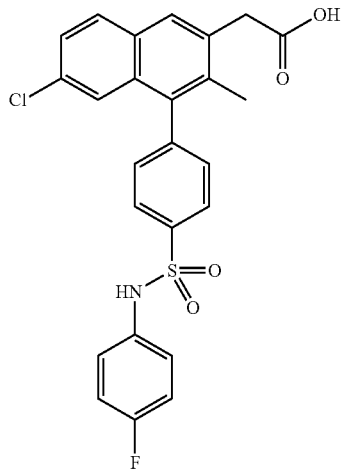 [SMILES: Cc1c(CC(=O)O)cc2ccc(Cl)cc2c1-c1ccc(S(=O)(=O)Nc2ccc(F)cc2)cc1]

{6-Chloro-4-[4-(4-fluoro-phenylsulfamoyl)-phenyl]-3-methyl-naphthalen-2-yl}-acetic acid methyl ester A stirred solution of (6-chloro-3-methyl-4-trifluoromethanesulfonyloxy-naphthalen-2-yl)-acetic acid methyl ester (0.15 g, 0.38 mmol) in dimethoxyethane (5 mL) was purged with argon for 5 minutes at room temperature. Triphenylphosphine (0.016 g, 0.06 mmol), palladium(II) acetate (0.009 g, 0.038 mmol), 4-(N-(4-fluorophenyl)sulfamoyl)-phenylboronic acid (0.15 g, 0.51 mmol) and a 2 M aqueous solution of sodium carbonate (0.6 mL, 1.2 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous Na$_2$SO$_4$ and concentrated under reduced pressure to give the crude product, which was finally purified using flash chromatography (Biotage, 5-10% ethyl acetate-hexane) to give {6-chloro-4-[4-(4-fluoro-phenylsulfamoyl)-phenyl]-3-methyl-naphthalen-2-yl}-acetic acid methyl ester (0.016 g, 8%) as a solid. MS calcd. for C$_{26}$H$_{20}$ClFNO$_4$S [(M−H)$^-$] 496, obsd. 496.2.

[6-Chloro-3-methyl-4-(4-p-tolylsulfamoyl-phenyl)-naphthalen-2-yl]-acetic acid

Lithium hydroxide monohydrate (0.012 g, 0.28 mmol) was added to a stirred solution of {6-chloro-4-[4-(4-fluoro-phenylsulfamoyl)-phenyl]-3-methyl-naphthalen-2-yl}-acetic acid methyl ester (0.035 g, 0.07 mmol) in a 3:1 mixture of THF—H$_2$O mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous Na$_2$SO$_4$, and concentrated under reduced pressure to give the crude product. Trituration with hexane afforded {6-chloro-4-[4-(4-fluoro-phenylsulfamoyl)-phenyl]-3-methyl-naphthalen-2-yl}-acetic acid (0.03 g, 88%) as a solid. $^1$H NMR (DMSO-d$_6$) δ: 12.50 (br. s, 1H), 10.25 (br. s, 1H), 7.75-8.06 (m, 5H), 7.32-7.56 (m, 3H), 7.13 (d, J=6.4 Hz, 4H), 6.81 (s, 1H), 3.84 (s, 3H), 2.01 (s, 3H). MS calcd. for C$_{25}$H$_{18}$ClFNO$_4$S [(M−H)$^-$] 482, obsd. 481.8.

Example 29

[6-Chloro-3-methyl-4-(4-p-tolylsulfamoyl-phenyl)-naphthalen-2-yl]-acetic acid

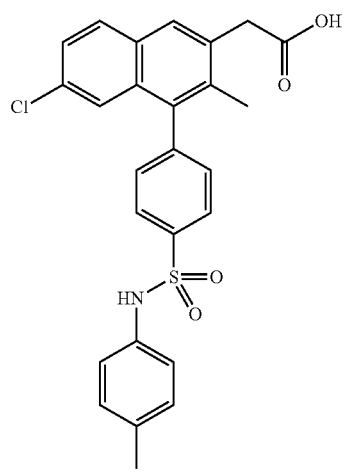 [SMILES: Cc1ccc(NS(=O)(=O)c2ccc(-c3c(C)c(CC(=O)O)cc4ccc(Cl)cc34)cc2)cc1]

[6-Chloro-3-methyl-4-(4-p-tolylsulfamoyl-phenyl)-naphthalen-2-yl]-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium(II) acetate (0.006 g, 0.027 mmol), 4-(N-p-tolylsulfamoyl)phenylsulfamoyl)phenylboronic acid (0.10 g, 0.34 mmol) and a 2 M aqueous solution of sodium carbonate (0.5 mL, 1.0 mmol) were added simultaneously to the reaction mixture at room temperature under argon. The reaction mixture was refluxed for 2 hours. The reaction was cooled to room temperature. Water was added and the mixture was extracted twice with ethyl acetate. The collected organic extracts were washed with water and then brine, dried over anhydrous Na$_2$SO$_4$ and concentrated under reduced pressure to give the crude product, which was finally purified using flash chromatography (Biotage, 5-10% ethyl acetate-hexane) to [6-chloro-3-methyl-4-(4-p-tolylsulfamoyl-phenyl)-naphthalen-2-yl]-acetic acid methyl ester (0.038 g, 30%) as a solid. MS calcd. for C$_{27}$H$_{23}$ClNO$_4$S [(M−H)$^-$] 492, obsd. 492.4.

[6-Chloro-3-methyl-4-(4-p-tolylsulfamoyl-phenyl)-naphthalen-2-yl]-acetic acid

Lithium hydroxide monohydrate (0.012 g, 0.28 mmol) was added to a stirred solution of [6-chloro-3-methyl-4-(4-p-tolylsulfamoyl-phenyl)-naphthalen-2-yl]-acetic acid methyl ester (0.035 g, 0.07 mmol) in a 3:1 mixture of THF—H$_2$O mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous Na$_2$SO$_4$, and concentrated under reduced pressure to give the crude product. Trituration with hexane afforded [6-chloro-3-methyl-4-(4-p-tolylsulfamoyl-phenyl)-naphthalen-2-yl]-acetic acid (0.03 g, 88%) as a solid. $^1$H NMR (DMSO-d$_6$) δ: 12.48 (br. s, 1H), 10.09 (s, 1H), 7.77-8.05 (m, 4H), 7.33-7.56 (m, 3H), 6.95-7.16 (m, 4H), 6.82 (s, 1H), 3.84 (s, 2H), 2.21 (s, 3H), 2.02 (s, 3H). MS calcd. for C$_{26}$H$_{21}$ClNO$_4$S [(M−H)$^-$] 478, obsd. 478.3.

Example 30

{6-Chloro-3-methyl-4-[4-(4-trifluoromethoxy-phenylsulfamoyl)-phenyl]-naphthalen-2-yl}-acetic acid

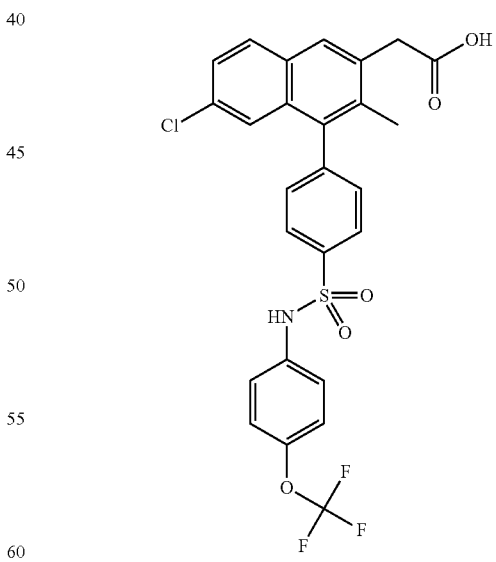

{6-Chloro-3-methyl-4-[4-(4-trifluoromethoxy-phenylsulfamoyl)-phenyl]-naphthalen-2-yl}-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 4-(N-(4-(trifluoromethoxy)phenyl)sulfamoyl)phenyl-boronic acid (0.118 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours. The reaction was cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-chloro-3-methyl-4-[4-(4-trifluoromethoxy-phenylsulfamoyl)-phenyl]-naphthalen-2-yl}-acetic acid methyl ester (0.032 g, 23%) as a solid. MS calcd. for $C_{27}H_{20}ClF_3NO_5S$ [(M−H)⁻] 562, obsd. 562.3.

{6-Chloro-3-methyl-4-[4-(4-trifluoromethoxy-phenylsulfamoyl)-phenyl]-naphthalen-2-yl}-acetic acid Lithium hydroxide monohydrate (0.009 g, 0.21 mmol) was added to a stirred solution of {6-chloro-3-methyl-4-[4-(4-trifluoromethoxy-phenylsulfamoyl)-phenyl]-naphthalen-2-yl}-acetic acid methyl ester (0.030 g, 0.05 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-chloro-3-methyl-4-[4-(4-trifluoromethoxy-phenyl-sulfamoyl)-phenyl]-naphthalen-2-yl}-acetic acid (0.02 g, 69%) as a solid. $^1$H NMR (DMSO-$d_6$) δ: 12.49 (br. s, 1H), 10.56 (br. s, 1H), 7.82-8.03 (m, 4H), 7.38-7.54 (m, 3H), 7.27-7.35 (m, 2H), 7.19-7.27 (m, 2H), 6.82 (s, 1H), 3.84 (s, 2H), 1.99 (s, 3H). MS calcd. for $C_{26}H_{18}ClF_3NO_5S$ [(M−H)⁻] 548, obsd. 548.0.

Example 31

{6-Chloro-4-[4-(3-chloro-2-methyl-phenylsulfamoyl)-phenyl]-3-methyl-naphthalen-2-yl}-acetic acid {6-Chloro-4-[4-(3-chloro-2-methyl-phenylsulfamoyl)-phenyl]-3-methyl-naphthalen-2-yl}-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 4-(N-(4-chloro-2-methylphenyl)sulfamoyl)phenylboronic acid (0.110 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-chloro-4-[4-(3-chloro-2-methyl-phenylsulfamoyl)-phenyl]-3-methyl-naphthalen-2-yl}-acetic acid methyl ester (0.045 g, 32%) as a solid. MS calcd. for $C_{27}H_{22}Cl_2NO_4S$ [(M−H)⁻] 526, obsd. 526.4.

{6-Chloro-4-[4-(3-chloro-2-methyl-phenylsulfamoyl)-phenyl]-3-methyl-naphthalen-2-yl}-acetic acid Lithium hydroxide monohydrate (0.013 g, 0.3 mmol) was added to a stirred solution of {6-chloro-4-[4-(3-chloro-2-methyl-phenylsulfamoyl)-phenyl]-3-methyl-naphthalen-2-yl}-acetic acid methyl ester (0.040 g, 0.07 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-chloro-4-[4-(3-chloro-2-methyl-phenylsulfamoyl)-phenyl]-3-methyl-naphthalen-2-yl}-acetic acid (0.035 g, 90%) as a solid. $^1$H NMR (DMSO-$d_6$) δ: 12.49 (br. s, 1H), 9.97 (s, 1H), 7.98 (d, J=8.8 Hz, 1H), 7.91 (s, 1H), 7.78 (d, J=8.3 Hz, 2H), 7.41-7.55 (m, 3H), 7.36 (d, J=7.8 Hz, 1H), 7.19 (t, J=8.1 Hz, 1H), 7.04 (d, J=8.3 Hz, 1H), 6.97 (s, 1H), 3.86 (s, 2H), 2.07 (d, J=5.9 Hz, 6H). MS calcd. for $C_{26}H_{20}Cl_2NO_4S$ [(M−H)⁻] 512, obsd. 512.3.

Example 32

{6-Chloro-4-[4-(3-chloro-phenylsulfamoyl)-phenyl]-3-methyl-naphthalen-2-yl}-acetic acid

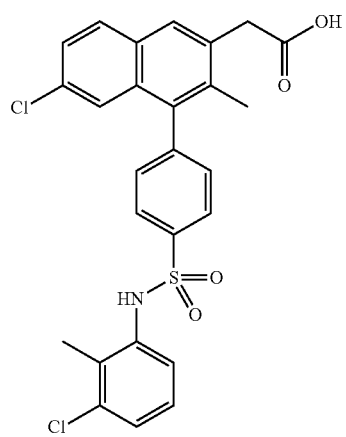 [SMILES: Cc1c(Cl)cccc1NS(=O)(=O)c1ccc(-c2c(C)c(CC(=O)O)cc3ccc(Cl)cc23)cc1]

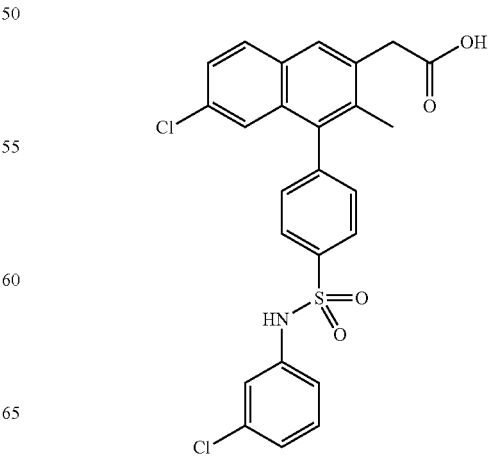

{6-Chloro-4-[4-(3-chloro-phenylsulfamoyl)-phenyl]-3-methyl-naphthalen-2-yl}-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 3-chlorophenyl 4-boronobenzenesulfonamide (0.105 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours, and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-chloro-4-[4-(3-chloro-phenylsulfamoyl)-phenyl]-3-methyl-naphthalen-2-yl}-acetic acid methyl ester (0.085 g, 64%) as a solid.

{6-Chloro-4-[4-(3-chloro-phenylsulfamoyl)-phenyl]-3-methyl-naphthalen-2-yl}-acetic acid Lithium hydroxide monohydrate (0.026 g, 0.62 mmol) was added to a stirred solution of {6-chloro-4-[4-(3-chloro-phenylsulfamoyl)-phenyl]-3-methyl-naphthalen-2-yl}-acetic acid methyl ester (0.080 g, 0.15 mmol) in a 3:1 mixture of THF—$H_2O$ mixture (10 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-chloro-4-[4-(3-chloro-phenylsulfamoyl)-phenyl]-3-methyl-naphthalen-2-yl}-acetic acid (0.064 g, 85%) as a solid. The final product contained a large amount of water as an impurity. $^1$H NMR (DMSO-$d_6$) δ: 7.76-8.08 (m, 4H), 7.40-7.54 (m, 3H), 7.25-7.38 (m, 1H), 7.01-7.23 (m, 3H), 6.81 (s, 1H), 3.83 (s, 2H), 1.98 (s, 3H). MS calcd. for $C_{25}H_{18}Cl_2NO_4S$ [(M–H)$^-$] 498, obsd. 498.3.

Example 33

{6-Chloro-3-methyl-4-[4-(pyrrolidine-1-sulfonyl)-phenyl]-naphthalen-2-yl}-acetic acid

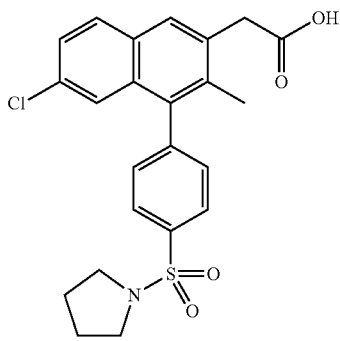 [SMILES: Cc1c(CC(=O)O)cc2ccc(Cl)cc2c1-c1ccc(S(=O)(=O)N2CCCC2)cc1]

{6-Chloro-3-methyl-4-[4-(pyrrolidine-1-sulfonyl)-phenyl]-naphthalen-2-yl}-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 4-boronophenyl(pyrrolidin-1-yl(sulfone) (0.088 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-chloro-3-methyl-4-[4-(pyrrolidine-1-sulfonyl)-phenyl]-naphthalen-2-yl}-acetic acid methyl ester (0.045 g, 39%) as a solid. MS calcd. for $C_{24}H_{23}ClNO_4S$ [(M–H)$^-$] 456, obsd. 456.0.

{6-Chloro-3-methyl-4-[4-(pyrrolidine-1-sulfonyl)-phenyl]-naphthalen-2-yl}-acetic acid Lithium hydroxide monohydrate (0.046 g, 1.09 mmol) was added to a stirred solution of {6-chloro-3-methyl-4-[4-(pyrrolidine-1-sulfonyl)-phenyl]-naphthalen-2-yl}-acetic methyl ester (0.125 g, 0.27 mmol) in a 3:1 mixture of THF—$H_2O$ mixture (15 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-chloro-3-methyl-4-[4-(pyrrolidine-1-sulfonyl)-phenyl]-naphthalen-2-yl}-acetic acid (0.115 g, 95%) as a solid. $^1$H NMR (DMSO-$d_6$) δ: 12.50 (br. s, 1H), 7.80-8.21 (m, 4H), 7.42-7.69 (m, 3H), 6.98 (d, J=5.4 Hz, 1H), 3.86 (d, J=3.9 Hz, 2H), 3.26 (d, J=3.9 Hz, 4H), 2.07 (d, J=3.9 Hz, 3H), 1.69 (d, J=3.9 Hz, 4H). MS calcd. for $C_{23}H_{21}ClNO_4S$ [(M–H)$^-$] 442, obsd. 442.3.

Example 34

{6-Chloro-3-methyl-4-[4-(piperidine-1-sulfonyl)-phenyl]-naphthalen-2-yl}-acetic acid

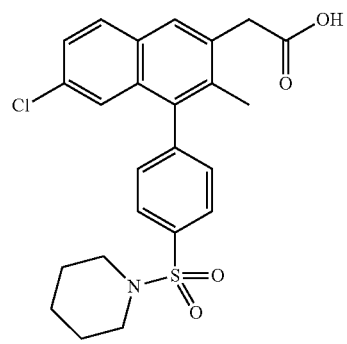 [SMILES: Cc1c(CC(=O)O)cc2ccc(Cl)cc2c1-c1ccc(S(=O)(=O)N2CCCCC2)cc1]

{6-Chloro-3-methyl-4-[4-(piperidine-1-sulfonyl)-phenyl]-naphthalen-2-yl}-acetic acid methyl ester A stirred solution of (6-chloro-3-methyl-4-trifluoromethanesulfonyloxy-naphthalen-2-yl)-acetic acid methyl ester (0.20 g, 0.50 mmol) in dimethoxyethane (10 mL) was purged with argon for 5 minutes at room temperature. Triphenylphosphine (0.030 g, 0.11 mmol), palladium (II) acetate (0.013 g, 0.055 mmol), 1-(4-boronophenylsulfonyl)piperidine (0.183 g, 0.68 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-chloro-3-methyl-4-[4-(piperidine-1-sulfonyl)-phenyl]-naphthalen-2-yl}-acetic acid methyl ester (0.133 g, 58%) as a solid. MS calcd. for $C_{25}H_{25}ClNO_4S$ [(M−H)$^-$] 470, obsd. 470.5.

{6-Chloro-3-methyl-4-[4-(piperidine-1-sulfonyl)-phenyl]-naphthalen-2-yl}-acetic acid Lithium hydroxide monohydrate (0.046 g, 1.1 mmol) was added to a stirred solution of {6-chloro-3-methyl-4-[4-(piperidine-1-sulfonyl)-phenyl]-naphthalen-2-yl}-acetic acid methyl ester (0.130 g, 0.27 mmol) in a 3:1 mixture of THF—$H_2O$ mixture (15 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-chloro-3-methyl-4-[4-(piperidine-1-sulfonyl)-phenyl]-naphthalen-2-yl}-acetic acid (0.125 g, 99%) as a solid. $^1$H NMR (DMSO-$d_6$) δ: 12.51 (br. s, 1H), 7.98 (d, J=8.8 Hz, 1H), 7.88-7.95 (m, 3H), 7.53 (d, J=8.3 Hz, 2H), 7.50 (dd, J=8.8, 1.5 Hz, 1H), 7.01 (s, 1H), 3.87 (s, 2H), 3.02 (t, J=4.9 Hz, 4H), 2.08 (s, 3H), 1.59 (br. s, 4H), 1.33-1.49 (m, 2H). MS calcd. for $C_{24}H_{25}ClNO_4S$ [(M+H)$^+$] 458, obsd. 458.4.

Example 35

[6-Chloro-4-(4-diethylsulfamoyl-phenyl)-3-methyl-naphthalen-2-yl]-acetic acid

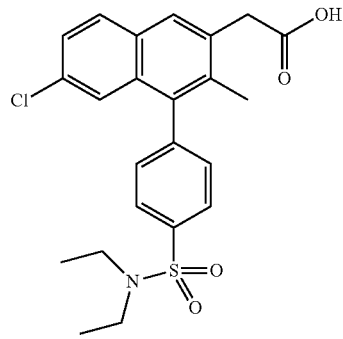 [SMILES: CCN(CC)S(=O)(=O)c1ccc(-c2c(C)c(CC(=O)O)cc3ccc(Cl)cc23)cc1]

[6-Chloro-4-(4-diethylsulfamoyl-phenyl)-3-methyl-naphthalen-2-yl]-acetic acid methyl ester A stirred solution of (6-chloro-3-methyl-4-trifluoromethanesulfonyloxy-naphthalen-2-yl)-acetic acid methyl ester (0.20 g, 0.50 mmol) in dimethoxyethane (10 mL) was purged with argon for 5 minutes at room temperature. Triphenylphosphine (0.030 g, 0.11 mmol), palladium (II) acetate (0.013 g, 0.055 mmol), 4-(N,N-diethylsulfamoyl)phenylboronic acid (0.175 g, 0.68 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [6-chloro-4-(4-diethylsulfamoyl-phenyl)-3-methyl-naphthalen-2-yl]-acetic acid methyl ester (0.035 g, 15%) as a solid.

[6-Chloro-4-(4-diethylsulfamoyl-phenyl)-3-methyl-naphthalen-2-yl]-acetic acid

Lithium hydroxide monohydrate (0.015 g, 0.34 mmol) was added to a stirred solution of [6-chloro-4-(4-diethylsulfamoyl-phenyl)-3-methyl-naphthalen-2-yl]-acetic acid methyl ester (0.040 g, 0.09 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [6-chloro-4-(4-diethylsulfamoyl-phenyl)-3-methyl-naphthalen-2-yl]-acetic acid (0.037 g, 95%) as a solid. $^1$H NMR (DMSO-$d_6$) δ: 12.49 (br. s, 1H), 7.98 (d, J=8.3 Hz, 3H), 7.91 (s, 1H), 7.49 (d, J=8.3 Hz, 3H), 7.00 (s, 1H), 3.86 (s, 2H), 3.28 (s, 4H), 2.07 (s, 3H), 1.08 (t, J=7.1 Hz, 6H). MS calcd. for $C_{23}H_{25}ClNO_4S$ [(M+H)$^+$] 446, obsd. 446.4.

Example 36

[6-Chloro-4-(4-cyclohexylsulfamoyl-phenyl)-3-methyl-naphthalen-2-yl]-acetic acid

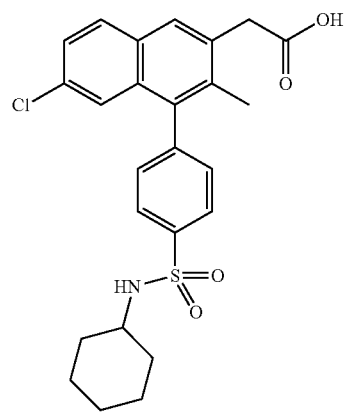 [SMILES: Cc1c(CC(=O)O)cc2ccc(Cl)cc2c1-c1ccc(S(=O)(=O)NC2CCCCC2)cc1]

[6-Chloro-4-(4-cyclohexylsulfamoyl-phenyl)-3-methyl-naphthalen-2-yl]-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 4-N-cyclohexylsulfamoylphenylboronic acid (0.096 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [6-chloro-4-(4-cyclohexylsulfamoyl-phenyl)-3-methyl-naphthalen-2-yl]-acetic acid methyl ester (0.06 g, 50%) as a solid. MS calcd. for $C_{26}H_{27}ClNO_4S$ [(M–H)$^-$] 484, obsd. 484.4.

[6-Chloro-4-(4-cyclohexylsulfamoyl-phenyl)-3-methyl-naphthalen-2-yl]-acetic acid Lithium hydroxide monohydrate (0.019 g, 0.45 mmol) was added to a solution of [6-chloro-4-(4-cyclohexylsulfamoyl-phenyl)-3-methyl-naphthalen-2-yl]-acetic acid (0.055 g, 0.11 mmol) in a 3:1 mixture of THF—H$_2$O mixture (4 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [6-chloro-4-(4-cyclohexylsulfamoyl-phenyl)-3-methyl-naphthalen-2-yl]-acetic acid (0.048 g, 90%) as a solid. $^1$H NMR (400 MHz, DMSO-d$_6$) δ ppm 12.50 (br. s, 1 H), 7.94-8.03 (m, 3 H), 7.91 (s, 1 H), 7.73 (d, J=7.20 Hz, 1 H), 7.44-7.52 (m, 3 H), 6.96 (s, 1 H), 3.86 (s, 2 H), 2.96-3.15 (m, 2 H), 2.08 (s, 3 H), 1.59 (m, 5 H), 0.99-1.28 (m, 6 H). MS calcd. for $C_{25}H_{25}ClNO_4S$ [(M–H)$^-$] 470, obsd. 470.2.

Example 37

[6-Chloro-4-(4-isopropylsulfamoyl-phenyl)-3-methyl-naphthalen-2-yl]-acetic acid

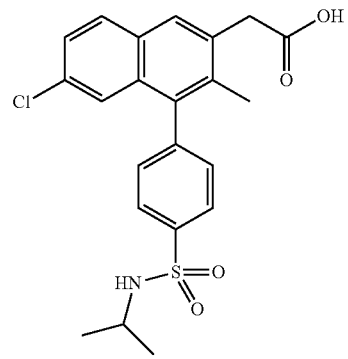 [SMILES: Cc1c(CC(=O)O)cc2ccc(Cl)cc2c1-c1ccc(S(=O)(=O)NC(C)C)cc1]

[6-Chloro-4-(4-isopropylsulfamoyl-phenyl)-3-methyl-naphthalen-2-yl]-acetic acid methyl ester A stirred solution of (6-chloro-3-methyl-4-trifluoromethanesulfonyloxy-naphthalen-2-yl)-acetic acid methyl ester (0.20 g, 0.50 mmol) in dimethoxyethane (10 mL) was purged with argon for 5 minutes at room temperature. Triphenylphosphine (0.030 g, 0.11 mmol), palladium (II) acetate (0.013 g, 0.055 mmol), 4-(N-isopropylylsulfamoyl)phenylboronic acid (0.165 g, 0.68 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [6-chloro-4-(4-isopropylsulfamoyl-phenyl)-3-methyl-naphthalen-2-yl]-acetic acid methyl ester (0.03 g, 13%) as a solid. MS calcd. for $C_{23}H_{23}ClNO_4S$ [(M–H)$^-$] 444, obsd. 444.3.

[6-Chloro-4-(4-isopropylsulfamoyl-phenyl)-3-methyl-naphthalen-2-yl]-acetic acid

Lithium hydroxide monohydrate (0.01 g, 0.24 mmol) was added to a solution of [6-chloro-4-(4-isopropylsulfamoyl-phenyl)-3-methyl-naphthalen-2-yl]-acetic acid (0.027 g, 0.060 mmol) in a 3:1 mixture of THF—H$_2$O mixture (4 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [6-chloro-4-(4-isopropylsulfamoyl-phenyl)-3-methyl-naphthalen-2-yl]-acetic acid (0.021 g, 80%) as a solid. $^1$H NMR (DMSO-d$_6$) δ: 12.51 (br. s., 1H), 7.94-8.06 (m, 3H), 7.91 (s, 1H), 7.69 (d, J=7.3 Hz, 1H), 7.48 (d, J=7.8 Hz, 3H), 6.99 (s, 1H), 3.86 (s, 2H), 3.41 (m, 1H), 2.08 (s, 3H), 1.00 (d, J=6.4 Hz, 6H). MS calcd. for $C_{22}H_{23}ClNO_4S$ [(M+H)$^+$] 432, obsd. 432.4.

Example 38

[4-(4-Benzylsulfamoyl-phenyl)-6-chloro-3-methyl-naphthalen-2-yl]-acetic acid

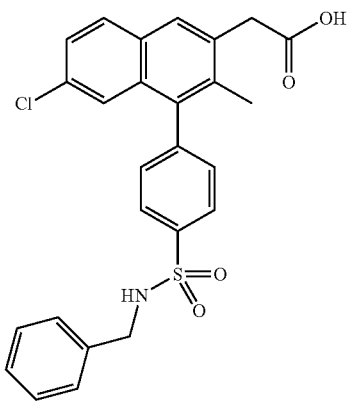 [SMILES: Cc1c(CC(=O)O)cc2ccc(Cl)cc2c1-c1ccc(S(=O)(=O)NCc2ccccc2)cc1]

[4-(4-Benzylsulfamoyl-phenyl)-6-chloro-3-methyl-naphthalen-2-yl]-acetic acid methyl ester A stirred solution of (6-chloro-3-methyl-4-trifluoromethanesulfonyloxy-naphthalen-2-yl)-acetic acid methyl ester (0.20 g, 0.50 mmol) in dimethoxyethane (10 mL) was purged with argon for 5 minutes at room temperature. Triphenylphosphine (0.030 g, 0.11 mmol), palladium (II) acetate (0.013 g, 0.055 mmol), 4-N-benzylsulfamoylphenylboronic acid (0.198 g, 0.68 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [4-(4-benzylsulfamoyl-phenyl)-6-chloro-3-methyl-naphthalen-2-yl]-acetic acid methyl ester (0.093 g, 37%) as a solid. MS calcd. for $C_{27}H_{23}ClNO_4S$ [(M−H)$^-$] 492, obsd. 492.3.

[4-(4-Benzylsulfamoyl-phenyl)-6-chloro-3-methyl-naphthalen-2-yl]-acetic acid

Lithium hydroxide monohydrate (0.031 g, 0.70 mmol) was added to a solution of [4-(4-benzylsulfamoyl-phenyl)-6-chloro-3-methyl-naphthalen-2-yl]-acetic acid methyl ester (0.090 g, 0.18 mmol) in a 3:1 mixture of THF—$H_2O$ mixture (12 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [4-(4-benzylsulfamoyl-phenyl)-6-chloro-3-methyl-naphthalen-2-yl]-acetic acid (0.080 g, 92%) as a solid. $^1$H NMR (400 MHz, DMSO-d$_6$) δ ppm 12.38-12.59 (m, 1 H), 8.34 (t, J=6.40 Hz, 1 H), 7.97 (d, J=8.20 Hz, 1 H), 7.88-7.93 (m, 3 H), 7.50 (dd, J=8.60, 2.40 Hz, 1 H), 7.40 (d, J=8.31 Hz, 2 H), 7.17-7.32 (m, 5 H), 7.03 (d, J=1.47 Hz, 1 H), 4.18 (d, J=5.87 Hz, 2 H), 3.86 (s, 2 H), 2.04 (s, 3 H). MS calcd. for $C_{26}H_{21}ClNO_4S$ [(M−H)$^-$] 478, obsd. 478.2.

Example 39

{6-Chloro-4-[4-(4-methoxy-benzylsulfamoyl)-phenyl]-3-methyl-naphthalen-2-yl}-acetic acid

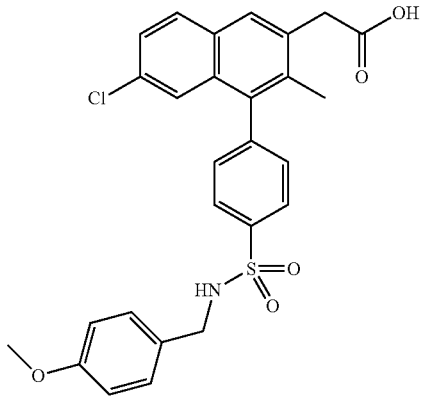 [SMILES: COc1ccc(CNS(=O)(=O)c2ccc(-c3c(C)c(CC(=O)O)cc4ccc(Cl)cc34)cc2)cc1]

{6-Chloro-4-[4-(4-methoxy-benzylsulfamoyl)-phenyl]-3-methyl-naphthalen-2-yl}-acetic acid methyl ester A stirred solution of (6-chloro-3-methyl-4-trifluoromethanesulfonyloxy-naphthalen-2-yl)-acetic acid methyl ester (0.10 g, 0.25 mmol) in dimethoxyethane (5 mL) was purged with argon for 5 minutes at room temperature. Triphenylphosphine (0.015 g, 0.055 mmol), palladium (II) acetate (0.006 g, 0.027 mmol), 4-(N-(4-methoxybenzyl)sulfamoyl) phenylboronic acid (0.109 g, 0.33 mmol) and a 2 M aqueous solution of sodium carbonate (0.6 mL, 1.2 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford {6-chloro-4-[4-(4-methoxy-benzylsulfamoyl)-phenyl]-3-methyl-naphthalen-2-yl}-acetic acid methyl ester (0.093 g, 70%) as a solid. MS calcd. for $C_{28}H_{25}ClNO_5S$ [(M−H)$^-$] 522, obsd. 522.4.

{6-Chloro-4-[4-(4-methoxy-benzylsulfamoyl)-phenyl]-3-methyl-naphthalen-2-yl}-acetic acid Lithium hydroxide monohydrate (0.029 g, 0.68 mmol) was added to a solution {6-chloro-4-[4-(4-methoxy-benzylsulfamoyl)-phenyl]-3-methyl-naphthalen-2-yl}-acetic acid methyl ester (0.090 g, 0.18 mmol) in a 3:1 mixture of THF—$H_2O$ mixture (12 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave {6-chloro-4-[4-(4-methoxy-benzylsulfamoyl)-phenyl]-3-methyl-naphthalen-2-yl}-acetic acid (0.086 g, 98%) as a solid. $^1$H NMR (400 MHz, DMSO-d$_6$) δ ppm 12.43-12.61 (m, 1 H), 8.22 (t, J=6.30 Hz, 1 H), 7.98 (d, J=8.80 Hz, 1 H), 7.89-7.95 (m, 3 H), 7.49 (dd, J=8.80, 2.20 Hz, 1 H), 7.42 (d, J=7.83 Hz, 2 H), 7.15 (d, J=8.80 Hz, 2 H), 7.04 (d, J=1.96 Hz, 1 H), 6.81-6.86 (m, 2 H), 4.09 (d, J=5.87 Hz, 2 H), 3.86 (s, 2 H), 3.68 (s, 3 H), 2.06 (s, 3 H). MS calcd. for $C_{27}H_{23}ClNO_5S$ [(M−H)$^-$] 508, obsd. 508.3.

Example 40

(6-Chloro-4-{4-[isopropyl-(4-methoxy-benzyl)-sulfamoyl]-phenyl}-3-methyl-naphthalen-2-yl)-acetic acid

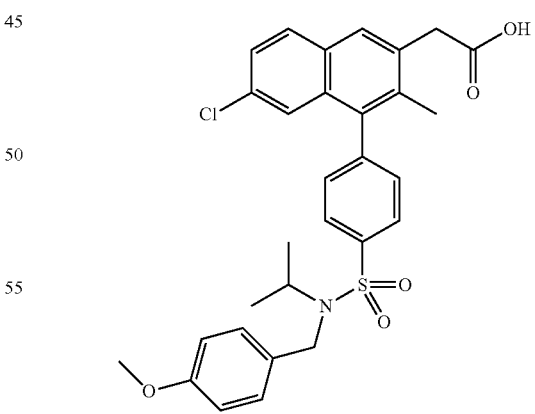

(6-Chloro-4-{4-[isopropyl-(4-methoxy-benzyl)-sulfamoyl]phenyl}-3-methyl-naphthalen-2-yl)-acetic acid methyl ester A stirred solution of (6-chloro-3-methyl-4-trifluoromethanesulfonyloxy-naphthalen-2-yl)-acetic acid methyl ester (0.200 g, 0.50 mmol) in dimethoxyethane (10 mL) was purged with argon for 5 minutes at room temperature. Triphenylphosphine (0.030 g, 0.110 mmol), palladium (II) acetate (0.013 g, 0.060 mmol), 4-(N-isopropyl-N-(4-methoxybenzyl)sulfamoyl)phenyl-boronic acid (0.247 g, 0.68 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and brine, dried over anhydrous $Na_2SO_4$ and concentrated under reduced pressure to give the crude product, which was finally purified using flash chromatography (Biotage, 5-10% ethyl acetate-hexane) to afford (6-chloro-4-{4-[isopropyl-(4-methoxy-benzyl)-sulfamoyl]-phenyl}-3-methyl-naphthalen-2-yl)-acetic acid methyl ester (0.12 g, 42%) as a solid. MS calcd. for $C_{31}H_{31}ClNO_5S$ [(M–H)$^-$] 564, obsd. 564.3.

(6-Chloro-4-{4-[isopropyl-(4-methoxy-benzyl)-sulfamoyl]-phenyl}-3-methyl-naphthalen-2-yl)-acetic acid Lithium hydroxide monohydrate (0.034 g, 0.80 mmol) was added to a solution of (6-chloro-4-{4-[isopropyl-(4-methoxy-benzyl)-sulfamoyl]-phenyl}-3-methyl-naphthalen-2-yl)-acetic acid methyl ester (0.115 g, 0.20 mmol) in a 3:1 mixture of THF—$H_2O$ mixture (15 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave (6-chloro-4-{4-[isopropyl-(4-methoxy-benzyl)-sulfamoyl]-phenyl}-3-methyl-naphthalen-2-yl)-acetic acid (0.096 g, 86%) as a solid. $^1$H NMR (400 MHz, DMSO-$d_6$) δ ppm 12.51 (br. s, 1 H), 8.01 (d, J=8.31 Hz, 2 H), 7.98 (d, J=8.80 Hz, 1 H), 7.92 (s, 1 H), 7.46-7.52 (m, 3 H), 7.34 (d, J=8.80 Hz, 2 H), 7.00 (s, 1 H), 6.91 (d, J=8.80 Hz, 2 H), 4.43 (s, 2 H), 4.13 (spt, J=6.60 Hz, 1 H), 3.87 (s, 2 H), 3.74 (s, 3 H), 2.08 (s, 3 H), 0.93 (d, J=6.85 Hz, 6 H). MS calcd. for $C_{30}H_{29}ClNO_5S$ [(M–H)$^-$] 550, obsd. 550.2.

Example 41

{6-Fluoro-4-[4-(4-fluoro-phenylsulfamoyl)-phenyl]-3-methyl-naphthalen-2-yl}-acetic acid

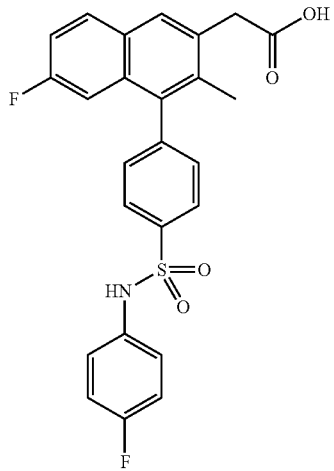 [SMILES: Cc1c(CC(=O)O)cc2ccc(F)cc2c1-c1ccc(S(=O)(=O)Nc2ccc(F)cc2)cc1]

{6-Fluoro-4-[4-(4-fluoro-phenylsulfamoyl)-phenyl]-3-methyl-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-(N-(4-fluorophenyl)sulfamoyl)phenylboronic acid (0.105 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to obtain {6-fluoro-4-[4-(4-fluoro-phenylsulfamoyl)-phenyl]-3-methyl-naphthalen-2-yl}-acetic acid methyl ester (0.015 g, 12%) as a solid. MS calcd. for $C_{26}H_{20}F_2NO_4S$ [(M–H)$^-$] 480, obsd. 480.3.

[6-Fluoro-3-methyl-4-(4-p-tolylsulfamoyl-phenyl)-naphthalen-2-yl]-acetic acid methyl ester Lithium hydroxide monohydrate (0.08 g, 0.19 mmol) was added to a stirred solution of {6-fluoro-4-[4-(4-fluoro-phenylsulfamoyl)-phenyl]-3-methyl-naphthalen-2-yl}-acetic acid methyl ester (0.023 g, 0.047 mmol) in a 3:1 mixture of THF—$H_2O$ mixture (4 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-fluoro-4-[4-(4-fluoro-phenyl-sulfamoyl)-phenyl]-3-methyl-naphthalen-2-yl}-acetic acid (0.017 g, 76%) as a solid. $^1$H NMR (400 MHz, DMSO-$d_6$) δ ppm 12.45 (br. s, 1 H), 7.99 (dd, J=9.20, 6.40 Hz, 1 H), 7.89 (s, 1 H), 7.85 (m, J=8.30 Hz, 2 H), 7.41 (d, J=8.31 Hz, 2 H), 7.34-7.38 (m, 1 H), 7.10-7.15 (m, 3 H), 6.50 (dd, J=11.00, 3.20 Hz, 1 H), 3.83 (s, 2 H), 2.01 (s, 3 H). MS calcd. for $C_{25}H_{18}F_2NO_4S$ [(M–H)$^-$] 466, obsd. 466.0.

Example 42

[6-Fluoro-3-methyl-4-(4-p-tolylsulfamoyl-phenyl)-naphthalen-2-yl]-acetic acid

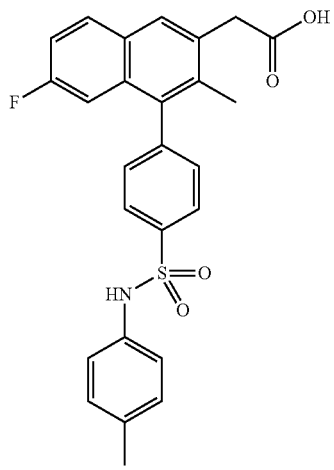 [SMILES: Cc1ccc(NS(=O)(=O)c2ccc(-c3c(C)c(CC(=O)O)cc4ccc(F)cc34)cc2)cc1]

[6-fluoro-3-methyl-4-(4-p-tolylsulfamoyl-phenyl)-naphthalen-2-yl]-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-(N-p-tolylsulfamoyl)phenylsulfamoyl)phenylboronic acid (0.103 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to provide [6-fluoro-3-methyl-4-(4-p-tolylsulfamoyl-phenyl)-naphthalen-2-yl]-acetic acid methyl ester (0.055 g, 46%) as a solid. MS calcd. for $C_{27}H_{23}FNO_4S$ [(M–H)$^-$] 476, obsd. 476.4.

[6-Fluoro-3-methyl-4-(4-p-tolylsulfamoyl-phenyl)-naphthalen-2-yl]-acetic acid

Lithium hydroxide monohydrate (0.017 g, 0.41 mmol) was added to a stirred solution of [6-fluoro-3-methyl-4-(4-p-tolylsulfamoyl-phenyl)-naphthalen-2-yl]-acetic acid methyl ester (0.05 g, 0.1 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded [6-chloro-3-methyl-4-(4-p-tolylsulfamoyl-phenyl)-naphthalen-2-yl]-acetic acid (0.038 g, 79%) as a solid. $^1$H NMR (400 MHz, DMSO-d$_6$) δ ppm 12.40-12.49 (br. s, 1 H), 10.07-10.13 (br. s, 1H), 7.99 (dd, J=9.60, 6.40 Hz, 1 H), 7.88 (s, 1 H), 7.85 (d, J=8.31 Hz, 2 H), 7.40 (d, J=8.31 Hz, 2 H), 7.34-7.38 (m, 1 H), 7.06 (s, 2 H), 7.01 (s, 2 H), 6.49 (dd, J=11.00, 3.00 Hz, 1 H), 3.83 (s, 2 H), 2.21 (s, 3 H), 2.01 (s, 3 H). MS calcd. for $C_{26}H_{21}FNO_4S$ [(M–H)$^-$] 462, obsd. 462.4.

Example 43

{6-Fluoro-3-methyl-4-[4-(4-trifluoromethoxy-phenylsulfamoyl)-phenyl]-naphthalen-2-yl}-acetic acid

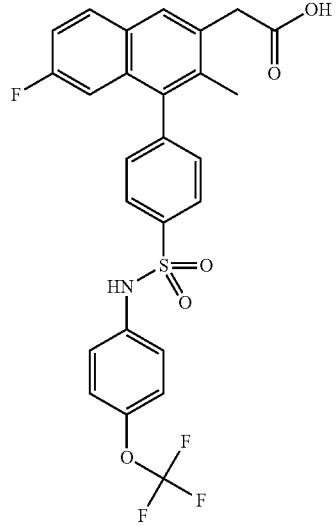 [SMILES: Cc1c(CC(=O)O)cc2ccc(F)cc2c1-c1ccc(S(=O)(=O)Nc2ccc(OC(F)(F)F)cc2)cc1]

{6-Fluoro-3-methyl-4-[4-(4-trifluoromethoxy-phenylsulfamoyl)-phenyl]-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-(N-(4-(trifluoromethoxy)phenyl)sulfamoyl)phenyl-boronic acid (0.128 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to provide {6-fluoro-3-methyl-4-[4-(4-trifluoromethoxy-phenylsulfamoyl)-phenyl]-naphthalen-2-yl}-acetic acid methyl ester (0.040 g, 29%) as a solid. MS calcd. for $C_{27}H_{20}F_4NO_5S$ [(M–H)$^-$] 546, obsd. 546.0.

{6-Fluoro-3-methyl-4-[4-(4-trifluoromethoxy-phenylsulfamoyl)-phenyl]-naphthalen-2-yl}-acetic acid Lithium hydroxide monohydrate (0.012 g, 0.39 mmol) was added to a stirred solution of {6-fluoro-3-methyl-4-[4-(4-trifluoromethoxy-phenylsulfamoyl)-phenyl]-naphthalen-2-yl}-acetic acid methyl ester (0.038 g, 0.07 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-fluoro-3-methyl-4-[4-(4-trifluoromethoxy-phenyl-sulfamoyl)-phenyl]-naphthalen-2-yl}-acetic acid (0.031 g, 84%) as a solid. $^1$H NMR (400 MHz, DMSO-d$_6$) δ ppm 12.46 (br. s, 1 H), 10.56 (br. s, 1 H), 7.99 (dd, J=9.00, 6.40 Hz, 1 H), 7.90 (m, J=8.30 Hz, 2 H), 7.88 (s, 1 H), 7.42 (m, J=8.30 Hz, 2 H), 7.37 (td, J=8.80, 2.40 Hz, 1 H), 7.21-7.31 (m, 4 H), 6.49 (dd, J=11.00, 2.60 Hz, 1 H), 3.82 (s, 2 H), 1.99 (s, 3 H). MS calcd. for $C_{26}H_{18}F_4NO_5S$ [(M–H)$^-$] 532, obsd. 532.0.

Example 44

{4-[4-(3-Chloro-2-methyl-phenylsulfamoyl)-phenyl]-6-fluoro-3-methyl-naphthalen-2-yl}-acetic acid

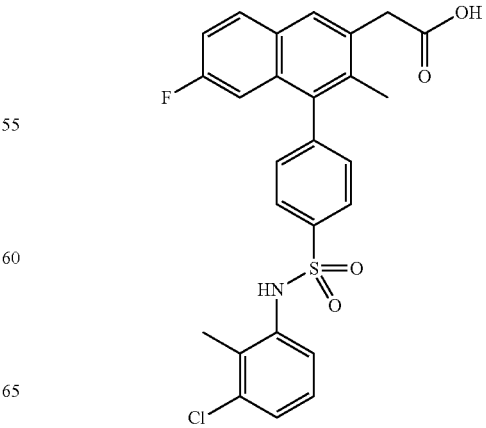

{4-[4-(3-Chloro-2-methyl-phenylsulfamoyl)-phenyl]-6-fluoro-3-methyl-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-(N-(4-chloro-2-methylphenyl)sulfamoyl)phenylboronic acid (0.115 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {4-[4-(3-chloro-2-methyl-phenylsulfamoyl)-phenyl]-6-fluoro-3-methyl-naphthalen-2-yl}-acetic acid methyl ester (0.052 g, 40%) as a solid. MS calcd. for $C_{27}H_{22}ClFNO_4S$ [(M−H)$^-$] 510, obsd. 510.3.

{4-[4-(3-chloro-2-methyl-phenylsulfamoyl)-phenyl]-6-fluoro-3-methyl-naphthalen-2-yl}-acetic acid Lithium hydroxide monohydrate (0.017 g, 0.39 mmol) was added to a stirred solution of {4-[4-(3-chloro-2-methyl-phenylsulfamoyl)-phenyl]-6-fluoro-3-methyl-naphthalen-2-yl}-acetic acid methyl ester (0.050 g, 0.10 mmol) in a 3:1 mixture of THF—$H_2O$ mixture (5 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {4-[4-(3-chloro-2-methyl-phenylsulfamoyl)-phenyl]-6-fluoro-3-methyl-naphthalen-2-yl}-acetic acid (0.039 g, 80%) as a solid. $^1$H NMR (400 MHz, DMSO-$d_6$) δ ppm 12.46 (br. s, 1 H), 9.95 (br. s, 1 H), 8.01 (dd, J=8.80, 6.40 Hz, 1 H), 7.90 (s, 1 H), 7.77 (d, J=7.80 Hz, 2 H), 7.32-7.46 (m, 4 H), 7.18 (t, J=7.80 Hz, 1 H), 7.03 (d, J=7.80 Hz, 1 H), 6.63 (dd, J=11.00, 2.40 Hz, 1 H), 3.85 (s, 2 H), 2.07 (s, 3 H), 2.06 (s, 3 H). MS calcd. for $C_{26}H_{20}ClFNO_4S$ [(M−H)$^-$] 496, obsd. 496.3.

Example 45

{4-[4-(3-Chloro-phenylsulfamoyl)-phenyl]-6-fluoro-3-methyl-naphthalen-2-yl}-acetic acid

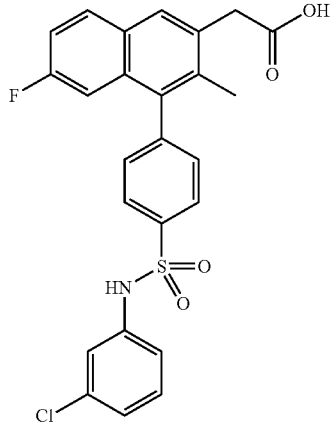 [SMILES: Cc1c(CC(=O)O)cc2ccc(F)cc2c1-c1ccc(S(=O)(=O)Nc2cccc(Cl)c2)cc1]

{4-[4-(3-Chloro-phenylsulfamoyl)-phenyl]-6-fluoro-3-methyl-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 3-chlorophenyl 4-boronobenzenesulfonamide (0.110 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford {4-[4-(3-chloro-phenylsulfamoyl)-phenyl]-6-fluoro-3-methyl-naphthalen-2-yl}-acetic acid methyl ester (0.09 g, 72%) as a solid.

{4-[4-(3-Chloro-phenylsulfamoyl)-phenyl]-6-fluoro-3-methyl-naphthalen-2-yl}-acetic acid Lithium hydroxide monohydrate (0.030 g, 0.72 mmol) was added to a stirred solution of {4-[4-(3-chloro-phenylsulfamoyl)-phenyl]-6-fluoro-3-methyl-naphthalen-2-yl}-acetic acid methyl ester (0.090 g, 0.18 mmol) in a 3:1 mixture of THF—$H_2O$ mixture (10 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {4-[4-(3-chloro-phenylsulfamoyl)-phenyl]-6-fluoro-3-methyl-naphthalen-2-yl}-acetic acid (0.082 g, 93%) as a solid. $^1$H NMR (400 MHz, DMSO-$d_6$) δ ppm 12.47 (br. s, 1 H), 10.60 (br. s, 1 H), 8.00 (dd, J=8.80, 6.80 Hz, 1 H), 7.88-7.92 (m, 3 H), 7.45 (d, J=8.31 Hz, 2 H), 7.29-7.40 (m, 2 H), 7.09-7.17 (m, 3 H), 6.52 (d, J=11.74 Hz, 1 H), 3.83 (s, 2 H), 2.00 (s, 3 H). MS calcd. for $C_{25}H_{18}FClNO_4S$ [(M−H)$^-$] 482, obsd. 482.3.

Example 46

{6-Fluoro-3-methyl-4-[4-(pyrrolidine-1-sulfonyl)-phenyl]-naphthalen-2-yl}-acetic acid

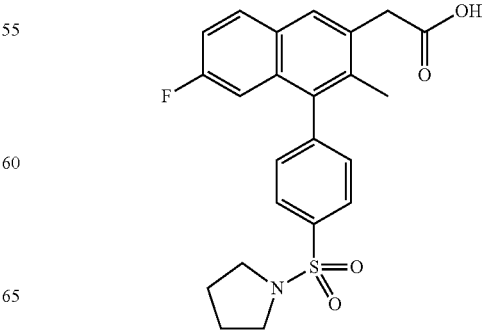

{6-Fluoro-3-methyl-4-[4-(pyrrolidine-1-sulfonyl)-phenyl]-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-boronophenyl(pyrrolidin-1-yl(sulfone) (0.09 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-fluoro-3-methyl-4-[4-(pyrrolidine-1-sulfonyl)-phenyl]-naphthalen-2-yl}-acetic acid methyl ester (0.08 g, 72%) as a solid. MS calcd. for $C_{24}H_{23}FNO_4S$ [(M–H)$^-$] 440, obsd. 440.1.

{6-Fluoro-3-methyl-4-[4-(pyrrolidine-1-sulfonyl)-phenyl]-naphthalen-2-yl}-acetic acid Lithium hydroxide monohydrate (0.02 g, 0.68 mmol) was added to a stirred solution of {6-fluoro-3-methyl-4-[4-(pyrrolidine-1-sulfonyl)-phenyl]-naphthalen-2-yl}-acetic acid methyl ester (0.075 g, 0.17 mmol) in a 3:1 mixture of THF—$H_2O$ mixture (8 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-fluoro-3-methyl-4-[4-(pyrrolidine-1-sulfonyl)-phenyl]-naphthalen-2-yl}-acetic acid (0.064 g, 88%) as a solid. $^1$H NMR (400 MHz, DMSO-d$_6$) δ ppm 12.47 (br. s, 1 H), 7.98 (d, J=8.31 Hz, 3H), 7.91 (s, 1 H), 7.51 (d, J=8.31 Hz, 2 H), 7.39 (td, J=8.80, 2.40 Hz, 1 H), 6.69 (dd, J=11.20, 2.40 Hz, 1 H), 3.85 (s, 2 H), 3.21-3.29 (m, 4 H), 2.07 (s, 3 H), 1.64-1.76 (m, 4 H). MS calcd. for $C_{23}H_{21}FNO_4S$ [(M–H)$^-$] 426, obsd. 426.4.

Example 47

{6-Fluoro-3-methyl-4-[4-(piperidine-1-sulfonyl)-phenyl]-naphthalen-2-yl}-acetic acid {6-Fluoro-3-methyl-4-[4-(piperidine-1-sulfonyl)-phenyl]-naphthalen-2-yl}-acetic acid methyl ester A stirred solution of (6-fluoro-3-methyl-4-trifluoromethanesulfonyloxy-naphthalen-2-yl)-acetic acid methyl ester (0.20 g, 0.52 mmol) in dimethoxyethane (10 mL) was purged with argon for 5 minutes at room temperature. Triphenylphosphine (0.031 g, 0.12 mmol), palladium (II) acetate (0.013 g, 0.06 mmol), 1-(4-boronophenylsulfonyl)piperidine (0.191 g, 0.71 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to {6-fluoro-3-methyl-4-[4-(piperidine-1-sulfonyl)-phenyl]-naphthalen-2-yl}-acetic acid methyl ester (0.195 g, 84%) as a solid. MS calcd. for $C_{25}H_{25}FNO_4S$ [(M–H)$^-$] 454, obsd. 454.2 (low intensity).

{6-Fluoro-3-methyl-4-[4-(piperidine-1-sulfonyl)-phenyl]-naphthalen-2-yl}-acetic acid Lithium hydroxide monohydrate (0.06 g, 1.6 mmol) was added to a stirred solution of {6-fluoro-3-methyl-4-[4-(piperidine-1-sulfonyl)-phenyl]-naphthalen-2-yl}-acetic acid methyl ester (0.186 g, 0.39 mmol) in a 3:1 mixture of THF—$H_2O$ mixture (16 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane afforded {6-fluoro-3-methyl-4-[4-(piperidine-1-sulfonyl)-phenyl]-naphthalen-2-yl}-acetic acid (0.17 g, 94%) as a solid. $^1$H NMR (400 MHz, DMSO-d$_6$) δ ppm 12.39-12.68 (br. s, 1 H), 8.02 (dd, J=8.80, 6.20 Hz, 1 H), 7.88-7.92 (m, 3 H), 7.52 (d, J=8.31 Hz, 2 H), 7.39 (td, J=8.80, 2.40 Hz, 1 H), 6.71 (dd, J=11.00, 2.00 Hz, 1 H), 3.85 (s, 2 H), 3.01 (m, 4 H), 2.07 (s, 3 H), 1.54-1.64 (m, 4 H), 1.39-1.47 (m, 2 H). MS calcd. for $C_{24}H_{23}FNO_4S$ [(M–H)$^-$] 440, obsd. 440.3.

Example 48

[4-(4-Diethylsulfamoyl-phenyl)-6-fluoro-3-methyl-naphthalen-2-yl]-acetic acid

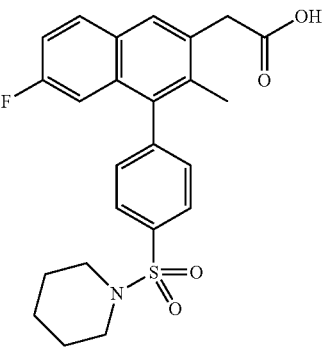 [SMILES: Cc1c(CC(=O)O)cc2ccc(F)cc2c1-c1ccc(S(=O)(=O)N2CCCCC2)cc1]

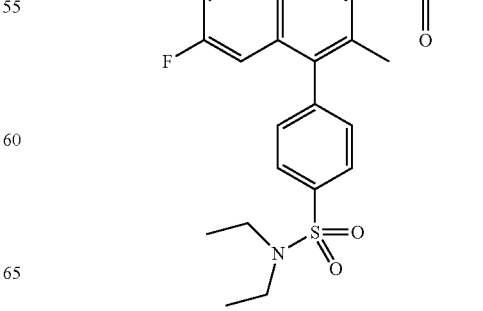

[4-(4-Diethylsulfamoyl-phenyl)-6-fluoro-3-methyl-naphthalen-2-yl]-acetic acid methyl ester A stirred solution of (6-fluoro-3-methyl-4-trifluoromethanesulfonyloxy-naphthalen-2-yl)-acetic acid methyl ester (0.20 g, 0.52 mmol) in dimethoxyethane (10 mL) was purged with argon for 5 minutes at room temperature. Triphenylphosphine (0.031 g, 0.12 mmol), palladium (II) acetate (0.013 g, 0.06 mmol), 4-(N,N-diethylsulfamoyl)phenylboronic acid (0.182 g, 0.71 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [4-(4-diethylsulfamoyl-phenyl)-6-fluoro-3-methyl-naphthalen-2-yl]-acetic acid methyl ester (0.020 g, 9%) as a solid.

[4-(4-Diethylsulfamoyl-phenyl)-6-fluoro-3-methyl-naphthalen-2-yl]-acetic acid Lithium hydroxide monohydrate (0.020 g, 0.45 mmol) was added to a stirred solution of [4-(4-diethylsulfamoyl-phenyl)-6-fluoro-3-methyl-naphthalen-2-yl]-acetic acid methyl ester (0.05 g, 0.11 mmol) in a 3:1 mixture of THF—$H_2O$ mixture (6 mL). The reaction mixture was stirred for 16 hours at room temperature. The reaction mixture was concentrated to remove THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [4-(4-diethylsulfamoyl-phenyl)-6-fluoro-3-methyl-naphthalen-2-yl]-acetic acid (0.042 g, 87%) as a solid. $^1$H NMR (400 MHz, DMSO-$d_6$) δ ppm 12.48 (br. s, 1 H), 8.01 (dd, J=9.20, 6.20 Hz, 1 H), 7.97 (d, J=8.31 Hz, 2 H), 7.91 (s, 1 H), 7.48 (d, J=8.31 Hz, 2 H), 7.39 (td, J=8.80, 2.40 Hz, 1 H), 6.68 (dd, J=11.00, 2.40 Hz, 1 H), 3.85 (s, 2 H), 3.28 (q, J=7.10 Hz, 4 H), 2.07 (s, 3 H), 1.09 (t, J=7.09 Hz, 6 H). MS calcd. for $C_{23}H_{23}FNO_4S$ [(M–H)$^-$] 428, obsd. 428.0.

Example 49

[4-(4-Cyclohexylsulfamoyl-phenyl)-6-fluoro-3-methyl-naphthalen-2-yl]-acetic acid

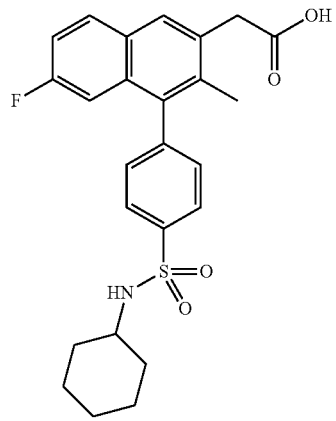 [SMILES: Cc1c(CC(=O)O)cc2ccc(F)cc2c1-c1ccc(S(=O)(=O)NC2CCCCC2)cc1]

[4-(4-Cyclohexylsulfamoyl-phenyl)-6-fluoro-3-methyl-naphthalen-2-yl]-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) was purged with argon for 5 minutes at room temperature. Triphenylphosphine (0.016 g, 0.06 mmol), palladium (II) acetate (0.007 g, 0.03 mmol), 4-N-cyclohexylsulfamoylphenylboronic acid (0.099 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [4-(4-cyclohexylsulfamoyl-phenyl)-6-fluoro-3-methyl-naphthalen-2-yl]-acetic acid methyl ester (0.038 g, 33%) as a solid. MS calcd. for $C_{26}H_{27}FNO_4S$ [(M–H)$^-$] 468, obsd. 468.4.

[4-(4-Cyclohexylsulfamoyl-phenyl)-6-fluoro-3-methyl-naphthalen-2-yl]-acetic acid Lithium hydroxide monohydrate (0.018 g, 0.42 mmol) was added to a solution of [4-(4-cyclohexylsulfamoyl-phenyl)-6-fluoro-3-methyl-naphthalen-2-yl]-acetic acid methyl ester (0.05 g, 0.10 mmol) in a 3:1 mixture of THF—$H_2O$ mixture (6 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [4-(4-cyclohexylsulfamoyl-phenyl)-6-fluoro-3-methyl-naphthalen-2-yl]-acetic acid (0.042 g, 87%) as a solid. $^1$H NMR (400 MHz, DMSO-$d_6$) δ ppm 12.46 (br. s, 1 H), 7.95-8.06 (m, 3 H), 7.90 (s, 1 H), 7.72 (d, J=7.80 Hz, 1 H), 7.46 (d, J=8.31 Hz, 2 H), 7.38 (td, J=8.40, 2.40 Hz, 1 H), 6.63 (dd, J=11.20, 2.40 Hz, 1 H), 3.85 (s, 2 H), 3.00-3.09 (m, 1 H), 2.08 (s, 3 H), 1.52-1.67 (m, 4 H), 1.41-1.51 (m, 1H), 1.03-1.25 (m, 5H). MS calcd. for $C_{25}H_{25}FNO_4S$ [(M–H)$^-$] 454, obsd. 454.4.

Example 50

[6-Fluoro-4-(4-isopropylsulfamoyl-phenyl)-3-methyl-naphthalen-2-yl]-acetic acid

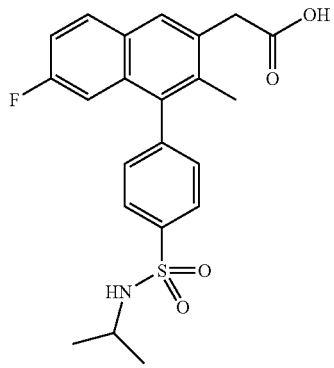 [SMILES: Cc1c(CC(=O)O)cc2ccc(F)cc2c1-c1ccc(S(=O)(=O)NC(C)C)cc1]

[6-Fluoro-4-(4-isopropylsulfamoyl-phenyl)-3-methyl-naphthalen-2-yl]-acetic acid methyl ester A stirred solution of (6-fluoro-3-methyl-4-trifluoromethanesulfonyloxy-naphthalen-2-yl)-acetic acid methyl ester (0.20 g, 0.52 mmol) in dimethoxyethane (10 mL) for 5 minutes at room temperature. Triphenylphosphine (0.031 g, 0.12 mmol), palladium (II) acetate (0.013 g, 0.06 mmol), 4-(N-isopropylylsulfamoyl)phenylboronic acid (0.173 g, 0.71 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [6-fluoro-4-(4-isopropylsulfamoyl-phenyl)-3-methyl-naphthalen-2-yl]-acetic acid methyl ester (0.161 g, 72%) as a solid. MS calcd. for $C_{23}H_{23}FNO_4S$ $[(M-H)^-]$ 428, obsd. 428.3.

[6-Fluoro-4-(4-isopropylsulfamoyl-phenyl)-3-methyl-naphthalen-2-yl]-acetic acid Lithium hydroxide monohydrate (0.059 g, 1.40 mmol) was added to a solution of [6-fluoro-4-(4-isopropylsulfamoyl-phenyl)-3-methyl-naphthalen-2-yl]-acetic acid (0.150 g, 0.34 mmol) in a 3:1 mixture of THF—$H_2O$ mixture (15 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [6-fluoro-4-(4-isopropylsulfamoyl-phenyl)-3-methyl-naphthalen-2-yl]-acetic acid (0.120 g, 83%) as a solid. $^1H$ NMR (400 MHz, DMSO-$d_6$) δ ppm 12.48 (br. s, 1 H), 7.98 (d, J=8.31 Hz, 3 H), 7.90 (s, 1 H), 7.69 (d, J=7.82 Hz, 1 H), 7.47 (d, J=8.31 Hz, 2 H), 7.39 (td, J=8.80, 2.40 Hz, 1 H), 6.66 (dd, J=11.00, 2.40 Hz, 1 H), 3.85 (s, 2 H), 3.39 (spt, J=6.80 Hz, 1 H), 2.07 (s, 3 H), 1.01 (d, J=6.85 Hz, 1 H). MS calcd. for $C_{22}H_{21}FNO_4S$ $[(M-H)^-]$ 414, obsd. 414.3.

Example 51

[4-(4-Benzylsulfamoyl-phenyl)-6-fluoro-3-methyl-naphthalen-2-yl]-acetic acid

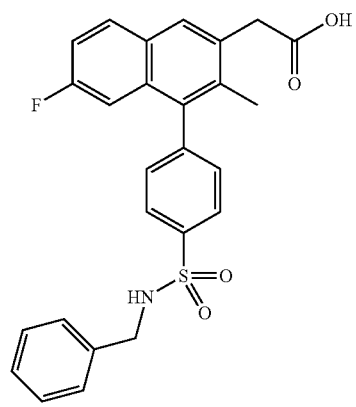 [SMILES: Cc1c(CC(=O)O)cc2ccc(F)cc2c1-c1ccc(S(=O)(=O)NCc2ccccc2)cc1]

[4-(4-Benzylsulfamoyl-phenyl)-6-fluoro-3-methyl-naphthalen-2-yl]-acetic acid methyl ester A stirred solution of (6-fluoro-3-methyl-4-trifluoromethanesulfonyloxy-naphthalen-2-yl)-acetic acid methyl ester (0.20 g, 0.52 mmol) in dimethoxyethane (10 mL) for 5 minutes at room temperature. Triphenylphosphine (0.031 g, 0.12 mmol), palladium (II) acetate (0.013 g, 0.06 mmol), 4-N-benzylsulfamoylphenylboronic acid (0.206 g, 0.71 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford [4-(4-benzylsulfamoyl-phenyl)-6-fluoro-3-methyl-naphthalen-2-yl]-acetic acid methyl ester (0.110 g, 46%) as a solid. MS calcd. for $C_{27}H_{23}FNO_4S$ $[(M-H)^-]$ 476, obsd. 476.3.

[4-(4-Benzylsulfamoyl-phenyl)-6-fluoro-3-methyl-naphthalen-2-yl]-acetic acid Lithium hydroxide monohydrate (0.031 g, 0.7 mmol) was added to a solution of [444-benzylsulfamoyl-phenyl)-6-fluoro-3-methyl-naphthalen-2-yl]-acetic acid methyl ester (0.09 g, 0.18 mmol) in a 3:1 mixture of THF—$H_2O$ mixture (12 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave [4-(4-benzylsulfamoyl-phenyl)-6-fluoro-3-methyl-naphthalen-2-yl]-acetic acid (0.080 g, 92%) as a solid. $^1H$ NMR (400 MHz, DMSO-$d_6$) δ ppm 12.40-12.55 (m, 1 H), 8.35 (t, J=6.40 Hz, 1 H), 8.01 (dd, J=9.00, 6.40 Hz, 1 H), 7.87-7.93 (m, 3 H), 7.35-7.43 (m, 3 H), 7.17-7.30 (m, 5 H), 6.67 (dd, J=11.00, 2.60 Hz, 1 H), 4.18 (d, J=5.87 Hz, 2 H), 3.85 (s, 2 H), 2.05 (s, 3 H) MS calcd. for $C_{26}H_{21}FNO_4S$ $[(M-H)^-]$ 462, obsd. 462.4.

Example 52

{6-Fluoro-4-[4-(4-methoxy-benzylsulfamoyl)-phenyl]-3-methyl-naphthalen-2-yl}-acetic acid

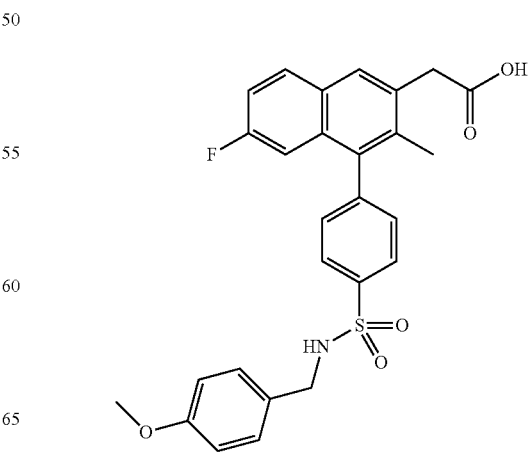

{6-Fluoro-4-[4-(4-methoxy-benzylsulfamoyl)-phenyl]-3-methyl-naphthalen-2-yl}-acetic acid methyl ester A stirred solution of (6-fluoro-3-methyl-4-trifluoromethanesulfonyloxy-naphthalen-2-yl)-acetic acid methyl ester (0.10 g, 0.26 mmol) in dimethoxyethane (5 mL) for 5 minutes at room temperature. Triphenylphosphine (0.016 g, 0.006 mmol), palladium (II) acetate (0.007 g, 0.003 mmol), 4-(N-(4-methoxybenzyl)sulfamoyl)phenylboronic acid (0.135 g, 0.35 mmol) and a 2 M aqueous solution of sodium carbonate (0.5 mL, 1.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and then brine, dried over anhydrous $Na_2SO_4$ and concentrated under reduced pressure to give the crude product, which was finally purified using flash chromatography (Biotage, 5-10% ethyl acetate-hexane) to afford {6-fluoro-4-[4-(4-methoxy-benzylsulfamoyl)-phenyl]-3-methyl-naphthalen-2-yl}-acetic acid methyl ester (0.055 g, 41%) as a solid. MS calcd. for $C_{28}H_{25}FNO_5S$ [(M−H)$^-$] 506, obsd. 506.2.

{6-Fluoro-4-[4-(4-methoxy-benzylsulfamoyl)-phenyl]-3-methyl-naphthalen-2-yl}-acetic acid Lithium hydroxide monohydrate (0.017 g, 0.43 mmol) was added to a solution {6-fluoro-4-[4-(4-methoxy-benzylsulfamoyl)-phenyl]-3-methyl-naphthalen-2-yl}-acetic acid methyl ester (0.054 g, 0.10 mmol) in a 3:1 mixture of THF—$H_2O$ mixture (6 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave {6-fluoro-4-[4-(4-methoxy-benzylsulfamoyl)-phenyl]-3-methyl-naphthalen-2-yl}-acetic acid (0.052 g, 99%) as a solid. $^1$H NMR (400 MHz, DMSO-d$_6$) δ ppm 12.48 (br. s, 1 H), 8.22 (t, J=6.40 Hz, 1 H), 8.01 (dd, J=8.80, 6.80 Hz, 1 H), 7.92 (d, J=8.20 Hz, 2 H), 7.89-7.90 (m, 1 H), 7.36-7.44 (m, 3 H), 7.12-7.17 (m, 2 H), 6.80-6.84 (m, 2 H), 6.69 (dd, J=11.20, 2.40 Hz, 1 H), 4.09 (d, J=6.60 Hz, 2 H), 3.82-3.88 (m, 2 H), 3.68 (s, 3 H), 2.06 (s, 3 H). MS calcd. for $C_{27}H_{23}FNO_5S$ [(M−H)$^-$] 492, obsd. 492.3.

Example 53

(6-Fluoro-4-{4-[isopropyl-(4-methoxy-benzyl)-sulfamoyl]-phenyl}-3-methyl-naphthalen-2-yl)-acetic acid

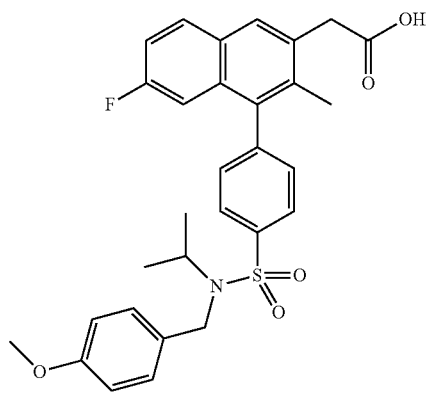 [SMILES: COc1ccc(CN(C(C)C)S(=O)(=O)c2ccc(-c3c(C)c(CC(=O)O)cc4ccc(F)cc34)cc2)cc1]

(6-Fluoro-4-{4-[isopropyl-(4-methoxy-benzyl)-sulfamoyl]-phenyl}-3-methyl-naphthalen-2-yl)-acetic acid methyl ester A stirred solution of (6-fluoro-3-methyl-4-trifluoromethanesulfonyloxy-naphthalen-2-yl)-acetic acid methyl ester (0.200 g, 0.52 mmol) in dimethoxyethane (10 mL) for 5 minutes at room temperature. Triphenylphosphine (0.031 g, 0.12 mmol), palladium (II) acetate (0.013 g, 0.060 mmol), 4-(N-isopropyl-N-(4-methoxybenzyl)sulfamoyl)phenyl-boronic acid (0.258 g, 0.71 mmol) and a 2 M aqueous solution of sodium carbonate (1.0 mL, 2.0 mmol) were added simultaneously to the reaction mixture at room temperature under argon. The reaction mixture was refluxed for 2 hours and then cooled to room temperature. Water was added and the mixture was extracted twice with ethyl acetate. The collected organic extracts were washed with water and brine, dried over anhydrous $Na_2SO_4$ and concentrated under reduced pressure to give the crude product, which was finally purified using flash chromatography (Biotage, 5-10% ethyl acetate-hexane) to afford (6-fluoro-4-{4-[isopropyl-(4-methoxy-benzyl)-sulfamoyl]-phenyl}-3-methyl-naphthalen-2-yl)-acetic acid methyl ester (0.17 g, 61%) as a solid. MS calcd. for $C_{31}H_{31}FNO_5S$ [(M−H)$^-$] 548, obsd. 548.4.

(6-Fluoro-4-{4-[isopropyl-(4-methoxy-benzyl)-sulfamoyl]-phenyl}-3-methyl-naphthalen-2-yl)-acetic acid Lithium hydroxide monohydrate (0.051 g, 1.23 mmol) was added to a solution of (6-fluoro-4-{4-[isopropyl-(4-methoxy-benzyl)-sulfamoyl]-phenyl}-3-methyl-naphthalen-2-yl)-acetic acid methyl ester (0.17 g, 0.30 mmol) in a 3:1 mixture of THF—$H_2O$ mixture (15 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous $Na_2SO_4$, and concentrated under reduced pressure to give the crude product. Trituration with hexane gave (6-fluoro-4-{4-[isopropyl-(4-methoxy-benzyl)-sulfamoyl]-phenyl}-3-methyl-naphthalen-2-yl)-acetic acid (0.138 g, 82%) as a solid. $^1$H NMR (400 MHz, DMSO-d$_6$) δ ppm 12.49 (br. s, 1 H), 7.98-8.04 (m, 3 H), 7.90-7.92 (m, 1 H), 7.47 (d, J=7.80 Hz, 1 H), 7.39 (td, J=8.60, 2.40 Hz, 1 H), 7.33 (d, J=8.00 Hz, 2 H), 6.91 (d, J=8.20 Hz, 2 H), 6.67 (dd, J=11.00, 2.60 Hz, 1 H), 4.41-4.44 (m, 2 H), 4.13 (spt, J=6.80 Hz, 1 H), 3.86 (s, 2H), 3.74 (s, 3H), 2.08 (s, 3H), 0.93 (d, J=6.85 Hz, 6 H). MS calcd. for $C_{30}H_{29}FNO_5S$ [(M−H)$^-$] 534, obsd. 534.3.

Example 54

[6-Fluoro-4-(4-methansulfonyl-phenyl)-3-methyl-naphthalen-2-yl]-acetic acid

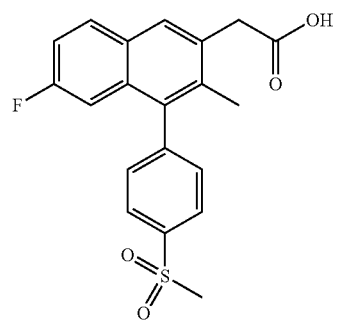 [SMILES: Cc1c(CC(=O)O)cc2ccc(F)cc2c1-c1ccc(S(C)(=O)=O)cc1]

[6-Fluoro-4-(4-methansulfonyl-phenyl)-3-methyl-naphthalen-2-yl]-acetic acid methyl ester To a mixture of 4-(methanesulfonyl)benzeneboronic acid (146 mg, 0.734 mmol), (6-fluoro-3-methyl-4-trifluoromethanesulfonyloxy-naphthalen-2-yl)-acetic acid methyl ester (93 mg, 0.244 mmol), 1,1'-bis(diphenylphosphino)ferrocenedichloropalladium (II) (36 mg, 0.048 mmol), and cesium carbonate (239 mg, 0.734 mmol) was added anhydrous DMF (5 mL) at room temperature. The resulting light brown suspension was heated to reflux for 15 hours. The reaction mixture was cooled to room temperature and diluted with brine and ethyl acetate. The two layers were separated and the aqueous layer was extracted with ethyl acetate and the combined extracts were washed with brine. The organic layer was dried over anhydrous $MgSO_4$, filtered, and concentrated to give the crude residue. Flash chromatography (80 g ISCO column, 0-45% ethyl acetate in hexanes) gave 80 mg (85%) of [6-fluoro-4-(4-methansulfonyl-phenyl)-3-methyl-naphthalen-2-yl]-acetic acid methyl ester. $^1$H NMR (300 MHz, $CDCl_3$) δ ppm 8.11 (d, J=8.2 Hz, 2 H), 7.82 (dd, J=8.7, 5.9 Hz, 1 H), 7.77 (s, 1 H), 7.49 (d, J=8.2 Hz, 2 H), 7.21 (td, J=8.7, 2.3 Hz, 1 H), 6.77 (dd, J=11.2, 2.3 Hz, 1 H), 3.87 (s, 2 H), 3.74 (s, 3 H), 3.20 (s, 3 H), 2.13 (s, 3 H). HRMS calcd. for $C_{21}H_{20}FO_4S$ [(M+H)$^+$] 387.1061, obsd. 387.1059.

[6-Fluoro-4-(4-methansulfonyl-phenyl)-3-methyl-naphthalen-2-yl]-acetic acid

To a solution of [6-fluoro-4-(4-methansulfonyl-phenyl)-3-methyl-naphthalen-2-yl]-acetic acid methyl ester (77.7 mg, 0.2 mmol) in THF (10 mL) was added a solution of lithium hydroxide monohydrate (83.92 mg, 2.0 mmol) in water (2 mL) at room temperature. The resulting clear solution was stirred for 15 hours. The reaction mixture was concentrated to remove THF. The residue was diluted with water (~30 mL) to obtain a clear solution. The basic aqueous layer was acidified with 1.0 N hydrochloric acid. The precipitated solids were collected by filtration and washed with water and hexanes. After drying in air, [6-fluoro-4-(4-methansulfonyl-phenyl)-3-methyl-naphthalen-2-yl]-acetic acid (65 mg, 87%) was isolated as white solid. $^1$H NMR (400 MHz, DMSO-$d_6$) δ ppm 12.51 (br. s, 1 H), 8.11 (d, J=8.2 Hz, 2 H), 8.02 (dd, J=9.0, 6.0 Hz, 1 H), 7.92 (s, 1 H), 7.54 (d, J=8.2 Hz, 2 H), 7.39 (td, J=9.0, 2.3 Hz, 1 H), 6.71 (dd, J=11.3, 2.3 Hz, 1 H), 3.86 (s, 2 H), 3.35 (s, 3 H), 2.08 (s, 3 H). HRMS calcd. for $C_{20}H_{18}FO_4S$ [(M+H)$^+$] 373.0905, obsd. 373.0904.

Example 55

{6-Chloro-3-methyl-4-[4-(morpholino-4-sulfonyl)-phenyl]-naphthalen-2-yl}-acetic acid

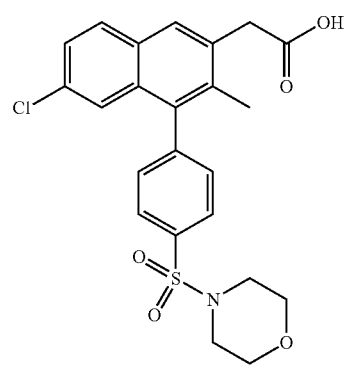 [SMILES: Cc1c(CC(=O)O)cc2ccc(Cl)cc2c1-c1ccc(S(=O)(=O)N2CCOCC2)cc1]

{6-Chloro-3-methyl-4-[4-(morpholino-4-sulfonyl)-phenyl]-naphthalen-2-yl}-acetic acid methyl ester To a mixture of 4-(4-boronobenzenesulfonyl)morpholine (81 mg, 0.3 mmol), (6-chloro-3-methyl-4-trifluoromethanesulfonyloxy-naphthalen-2-yl)-acetic acid methyl ester (99 mg, 0.25 mmol), 1,1'-bis(diphenylphosphino)ferrocenedichloropalladium (II) (37 mg, 0.05 mmol), and cesium carbonate (195 mg, 0.6 mmol) was added anhydrous DMF (5 mL) at room temperature. The resulting light brown suspension was heated to reflux for 15 hours. The reaction mixture was cooled to room temperature and diluted with brine solution and ethyl acetate. The two layers were separated and the aqueous layer was extracted with ethyl acetate. The combined extracts were washed with brine. The organic layer was dried over anhydrous $MgSO_4$, filtered, and concentrated to give the crude residue. Flash chromatography (80 g ISCO column, 0-60% ethyl acetate in hexanes) afforded {6-chloro-3-methyl-4-[4-(morpholino-4-sulfonyl)-phenyl]-naphthalen-2-yl}-acetic acid methyl ester (35 mg, 30%). HRMS calcd. for $C_{24}H_{25}ClNO_5S$ [(M+H)$^+$] 474.1137, obsd. 474.1137.

{6-Chloro-3-methyl-4-[4-(morpholino-4-sulfonyl)-phenyl]-naphthalen-2-yl}-acetic acid To a solution of {6-chloro-3-methyl-4-[4-(morpholino-4-sulfonyl)-phenyl]-naphthalen-2-yl}-acetic acid methyl ester (30 mg, 0.063 mmol) in THF (5 mL) was added a solution of lithium hydroxide monohydrate (41.96 mg, 1.0 mmol) in water (1 mL) at room temperature. The resulting clear solution was stirred for 15 hours and then THF was removed under vacuum. The residue was diluted with water (~30 mL) to obtain a clear solution. This solution was acidified with 1.0 N hydrochloric acid. The resulting solids were collected by filtration and washed with water and hexanes. Purification by preparatory HPLC afforded {6-chloro-3-methyl-4-[4-(morpholino-4-sulfonyl)-phenyl]-naphthalen-2-yl}-acetic acid (15 mg, 52%) as a white solid. $^1$H NMR (400 MHz, DMSO-$d_6$) δ ppm 12.28 (br. s, 1 H), 7.90 (d, J=8.1 Hz, 2 H), 7.84-7.89 (m, 1 H), 7.55 (d, J=8.1 Hz, 2 H), 7.43-7.50 (m, 1 H), 7.39 (t, J=7.8 Hz, 1 H), 7.12 (d, J=8.5 Hz, 1 H), 3.86 (br. s, 2 H), 3.70 (t, J=4.3 Hz, 4 H), 2.99 (t, J=4.3 Hz, 4 H), 2.08 (s, 3 H). MS calcd. for $C_{23}H_{23}ClNO_5S$ [(M+H)$^+$] 459.9, obsd. 460.0.

Example 56

{6-Chloro-4-[4-(2-hydroxy-ethylsulfamoyl)-phenyl]-3-methyl-naphthalen-2-yl}-acetic acid

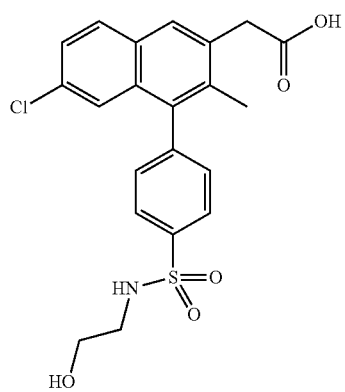 [SMILES: Cc1c(CC(=O)O)cc2ccc(Cl)cc2c1-c1ccc(S(=O)(=O)NCCO)cc1]

{6-Chloro-4-[4-(2-hydroxy-ethylsulfamoyl)-phenyl]-3-methyl-naphthalen-2-yl}-acetic acid methyl ester A stirred solution of [6-chloro-3-methyl-4-(4,4,5,5-tetramethyl-[1,3,2]-dioxaborolan-2-yl)-naphthalen-2-yl]-acetic acid methyl ester (0.200 g, 0.53 mmol) in dimethoxyethane (5 mL) was purged with argon for 5 minutes at room temperature. Tetrakis(triphenylphosphine)palladium(0) (0.082 g, 0.071 mmol), 4-bromo-N-(2-hydroxyethyl)-benzenesulfonamide (0.2 g, 0.71 mmol) and 2.0 M aqueous sodium carbonate (1.0 mL, 2.0 mmol) were added simultaneously to the reaction mixture under argon. The reaction was refluxed for 2 hours and then cooled to room temperature. Water was added and the mixture was extracted twice with ethyl acetate. The combined organic extracts were washed with water and brine, dried over anhydrous sodium sulfate, and concentrated under reduced pressure to give the crude product, which was finally purified using flash chromatography to afford {6-chloro-4-[4-(2-hydroxy-ethylsulfamoyl)-phenyl]-3-methyl-naphthalen-2-yl}-acetic acid methyl ester (0.100 g, 42%) as a solid. MS calcd. for $C_{22}H_{21}ClNO_5S$ [(M−H)$^-$] 446, obsd. 446.4.

{6-Chloro-4-[4-(2-hydroxy-ethylsulfamoyl)-phenyl]-3-methyl-naphthalen-2-yl}-acetic acid Lithium hydroxide monohydrate (0.019 g, 0.45 mmol) was added to a solution of {6-chloro-4-[4-(2-hydroxyethylsulfamoyl)-phenyl]-3-methyl-naphthalen-2-yl}-acetic acid methyl ester (0.05 g, 0.11 mmol) in a 3:1 mixture of THF—H$_2$O mixture (5 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous Na$_2$SO$_4$, and concentrated under reduced pressure to give the crude product. Trituration with hexane gave {6-chloro-4-[4-(2-hydroxyethylsulfamoyl)-phenyl]-3-methyl-naphthalen-2-yl}-acetic acid (0.03 g, 62%) as a solid. $^1$H NMR (DMSO-d$_6$) δ: 12.48 (br. s, 1H), 7.98 (d, J=7.8 Hz, 3H), 7.91 (s, 1H), 7.73 (t, J=5.6 Hz, 1H), 7.49 (d, J=7.8 Hz, 3H), 7.03 (s, 1H), 4.73 (br. s, 1H), 3.86 (s, 2H), 3.44 (d, J=5.4 Hz, 2H), 2.93 (q, J=5.9 Hz, 2H), 2.08 (s, 3H). MS calcd. for $C_{21}H_{21}ClNO_5S$ [(M+H)$^+$] 434, obsd. 434.2.

Example 57

{6-Fluoro-4-[4-(2-hydroxy-ethylsulfamoyl)-phenyl]-3-methyl-naphthalen-2-yl}-acetic acid

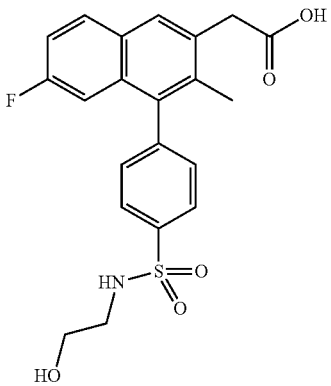 [SMILES: Cc1c(CC(=O)O)cc2ccc(F)cc2c1-c1ccc(S(=O)(=O)NCCO)cc1]

{6-Fluoro-4-[4-(2-hydroxy-ethylsulfamoyl)-phenyl]-3-methyl-naphthalen-2-yl}-acetic acid methyl ester A stirred solution of [6-fluoro-3-methyl-4-(4,4,5,5-tetramethyl-[1,3,2]-dioxaborolan-2-yl)-naphthalen-2-yl]-acetic acid methyl ester (0.200 g, 0.56 mmol) in dimethoxyethane (5 mL) was purged with argon for 5 minutes at room temperature. Tetrakis(triphenylphosphine)palladium(0) (0.065 g, 0.056 mmol), 4-bromo-N-(2-hydroxyethyl)-benzenesulfonamide (0.157 g, 0.56 mmol) and 2.0 M aqueous sodium carbonate (0.8 mL, 1.6 mmol) were added simultaneously to the reaction mixture under argon. The reaction was refluxed for 2 hours and then cooled to room temperature. Water was added and the mixture was extracted twice with ethyl acetate. The combined organic extracts were washed with water and brine, dried over anhydrous sodium sulfate, and concentrated under reduced pressure to give the crude product, which was finally purified using flash chromatography to afford {6-fluoro-4-[4-(2-hydroxyethylsulfamoyl)-phenyl]-3-methyl-naphthalen-2-yl}-acetic acid methyl ester (0.070 g, 29%) as a solid. MS calcd. for $C_{22}H_{21}FNO_5S$ [(M−H)$^-$] 430, obsd. 430.3.

{6-Fluoro-4-[4-(2-hydroxyethylsulfamoyl)-phenyl]-3-methyl-naphthalen-2-yl}-acetic acid Lithium hydroxide monohydrate (0.027 g, 0.64 mmol) was added to a solution of 6-fluoro-4-[4-(2-hydroxyethylsulfamoyl)-phenyl]-3-methyl-naphthalen-2-yl}-acetic acid methyl ester (0.07 g, 0.16 mmol) in a 3:1 mixture of THF—H$_2$O mixture (6 mL). The reaction mixture was stirred for 16 hours at room temperature. The reaction mixture was concentrated to remove the THF, and the crude material was diluted with water, acidified [pH~2] with a 6 N aqueous solution of hydrochloric acid. The mixture was extracted twice with ethyl acetate. The collected organic layers were washed with water and brine, dried over anhydrous Na$_2$SO$_4$, and concentrated under reduced pressure to give the crude product. Trituration with hexane gave {6-fluoro-4-[4-(2-hydroxyethylsulfamoyl)-phenyl]-3-methyl-naphthalen-2-yl}-acetic acid (0.04 g, 59%) as a solid. $^1$H NMR (400 MHz, DMSO-d$_6$) δ ppm 12.51 (br. s, 1 H), 7.99-8.08 (m, 1 H), 7.97 (d, J=8.08 Hz, 2 H), 7.90 (s, 1 H), 7.71-7.77 (m, 1 H), 7.48 (d, J=8.08 Hz, 2 H), 7.35-7.44 (m, 1 H), 6.66-6.73 (m, 1 H), 4.72-4.78 (m, 1 H), 3.85 (s, 2 H), 3.42 (br. s., 2 H), 2.86-2.97 (m, 2 H), 2.08 (s, 3 H). MS calcd. for $C_{21}H_{21}FNO_5S$ [(M+H)$^+$] 418, obsd. 418.2.

Example 58

[6-Fluoro-4-(5-methanesulfonyl-pyridin-2-yl)-3-methyl-naphthalen-2-yl]-acetic acid

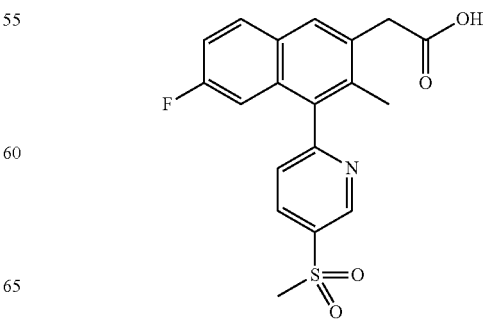

[6-Fluoro-4-(5-methanesulfonyl-pyridin-2-yl)-3-methyl-naphthalen-2-yl]-acetic acid methyl ester A mixture of [6-fluoro-3-methyl-4-(4,4,5,5-tetramethyl-[1,3,2]-dioxaborolan-2-yl)-naphthalen-2-yl]-acetic acid methyl ester (0.130 g, 0.36 mmol), 2-bromo-5-methanesulfonylpyridine (0.086 g, 0.36 mmol), [1,1'-bis(diphenylphosphino)ferrocene]-dichloropalladium(II) (0.005 g, 0.0068 mmol), and 1.0 M aqueous sodium carbonate (0.4 mL, 0.4 mmol) in 1:1 THF-toluene (4 mL) was heated at 80° C. for 20 hours. The reaction mixture was cooled to room temperature, and diluted with ethyl acetate. The resulting mixture was washed with water. The organic layer was dried ($Na_2SO_4$), filtered, and concentrated to give an oily yellow solid. Flash chromatography (40 g Analogix column, 5-60% ethyl acetate in hexanes) gave [6-fluoro-4-(5-methanesulfonyl-pyridin-2-yl)-3-methyl-naphthalen-2-yl]acetic acid methyl ester (0.014 g, 10%) as a solid. $^1$H NMR (300 MHz, DMSO-$d_6$) δ ppm 9.27 (d, J=3.00 Hz, 1 H), 8.49 (dd, J=8.00, 3.00 Hz, 1 H), 8.04 (dd, J=8.80, 6.60 Hz, 1 H), 7.97 (s, 1 H), 7.73 (d, J=9.00 Hz, 1 H), 7.41 (td, J=8.00, 3.20 Hz, 1 H), 6.72-6.78 (m, 1 H), 3.97-3.99 (m, 2 H), 3.65 (s, 3 H), 3.46 (s, 3 H), 2.05 (s, 3 H).

[6-Fluoro-4-(5-methanesulfonyl-pyridin-2-yl)-3-methyl-naphthalen-2-yl]-acetic acid Lithium hydroxide monohydrate (0.0045 g, 0.107 mmol) was added to a mixture of [6-fluoro-4-(5-methanesulfonyl-pyridin-2-yl)-3-methyl-naphthalen-2-yl]acetic acid methyl ester (0.014 g, 0.036 mmol) in a 1:1 mixture of THF—$H_2O$ mixture (2 mL). The reaction mixture was stirred for 5 hours at room temperature. The reaction mixture was concentrated to remove the THF, and the aqueous residue was combined with a 1.0 N aqueous solution of hydrochloric acid. The resulting mixture was extracted with ethyl acetate. The collected organic layers were dried over anhydrous $MgSO_4$, filtered, and concentrated to provide [6-fluoro-4-(5-methanesulfonyl-pyridin-2-yl)-3-methyl-naphthalen-2-yl]acetic acid (0.009 g) as a white solid. The final product contained a significant amount of water as an impurity. $^1$H NMR (300 MHz, DMSO-$d_6$) δ ppm 12.35 (br. s, 1 H), 9.26 (dd, J=2.42, 0.60 Hz, 1 H), 8.49 (dd, J=8.00, 2.26 Hz, 1 H), 8.03 (dd, J=8.80, 6.80 Hz, 1 H), 7.95 (s, 1 H), 7.73 (d, J=8.15 Hz, 1 H), 7.40 (td, J=8.80, 2.40 Hz, 1 H), 6.75 (dd, J=11.00, 2.40 Hz, 1 H), 3.87 (s, 2 H), 3.45 (s, 3 H), 2.07 (s, 3 H). MS calcd. for $C_{19}H_{17}FNO_4S$ [(M+H)$^+$] 374, obsd. 374.0.

Example 59

[4-(4-Benzenesulfonylamino-phenyl)-6-fluoro-3-methyl-naphthalen-2-yl]-acetic acid

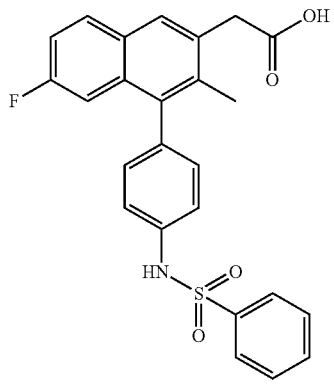 [SMILES: Cc1c(CC(=O)O)cc2ccc(F)cc2c1-c1ccc(NS(=O)(=O)c2ccccc2)cc1]

[4-(4-Benzenesulfonylamino-phenyl)-6-fluoro-3-methyl-naphthalen-2-yl]-acetic acid methyl ester To a solution of [4-(4-amino-phenyl)-6-fluoro-3-methyl-naphthalen-2-yl]-acetic acid methyl ester (55 mg, 0.17 mmol) and benzenesulfonyl chloride (61 mg, 0.34 mmol) in THF (3 mL) was added diisopropylethylamine (62 mg, 0.49 mmol) at 0° C. under nitrogen. The reaction mixture was warmed to room temperature and stirred for 3 hours. The solvent was removed under vacuum and the residue was diluted with water (10 mL). The mixture was extracted with ethyl acetate (2×20 mL). The combined organic extracts were washed with brine solution (50 mL) and dried over anhydrous magnesium sulfate. Filtration of the drying agent and concentration of the solvent under vacuum gave the crude residue which was purified using an ISCO (12 g) column, eluting with 2-25% ethyl acetate in hexanes, to afford [4-(4-benzenesulfonylamino-phenyl)-6-fluoro-3-methyl-naphthalen-2-yl]-acetic acid methyl ester (38 mg, 48%) as a white solid. $^1$H NMR (300 MHz, CDCl$_3$) δ ppm 7.84 (d, J=7.5 Hz, 2 H), 7.77 (dd, J=9.1, 6.0 Hz, 1 H), 7.70 (s, 1 H), 7.59 (t, J=7.5 Hz, 1 H), 7.49 (t, J=7.5 Hz, 2 H), 7.15-7.22 (m, 3 H), 7.10 (d, J=8.2 Hz, 2 H), 6.80 (s, 1 H), 6.71 (dd, J=11.3, 2.3 Hz, 1 H), 3.78-3.90 (m, 2 H), 3.73 (s, 3 H), 2.09 (s, 3 H). HRMS calcd. for $C_{26}H_{21}FNO_4S$ [(M–H)$^-$] 462.1181, obsd. 462.1179.

[4-(4-Benzenesulfonylamino-phenyl)-6-fluoro-3-methyl-naphthalen-2-yl]-acetic acid To a solution of [4-(4-benzenesulfonylamino-phenyl)-6-fluoro-3-methyl-naphthalen-2-yl]-acetic acid methyl ester (38 mg, 0.08 mmol) in THF (2 mL) was added a solution of lithium hydroxide monohydrate (10 mg, 0.25 mmol) in water (1 mL) and methanol (1 mL) plus sodium hydroxide solution (1 ml, 1.0 N) at room temperature. The resulting clear solution was stirred for 4 h and then the solvents were removed under vacuum. The residue was diluted with water (10 mL). The mixture was acidified with 1.0 N hydrochloric acid and extracted with ethyl acetate (2×20 mL). The combined organic extracts were washed with brine solution (20 mL) and dried over anhydrous magnesium sulfate. Filtration of the drying agent and concentration of the solvent under vacuum provided the desired [4-(4-benzenesulfonylamino-phenyl)-6-fluoro-3-methyl-naphthalen-2-yl]-acetic acid (34 mg, 92%) as a light brown foam. $^1$H NMR (300 MHz, DMSO-$d_6$) δ ppm 12.43 (br. s, 1 H), 10.44 (s, 1 H), 7.88-8.02 (m, 1 H), 7.76-7.87 (m, 3 H), 7.50-7.71 (m, 3 H), 7.33 (t, J=7.7 Hz, 1 H), 7.24 (d, J=8.0 Hz, 2 H), 7.09 (d, J=8.0 Hz, 2 H), 6.58 (d, J=11.2 Hz, 1 H), 3.80 (br. s, 2 H), 2.00 (s, 3 H). HRMS calcd. for $C_{25}H_{19}FNO_4S$ [(M–H)$^-$] 448.1024, obsd. 448.1022.

Example 60

{4-[4-(3,5-Bis-trifluoromethyl-benzenesulfonylamino)-phenyl]-6-fluoro-3-methyl-naphthalen-2-yl}-acetic acid

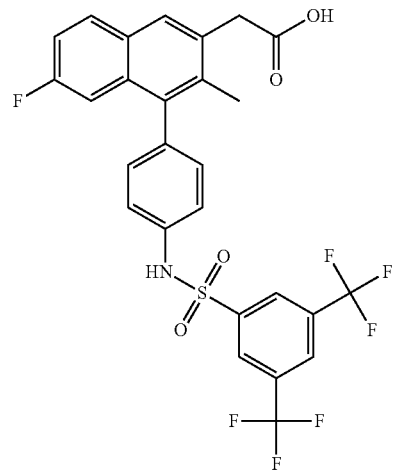 [SMILES: Cc1c(CC(=O)O)cc2ccc(F)cc2c1-c1ccc(NS(=O)(=O)c2cc(C(F)(F)F)cc(C(F)(F)F)c2)cc1]

{4-[4-(3,5-Bis-trifluoromethyl-benzenesulfonylamino)-phenyl]-6-fluoro-3-methyl-naphthalen-2-yl}-acetic acid methyl ester To a solution of [4-(4-amino-phenyl)-6-fluoro-3-methyl-naphthalen-2-yl]-acetic acid methyl ester (55 mg, 0.17 mmol) and 3,5-bis(trifluoromethyl)benzenesulfonyl chloride (54 mg, 0.17 mmol) in THF (3 mL) was added diisopropylethylamine (62 mg, 0.48 mmol) at 0° C. under nitrogen. After addition, the reaction mixture was warmed to room temperature and stirred for 3 hours. The solvent was removed under vacuum and the residue was diluted with water (10 mL). The mixture was extracted with ethyl acetate (2×20 mL). The combined organic extracts were washed with brine solution (20 mL) and dried over anhydrous magnesium sulfate. Filtration of the drying agent and concentration of the solvent under vacuum gave the crude residue which was purified using an ISCO (12 g) column, eluting with 2-25% ethyl acetate in hexanes, to afford {4-[4-(3,5-bis-trifluoromethyl-benzenesulfonylamino)-phenyl]-6-fluoro-3-methyl-naphthalen-2-yl}-acetic acid methyl ester (21.5 mg, 21%) as a light brown solid. $^1$H NMR (300 MHz, CDCl$_3$) δ ppm 8.23 (s, 2 H), 8.09 (s, 1 H), 7.78 (dd, J=8.8, 5.7 Hz, 1 H), 7.73 (s, 1 H), 7.11-7.24 (m, 5 H), 7.04 (s, 1 H), 6.73 (d, J=10.9 Hz, 1 H), 3.87 (s, 2 H), 3.75 (s, 3 H), 2.07 (s, 3 H). HRMS calcd. for $C_{28}H_{19}F_7NO_4S$ [(M−H)$^−$] 598.0928, obsd. 598.0925.

{4-[4-(3,5-Bis-trifluoromethyl-benzenesulfonylamino)-phenyl]-6-fluoro-3-methyl-naphthalen-2-yl}-acetic acid To a solution of {4-[4-(3,5-bis-trifluoromethyl-benzenesulfonylamino)-phenyl]-6-fluoro-3-methyl-naphthalen-2-yl}-acetic acid methyl ester (21 mg, 0.035 mmol) in ethanol (2 mL) was added sodium hydroxide solution (105 uL, 1.0 N,) at room temperature. The resulting clear solution was stirred for 4 h. Then, the solvents were removed under vacuum and the residue was diluted with water (10 mL), acidified with 1.0 N hydrochloric acid, extracted with ethyl acetate (2×20 mL). The combined organic extracts were washed with brine solution (20 mL) and dried over anhydrous magnesium sulfate. Filtration of the drying agent and concentration of the solvent under vacuum provided the desired {4-[4-(3,5-bis-trifluoromethyl-benzenesulfonylamino)-phenyl]-6-fluoro-3-methyl-naphthalen-2-yl}-acetic acid (17 mg, 83%) as a light brown foam. $^1$H NMR (300 MHz, DMSO-d$_6$) δ ppm 12.45 (br. s, 1 H), 10.59 (br. s, 1 H), 8.53 (br. s, 1 H), 8.21 (s, 2 H), 7.89-8.03 (m, 1 H), 7.83 (s, 1 H), 7.34 (t, J=8.2 Hz, 1 H), 7.25 (d, J=7.5 Hz, 2 H), 7.16 (d, J=7.8 Hz, 2 H), 6.59 (d, J=11.2 Hz, 1 H), 3.81 (br. s, 2 H), 1.98 (s, 3 H). HRMS calcd. for $C_{27}H_{17}F_7NO_4S$ [(M−H)$^−$] 584.0772, obsd. 584.0771.

Example 61

[4-(4-Benzenesulfonylamino-phenyl)-6-chloro-3-methyl-naphthalen-2-yl]-acetic acid

[4-(4-Benzenesulfonylamino-phenyl)-6-chloro-3-methyl-naphthalen-2-yl]-acetic acid methyl ester To a solution of [4-(4-amino-phenyl)-6-chloro-3-methyl-naphthalen-2-yl]-acetic acid methyl ester (100 mg, 0.29 mmol) and benzenesulfonyl chloride (105 mg, 0.59 mmol) in THF (5.5 mL) was added diisopropylethylamine (0.15 ml, 0.85 mmol) at 0° C. under nitrogen. After addition, the reaction mixture was warmed to room temperature and stirred for 3 hours. The solvent was removed under vacuum and the residue was diluted with water (10 mL). Then, the mixture was extracted with ethyl acetate (2×20 mL). The combined organic extracts were washed with brine solution (30 mL) and dried over anhydrous magnesium sulfate. Filtration of the drying agent and concentration of the solvent under vacuum gave the crude residue which was purified using an ISCO (40 g) column, eluting with 5-25% ethyl acetate in hexanes, to afford [4-(4-benzenesulfonylamino-phenyl)-6-chloro-3-methyl-naphthalen-2-yl]-acetic acid methyl ester (108 mg, 76%) as a white foam. HRMS calcd. for $C_{26}H_{21}ClNO_4S$ [(M−H)$^−$] 478.0885, obsd. 478.0884.

[4-(4-Benzenesulfonylamino-phenyl)-6-chloro-3-methyl-naphthalen-2-yl]-acetic acid To a solution of [4-(4-benzenesulfonylamino-phenyl)-6-chloro-3-methyl-naphthalen-2-yl]-acetic acid methyl ester (103 mg, 0.22 mmol) in ethanol (8 mL) was added a solution of sodium hydroxide solution (645 uL, 1.0 N) at room temperature. The resulting clear solution was stirred overnight The solvents were removed under vacuum and the residue was diluted with water (10 mL), acidified with 1.0 N hydrochloric acid, and extracted with ethyl acetate (2×20 mL). The combined organic extracts were washed with brine solution (20 mL) and dried over anhydrous magnesium sulfate. Filtration of the drying agent and concentration of the solvent under vacuum provided the desired [4-(4-benzenesulfonylamino-phenyl)-6-fluoro-3-methyl-naphthalen-2-yl]-acetic acid (34 mg, 34%) as a light brown foam. $^1$H NMR (300 MHz, DMSO-d$_6$) δ ppm 12.43 (br. s, 1 H), 10.44 (s, 1 H), 7.88-8.02 (m, 1 H), 7.76-7.87 (m, 3 H), 7.50-7.71 (m, 3 H), 7.33 (t, J=7.7 Hz, 1 H), 7.24 (d, J=8.0 Hz, 2 H), 7.09 (d, J=8.0 Hz, 2 H), 6.58 (d, J=11.2 Hz, 1 H), 3.80 (br. s, 2 H), 2.00 (s, 3 H). HRMS calcd. for $C_{25}H_{19}ClNO_4S$ [(M−H)$^−$] 464.0729, obsd. 464.0731.

Example 62

{6-Chloro-3-methyl-4-[4-(2-trifluoromethyl-benzenesulfonylamino)-phenyl]-naphthalen-2-yl}-acetic acid

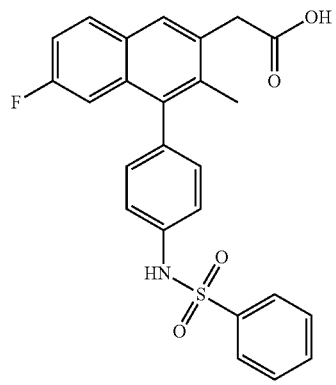 [SMILES: Cc1c(CC(=O)O)cc2ccc(F)cc2c1-c1ccc(NS(=O)(=O)c2ccccc2)cc1]

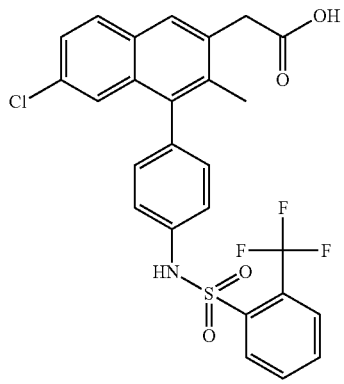 [SMILES: Cc1c(CC(=O)O)cc2ccc(Cl)cc2c1-c1ccc(NS(=O)(=O)c2ccccc2C(F)(F)F)cc1]

{6-Chloro-3-methyl-4-[4-(2-trifluoromethyl-benzenesulfonylamino)-phenyl]-naphthalen-2-yl}-acetic acid methyl ester To a solution of [4-(4-amino-phenyl)-6-chloro-3-methyl-naphthalen-2-yl]-acetic acid methyl ester (100 mg, 0.29 mmol) and 2-trifluoromethyl-benzenesulfonyl chloride (146 mg, 0.59 mmol) in THF (5.5 mL) was added diisopropylethylamine (0.15 mL, 0.85 mmol) at 0° C. under nitrogen. After addition, the reaction mixture was warmed to room temperature and stirred for 3 hours. The solvent was removed under vacuum and the residue was diluted with water (10 mL). Then, the organic compound was extracted into ethyl acetate (2×20 mL). The combined organic extracts were washed with brine solution (30 mL) and dried over anhydrous magnesium sulfate. Filtration of the drying agent and concentration of the solvent under vacuum gave the crude residue which was purified by using an ISCO (40 g) column chromatography eluting with 5-30% ethyl acetate in hexanes to afford {6-chloro-3-methyl-4-[4-(2-trifluoromethyl-benzenesulfonylamino)-phenyl]-naphthalen-2-yl}-acetic acid methyl ester (132 mg, 82%) as a light yellow foam. $^1$H NMR (300 MHz, DMSO-$d_6$) δ ppm 10.80 (s, 1 H), 8.16 (d, J=7.2 Hz, 1 H), 8.03 (dd, J=7.2, 1.7 Hz, 1 H), 7.82-7.96 (m, 4 H), 7.45 (dd, J=8.8, 1.6 Hz, 1 H), 7.25 (d, J=8.5 Hz, 2 H), 7.12 (d, J=8.5 Hz, 2 H), 6.95 (d, J=1.6 Hz, 1 H), 3.92 (s, 2 H), 3.63 (s, 3 H), 1.98 (s, 3H). HRMS calcd. for $C_{27}H_{20}ClF_3NO_4S$ [(M−H)$^-$] 546.0759, obsd. 546.0762.

{6-Chloro-3-methyl-4-[4-(2-trifluoromethyl-benzenesulfonylamino)-phenyl]-naphthalen-2-yl}-acetic acid To a solution of {6-chloro-3-methyl-4-[4-(2-trifluoromethyl-benzenesulfonylamino)-phenyl]-naphthalen-2-yl}-acetic acid methyl ester (125 mg, 0.23 mmol) in ethanol (10 mL) was added a solution of sodium hydroxide solution (684 uL, 1.0 N) at room temperature. The resulting clear solution was stirred overnight. Then, the solvents were removed under vacuum and the residue was diluted with water (10 mL), acidified with 1.0 N hydrochloric acid and extracted with ethyl acetate (2×20 mL). The combined organic extracts were washed with brine solution (20 mL) and dried over anhydrous magnesium sulfate. Filtration of the drying agent and concentration of the solvent under vacuum provided the desired {6-chloro-3-methyl-4-[4-(2-trifluoromethyl-benzenesulfonylamino)-phenyl]-naphthalen-2-yl}-acetic acid. $^1$H NMR (300 MHz, DMSO-$d_6$) δ ppm 12.47 (br. s, 1 H), 10.80 (br. s, 1 H), 8.02-8.23 (m, 1 H), 7.97-8.07 (m, 1 H), 7.85-7.95 (m, 3 H), 7.83 (s, 1 H), 7.44 (dd, J=8.8, 1.6 Hz, 1 H), 7.24 (d, J=8.5 Hz, 2 H), 7.13 (d, J=8.5 Hz, 2 H), 6.94 (d, J=1.6 Hz, 1 H), 3.81 (s, 2 H), 2.00 (s, 3 H). HRMS calcd. for $C_{26}H_{18}ClF3NO_4S$ [(M−H)$^-$] 532.0602, obsd. 532.0602.

Example 63

{6-Chloro-3-methyl-4-[4-(toluene-2-sulfonylamino)-phenyl]-naphthalen-2-yl}-acetic acid

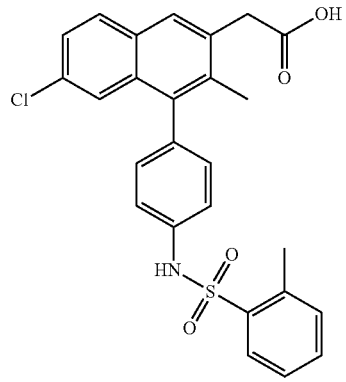 [SMILES: Cc1ccccc1S(=O)(=O)Nc1ccc(-c2c(C)c(CC(=O)O)cc3ccc(Cl)cc23)cc1]

{6-Chloro-3-methyl-4-[4-(toluene-2-sulfonylamino)-phenyl]-naphthalen-2-yl}-acetic acid methyl ester To a solution of [4-(4-Amino-phenyl)-6-chloro-3-methyl-naphthalen-2-yl]-acetic acid methyl ester (100 mg, 0.29 mmol) and 2-Methyl-benzenesulfonyl chloride (113 mg, 0.59 mmol) in THF (5.5 mL) was added diisopropylethylamine (0.15 ml, 0.85 mmol) at 0° C. under nitrogen. After addition, the reaction mixture was warmed to room temperature and stirred for 3 hours. The solvent was removed under vacuum. The residue was diluted with water (10 mL) and the mixture was extracted with ethyl acetate (2×20 mL). The combined organic extracts were washed with brine solution (30 mL) and dried over anhydrous magnesium sulfate. Filtration of the drying agent and concentration of the solvent under vacuum gave the crude residue which was purified using an ISCO (40 g) column, eluting with 5-30% ethyl acetate in hexanes, to afford {6-chloro-3-methyl-4-[4-(toluene-2-sulfonylamino)-phenyl]-naphthalen-2-yl}-acetic acid methyl ester (90 mg, 62.1%) as a white foam. HRMS calcd. for $C_{27}H_{23}ClFNO_4S$ [(M−H)$^-$] 492.1042, obsd. 492.1042.

{6-Chloro-3-methyl-4-[4-(toluene-2-sulfonylamino)-phenyl]-naphthalen-2-yl}-acetic acid To a solution of {6-chloro-3-methyl-4-[4-(toluene-2-sulfonylamino)-phenyl]-naphthalen-2-yl}-acetic acid methyl ester (85 mg, 0.17 mmol) in ethanol (7 mL) was added a solution of sodium hydroxide solution (516 uL, 1.0 N) at room temperature. The resulting clear solution was stirred overnight. Then, the solvents were removed under vacuum and the residue was diluted with water (10 mL), acidified with 1.0 N hydrochloric acid, and extracted with ethyl acetate (2×20 mL). The combined organic extracts were washed with brine solution (20 mL) and dried over anhydrous magnesium sulfate. Filtration of the drying agent and concentration of the solvent under vacuum provided the desired {6-chloro-3-methyl-4-[4-(toluene-2-sulfonylamino)-phenyl]-naphthalen-2-yl}-acetic acid as a light brown foam. $^1$H NMR (300 MHz, DMSO-$d_6$) δ ppm 12.44 (br. s, 1 H), 10.54 (br. s, 1 H), 7.88-7.95 (m, 2 H), 7.82 (s, 1 H), 7.48-7.58 (m, 1 H), 7.35-7.46 (m, 3 H), 7.22 (d, J=8.5 Hz, 2 H), 7.08 (d, J=8.5 Hz, 2 H), 6.92 (d, J=1.5 Hz, 1 H), 3.80 (s, 2 H), 2.63 (s, 3 H), 1.99 (s, 3 H). HRMS calcd. for $C_{26}H_{21}ClNO_4S$ [(M−H)$^-$] 478.0885, obsd. 478.0885.

Example 64

[4-(4-Acetylamino-phenyl)-6-chloro-3-methyl-naphthalen-2-yl]-acetic acid

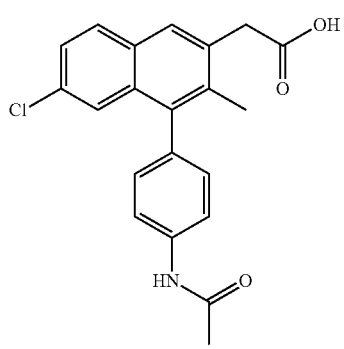 [SMILES: CC(=O)Nc1ccc(-c2c(C)c(CC(=O)O)cc3ccc(Cl)cc23)cc1]

[4-(4-Acetylamino-phenyl)-6-chloro-3-methyl-naphthalen-2-yl]-acetic acid methyl ester To a solution of [4-(4-Amino-phenyl)-6-chloro-3-methyl-naphthalen-2-yl]-acetic acid methyl ester (115 mg, 0.34 mmol) and acetic anhydride (68.8 mg, 67 mmol) were mixed together under nitrogen and then pyridine (3 mL) was added to afford clear solution which was stirred for 10 minutes. The mixture was diluted with ethyl acetate (20 mL) and washed with 1.0 N HCl solution (10 mL), brine solution (20 mL) and dried over anhydrous magnesium sulfate. Filtration of the drying agent and concentration of the solvent under vacuum gave [4-(4-acetylamino-phenyl)-6-chloro-3-methyl-naphthalen-2-yl]-acetic acid methyl ester (120 mg, 93.1%) as a white solid. $^1$H NMR (300 MHz, DMSO-d$_6$) δ ppm 10.13 (s, 1 H), 7.94 (d, J=8.8 Hz, 1 H), 7.86 (s, 1 H), 7.76 (d, J=8.2 Hz, 2 H), 7.46 (dd, J=8.8, 1.8 Hz, 1 H), 7.11-7.19 (m, 3 H), 3.95 (s, 2 H), 3.65 (s, 3 H), 2.10 (s, 3 H), 2.07 (s, 3 H). HRMS calcd. for $C_{22}H_{19}ClNO_3$ [(M−H)$^-$.

[4-(4-Acetylamino-phenyl)-6-chloro-3-methyl-naphthalen-2-yl]-acetic acid

To a solution of [4-(4-acetylamino-phenyl)-6-chloro-3-methyl-naphthalen-2-yl]-acetic acid methyl ester (112 mg, 0.29 mmol) in ethanol (3 mL) and THF (3 mL) was added a sodium hydroxide solution (586 uL, 1.0 N) at room temperature. The resulting clear solution was stirred for 4 h. Then, the solvents were removed under vacuum and the residue was diluted with water (10 mL), acidified with 1.0 N hydrochloric acid, and extracted with ethyl acetate (2×20 mL). The combined organic extracts were washed with brine solution (20 mL) and dried over anhydrous magnesium sulfate. Filtration of drying agent and concentration of the solvent under vacuum gave a solid which was treated with hot acetonitrile. After cooling in the refrigerator, the solids were collected by filtration and washed with acetonitrile to give [4-(4-acetylamino-phenyl)-6-chloro-3-methyl-naphthalen-2-yl]-acetic acid (65 mg, 60.2%) as a white solid. $^1$H NMR (300 MHz, DMSO-d$_6$) δ ppm 12.50 (s, 1 H), 10.13 (s, 1 H), 7.93 (d, J=8.8 Hz, 1 H), 7.84 (s, 1 H), 7.76 (d, J=8.2 Hz, 2 H), 7.45 (dd, J=8.8, 1.8 Hz, 1 H), 7.15 (m, 3 H), 3.84 (s, 2 H), 2.10 (br. s., 3 H), 2.09 (br. s., 3 H). HRMS (ES+) calcd. for $C_{21}H_{19}ClNO_3$ [(M+H)$^+$] 368.1048, obsd. 368.1049.

Example 65

[4-(4-Benzoylamino-phenyl)-6-chloro-3-methyl-naphthalen-2-yl]-acetic acid

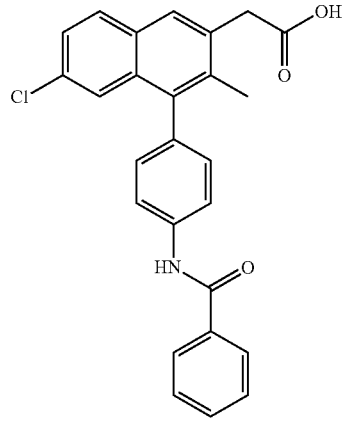 [SMILES: Cc1c(CC(=O)O)cc2ccc(Cl)cc2c1-c1ccc(NC(=O)c2ccccc2)cc1]

[4-(4-Benzoylamino-phenyl)-6-chloro-3-methyl-naphthalen-2-yl]-acetic acid methyl ester To a solution of [4-(4-amino-phenyl)-6-chloro-3-methyl-naphthalen-2-yl]-acetic acid methyl ester (115 mg, 0.34 mmol) and benzoyl chloride (52.64 mg, 0.37 mmol) were mixed together in dichloromethane (5 mL) under nitrogen and then diisopropylethylamine (0.12 mL, 0.67 mmol) was added to afford clear solution. The resulting solution was stirred for 4 hours at room temperature and then concentrated. Ethyl acetate (20 mL) was added and the mixture was washed with water (20 mL) and brine solution (20 mL) and then dried over anhydrous magnesium sulfate. Filtration of the drying agent and concentration of the solvent under vacuum gave a crude residue which was purified using an ISCO (12 g) column, eluting with 5-35% ethyl acetate in hexanes, to afford [4-(4-benzoylamino-phenyl)-6-chloro-3-methyl-naphthalen-2-yl]-acetic acid methyl ester (133 mg, 88.8%) as a white solid. $^1$H NMR (300 MHz, DMSO-d$_6$) δ ppm 10.46 (s, 1 H), 7.93-8.03 (m, 5 H), 7.88 (s, 1 H), 7.51-7.68 (m, 3 H), 7.48 (dd, J=8.6, 1.8 Hz, 1 H), 7.23 (d, J=8.5 Hz, 2 H), 7.18 (d, J=1.8 Hz, 1 H), 3.97 (s, 2 H), 3.66 (s, 3 H), 2.10 (s, 3 H). HRMS calcd. for $C_{27}H_{23}ClNO_3$ [(M+H)$^+$] 444.1361, obsd. 444.1361.

[4-(4-Benzoylamino-phenyl)-6-chloro-3-methyl-naphthalen-2-yl]-acetic acid

To a solution of [4-(4-benzoylamino-phenyl)-6-chloro-3-methyl-naphthalen-2-yl]-acetic acid methyl ester (130 mg, 0.29 mmol) in ethanol (3 mL) and THF (3 mL) was added a solution of sodium hydroxide (879 uL, 1.0 N) at room temperature. The resulting clear solution was stirred overnight. The solvents were removed under vacuum and the residue was diluted with water (10 mL), acidified with 1.0 N hydrochloric acid, and extracted with ethyl acetate (2×20 mL). The combined organic extracts were washed with brine solution (20 mL) and dried over anhydrous magnesium sulfate. Filtration of the drying agent and concentration of the solvent under vacuum afforded (115 mg, 91.3%) [4-(4-benzoylamino-phenyl)-6-chloro-3-methyl-naphthalen-2-yl]-acetic acid as a white solid. $^1$H NMR (300 MHz, DMSO-d$_6$) δ ppm 12.51 (br. s, 1 H), 10.46 (s, 1 H), 7.91-8.04 (m, 5 H), 7.86 (s, 1 H), 7.51-7.68 (m, 3 H), 7.47 (dd, J=8.8, 1.8 Hz, 1 H), 7.23 (d, J=8.5 Hz, 2 H), 7.18 (d, J=1.8 Hz, 1 H), 3.85 (s, 2 H), 2.12 (s, 3 H). HRMS calcd. for $C_{26}H_{21}ClNO_3$ [(M+H)$^+$] 430.1205, obsd. 430.1205.

Example 66

{6-Chloro-3-methyl-4-[4-(3-phenyl-ureido)-phenyl]-naphthalen-2-yl}-acetic acid

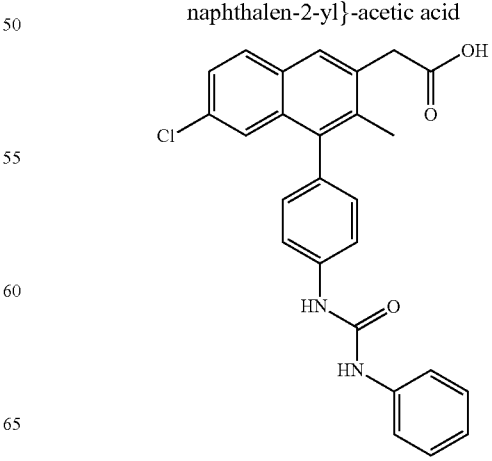

{6-Chloro-3-methyl-4-[4-(3-phenyl-ureido)-phenyl]-naphthalen-2-yl}-acetic acid methyl ester To a mixture of [4-(4-amino-phenyl)-6-chloro-3-methyl-naphthalen-2-yl]-acetic acid methyl ester (115 mg, 0.34 mmol) and isocyanato-benzene (36 mg, 0.29 mmol) was added ethanol (5 mL) under nitrogen. The resulting suspension was stirred at room temperature for 4 hours and the precipitated solids were collected by filtration, washed with cold ethanol, and air-dried to give {6-chloro-3-methyl-4-[4-(3-phenyl-ureido)-phenyl]-naphthalen-2-yl}-acetic acid methyl ester (44 mg, 28%) as a white solid. $^1$H NMR (300 MHz, DMSO-$d_6$) δ ppm 8.86 (s, 1 H), 8.77 (s, 1 H), 7.95 (d, J=8.8 Hz, 1 H), 7.86 (s, 1 H), 7.64 (d, J=8.5 Hz, 2 H), 7.42-7.53 (m, 3 H), 7.30 (t, J=7.8 Hz, 2 H), 7.20 (d, J=1.8 Hz, 1 H), 7.15 (d, J=8.5 Hz, 2 H), 6.94-7.03 (m, 1 H), 3.96 (s, 2 H), 3.66 (s, 3 H), 2.10 (s, 3 H). HRMS calcd. for $C_{27}H_{24}ClN_2O_3$ [(M+H)$^+$] 459.1470, obsd. 459.1470.

{6-Chloro-3-methyl-4-[4-(3-phenyl-ureido)-phenyl]-naphthalen-2-yl}-acetic acid

To a solution of {6-chloro-3-methyl-4-[4-(3-phenyl-ureido)-phenyl]-naphthalen-2-yl}-acetic acid methyl ester (40 mg, 0.09 mmol) in ethanol (2 mL) and THF (3 mL) was added a solution of sodium hydroxide (262 uL, 1.0 N) at room temperature. The resulting mixture was stirred for 5 hours. Then, the solvents were removed under vacuum and the residue was diluted with water (10 mL) and acidified with 1.0 N hydrochloric acid. The mixture was allowed to stand for 3 h, then the solid was filtered off and air-dried to afford {6-chloro-3-methyl-4-[4-(3-phenyl-ureido)-phenyl]-naphthalen-2-yl}-acetic acid (37 mg, 95%) as a white solid. $^1$H NMR (300 MHz, DMSO-$d_6$) δ ppm 12.50 (s, 1 H), 8.86 (s, 1 H), 8.77 (s, 1 H), 7.94 (d, J=8.8 Hz, 1 H), 7.84 (s, 1 H), 7.64 (d, J=8.2 Hz, 2 H), 7.41-7.58 (m, 3 H), 7.30 (t, J=7.8 Hz, 2 H), 7.19 (d, J=1.2 Hz, 1 H), 7.15 (d, J=8.5 Hz, 2 H), 6.99 (t, J=7.2 Hz, 1 H), 3.85 (s, 2 H), 2.12 (s, 3 H). HRMS calcd. for $C_{26}H_{22}ClN_2O_3$ [(M+H)$^+$] 445.1314, obsd. 445.1311.

Example 67

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 μg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from Lonza Inc.), and suspended in PBS containing 10 mM $MgCl_2$ and 0.06% BSA (bovine serum albumin) at 1.5×10$^6$ cells/mL.

The binding reactions (0.2 mL) were performed in 96-well plates at room temperature in PBS containing 1.5×10$^5$ cells, 10 mM $MgCl_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 μL of Microscint™ 20 scintillation fluid (from PerkinElmer, Inc.) to each well of the filter plates. The radioactivity from non-specific binding was determined by replacing compound with 10 μM of 15(R)-15-methyl $PGD_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The $IC_{50}$ value is defined as the concentration of the tested compound that is required for 50% inhibition of total specific binding. In order to calculate the $IC_{50}$ value, the percent inhibition data were determined for 7 concentrations for each compound. The percent inhibition for a compound at each concentration was calculated according to the following formula, [1-(specific binding in the presence of compound)/(total specific binding)]×100. The $IC_{50}$ value was then obtained by fitting the percent inhibition data to a sigmoidal dose-response (4 parameter logistic) model in the XLfit® software Excel add-in program [from ID Business Solutions Ltd., model 205, where F(x)=(A+(B−A)/(1+((C/x)^D)))].

Certain compounds of the foregoing examples were tested using the above Human CRTH2 Receptor Binding Assay, the results of which are shown in Table 1:

TABLE 1

| Example No. | Human CRTH2 Binding $IC_{50}$ (μM) |
|---|---|
| 1 | 0.0029 |
| 54 | 0.040 |
| 55 | 0.0024 |
| 58 | 0.139 |
| 59 | 0.0032 |
| 60 | 0.0056 |
| 61 | 0.0037 |
| 62 | 0.0089 |
| 63 | 0.0083 |
| 64 | 0.0292 |
| 65 | 0.0062 |
| 66 | 0.019 |

Calcium Flux Assay Using Fluorometric Imaging Plate Reader (FLIPR)

Cell Culture Conditions: CHO-K1 cells previously transfected with G-alpha 16 were subsequently transfected with the human CRTH2 receptor and the neomycin resistance gene. Following selection in 800 μg/mL G418 (geneticin), individual clones were assayed for their receptor expression based on staining with an anti human CRTH2 IgG, followed by assaying for their response to 13,14-dihydro-15-keto Prostaglandin $D_2$ (DK-PDG$_2$) (ligand) in the $Ca^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 μg/mL streptomycin, 200 μg/mL hygromycin B, and 800 μg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to $2.5 \times 10^5$ cells/mL with complete growth media. Aliquots of 50 μL were dispensed into BD Falcon™ 384 well black/clear microplates (from BD Biosciences, a division of Becton, Dickinson and Company) and the microplates were placed in a 37° C. $CO_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Activity data for example compounds tested in the above described FLIPR® assay are shown in Table 2:

TABLE 2

| Example No. | FLIPR Assay $IC_{50}$ (μM) |
| --- | --- |
| 1 | 0.0003 |
| 2 | 0.0007 |
| 3 | 0.0039 |
| 4 | 0.0032 |
| 5 | 0.0013 |
| 6 | 0.0010 |
| 7 | 0.0158 |
| 8 | 0.0091 |
| 9 | 0.0037 |
| 10 | 0.0012 |
| 11 | 0.0012 |
| 12 | 0.0140 |
| 13 | 0.0054 |
| 14 | 0.0016 |
| 15 | 0.0092 |
| 16 | 0.0081 |
| 17 | 0.0070 |
| 18 | 0.0023 |
| 19 | 0.0197 |
| 20 | 0.0129 |
| 22 | 0.0044 |
| 23 | 0.0023 |
| 24 | 0.3115 |
| 25 | 0.0447 |
| 26 | 0.0221 |
| 27 | 0.0007 |
| 28 | 0.0011 |
| 29 | 0.0027 |
| 30 | 0.0343 |
| 31 | 0.0067 |
| 32 | 0.0047 |
| 33 | 0.0008 |
| 34 | 0.0009 |
| 35 | 0.0005 |
| 36 | 0.0061 |
| 37 | 0.0015 |
| 38 | 0.0016 |
| 39 | 0.0132 |
| 40 | 0.0031 |
| 42 | 0.0009 |
| 44 | 0.0009 |
| 45 | 0.0015 |
| 46 | 0.0007 |
| 47 | 0.0041 |
| 48 | 0.0018 |
| 49 | 0.0015 |
| 50 | 0.0017 |
| 51 | 0.0004 |
| 52 | 0.0032 |
| 53 | 0.0013 |
| 54 | 0.025 |
| 56 | 0.0056 |
| 57 | 0.0061 |
| 58 | 1.12 |
| 60 | 0.0001 |

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to Alexa Fluor 647.

To determine cellular inhibitory potency, compounds at various concentrations were incubated with $2.5 \times 10^4$ Th2 cells and 500 nM DK-$PGD_2$ for 4 hrs at 37° C. in 200 µL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^D)))$].

Activity data for example compounds tested in the above described DK-$PGD_2$-induced IL-13 production assay are shown in Table 3:

TABLE 3

| Example No. | TH2 IL-13 $IC_{50}$ (µM) |
|---|---|
| 33 | 0.008 |

It is to be understood that the invention is not limited to the particular embodiments of the invention described above, as variations of the particular embodiments may be made and still fall within the scope of the appended claims.

The invention claimed is:

1. A compound of formula (I):

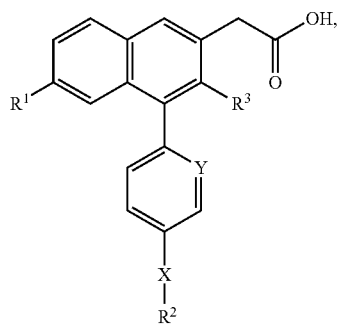

wherein:
X is —$SO_2$—, —$SO_2NH$—, —$NHSO_2$—, —NHC(O)— or —NHC(O)NH—;
Y is N or CH;
$R^1$ is halogen;
$R^2$ is -phenyl, unsubstituted or mono- or bi-substituted independently with lower alkyl, halogen, alkoxy, —$SO_2$-lower alkyl, haloalkyl or —$OCF_3$,
unsubstituted heteroaryl,
lower alkyl, unsubstituted or substituted with hydroxy, unsubstituted phenyl or phenyl substituted with halogen, —$SO_2$-lower alkyl or alkoxy,
unsubstituted cycloalkyl,
unsubstituted heterocycloalkyl, or
N(lower alkyl)$_2$, said lower alkyl independently being unsubstituted or substituted with unsubstituted phenyl or phenyl substituted with methoxy; and
$R^3$ is lower alkyl or hydrogen,
or a pharmaceutically acceptable salt thereof.

2. The compound according to claim 1, wherein X is —$SO_2$— or —$SO_2NH$—.

3. The compound according to claim 1, wherein X is —$NHSO_2$—, —NHC(O)— or —NHC(O)NH—.

4. The compound according to claim 1, wherein X is —$SO_2$—.

5. The compound according to claim 1, wherein Y is CH.

6. The compound according to claim 1, wherein $R^1$ is F or Cl.

7. The compound according to claim 1, wherein $R^1$ is F.

8. The compound according to claim 1, wherein $R^2$ is:
phenyl, unsubstituted or mono- or bi-substituted independently with lower alkyl, halogen,
alkoxy, —$SO_2$-lower alkyl, haloalkyl or —$OCF_3$,
unsubstituted heteroaryl,
unsubstituted cycloalkyl, or
unsubstituted heterocycloalkyl.

9. The compound according to claim 1, wherein $R^2$ is:
lower alkyl, unsubstituted or substituted with hydroxy, unsubstituted phenyl or phenyl substituted with halogen, —$SO_2$-lower alkyl or alkoxy, or
N(lower alkyl)$_2$, said lower alkyl independently being unsubstituted or substituted with unsubstituted phenyl or phenyl substituted with methoxy.

10. The compound according to claim 1, wherein $R^2$ is phenyl, unsubstituted or mono- or bi-substituted independently with lower alkyl, halogen, alkoxy, —$SO_2$-lower alkyl, haloalkyl or —$OCF_3$.

11. The compound according to claim 1, wherein $R^3$ is methyl.

12. The compound according to claim 1, wherein X is —$SO_2$—; Y is C; and $R^2$ is phenyl, unsubstituted or mono- or bi-substituted independently with lower alkyl, halogen, alkoxy, —$SO_2$-lower alkyl, haloalkyl or —$OCF_3$.

13. The compound according to claim 1, wherein $R^2$ is phenyl, unsubstituted or mono- or bi-substituted independently with methyl, chlorine, fluorine, —$CF_3$, —$OCF_3$ or —$OCH_3$.

14. The compound according to claim 1, wherein $R^2$ is pyrrolidinyl, piperidinyl, —N(CH$_2$CH$_3$)$_2$, cyclohexyl, isopropyl, methyl, morpholinyl or hydroxyethyl.

15. The compound according to claim 1, wherein said compound is:
{6-Fluoro-3-methyl-4-[4-(toluene-2-sulfonyl)-phenyl]-naphthalen-2-yl}-acetic acid;
{4-[4-(2-Chloro-benzenesulfonyl)-phenyl]-6-fluoro-3-methyl-naphthalen-2-yl}-acetic acid;
{4-[4-(3-Chloro-benzenesulfonyl)-phenyl]-6-fluoro-3-methyl-naphthalen-2-yl}-acetic acid;
{4-[4-(4-Chloro-benzenesulfonyl)-phenyl]-6-fluoro-3-methyl-naphthalen-2-yl}-acetic acid;

{6-Fluoro-3-methyl-4-[4-(2-trifluoromethyl-benzenesulfonyl)-phenyl]-naphthalen-2-yl}-acetic acid;
{6-Fluoro-3-methyl-4-[4-(2-trifluoromethoxy-benzenesulfonyl)-phenyl]-naphthalen-2-yl}-acetic acid;
{6-Fluoro-3-methyl-4-[4-(4-trifluoromethoxy-benzenesulfonyl)-phenyl]-naphthalen-2-yl}-acetic acid;
{4-[4-(2,4-Dichloro-benzenesulfonyl)-phenyl]-6-fluoro-3-methyl-naphthalen-2-yl}-acetic acid;
{4-[4-(2,5-Dichloro-benzenesulfonyl)-phenyl]-6-fluoro-3-methyl-naphthalen-2-yl}-acetic acid;
{4-[4-(2,4-Difluoro-benzenesulfonyl)-phenyl]-6-fluoro-3-methyl-naphthalen-2-yl}-acetic acid.

16. The compound according to claim 1, wherein said compound is:
{4-[4-(2,6-Difluoro-benzenesulfonyl)-phenyl]-6-fluoro-3-methyl-naphthalen-2-yl}-acetic acid;
{4-[4-(3,5-Bis-trifluoromethyl-benzenesulfonyl)-phenyl]-6-fluoro-3-methyl-naphthalen-2-yl}-acetic acid;
{4-[4-(3,5-Dichloro-benzenesulfonyl)-phenyl]-6-fluoro-3-methyl-naphthalen-2-yl}-acetic acid;
{4-[4-(3,5-Difluoro-benzenesulfonyl)-phenyl]-6-fluoro-3-methyl-naphthalen-2-yl}-acetic acid;
{6-Chloro-4-[4-(2-chloro-benzenesulfonyl)-phenyl]-3-methyl-naphthalen-2-yl}-acetic acid;
{6-Chloro-4-[4-(3-chloro-benzenesulfonyl)-phenyl]-3-methyl-naphthalen-2-yl}-acetic acid;
{6-Chloro-4-[4-(4-chloro-benzenesulfonyl)-phenyl]-3-methyl-naphthalen-2-yl}-acetic acid;
{6-Chloro-3-methyl-4-[4-(2-trifluoromethyl-benzenesulfonyl)-phenyl]-naphthalen-2-yl}-acetic acid;
{6-Chloro-3-methyl-4-[4-(2-trifluoromethoxy-benzenesulfonyl)-phenyl]-naphthalen-2-yl}-acetic acid.

17. The compound according to claim 1, wherein said compound is:
{6-Chloro-3-methyl-4-[4-(4-trifluoromethoxy-benzenesulfonyl)-phenyl]-naphthalen-2-yl}-acetic acid;
{6-Chloro-4-[4-(2,4-dichloro-benzenesulfonyl)-phenyl]-3-methyl-naphthalen-2-yl}-acetic acid;
{6-Chloro-4-[4-(2,5-dichloro-benzenesulfonyl)-phenyl]-3-methyl-naphthalen-2-yl}-acetic acid;
{6-Chloro-4-[4-(2,4-difluoro-benzenesulfonyl)-phenyl]-3-methyl-naphthalen-2-yl}-acetic acid;
{6-Chloro-4-[4-(2,6-difluoro-benzenesulfonyl)-phenyl]-3-methyl-naphthalen-2-yl}-acetic acid;
{4-[4-(3,5-Bis-trifluoromethyl-benzenesulfonyl)-phenyl]-6-chloro-3-methyl-naphthalen-2-yl}-acetic acid;
{6-Chloro-4-[4-(3,5-dichloro-benzenesulfonyl)-phenyl]-3-methyl-naphthalen-2-yl}-acetic acid;
{6-Chloro-4-[4-(3,5-difluoro-benzenesulfonyl)-phenyl]-3-methyl-naphthalen-2-yl}-acetic acid;
{6-Chloro-4-[4-(4-fluoro-phenylsulfamoyl)-phenyl]-3-methyl-naphthalen-2-yl}-acetic acid;
[6-Chloro-3-methyl-4-(4-p-tolylsulfamoyl-phenyl)-naphthalen-2-yl]-acetic acid;
{6-Chloro-3-methyl-4-[4-(4-trifluoromethoxy-phenylsulfamoyl)-phenyl]-naphthalen-2-yl}-acetic acid.

18. The compound according to claim 1, wherein said compound is:
{6-Chloro-4-[4-(3-chloro-2-methyl-phenylsulfamoyl)-phenyl]-3-methyl-naphthalen-2-yl}-acetic acid;
{6-Chloro-4-[4-(3-chloro-phenylsulfamoyl)-phenyl]-3-methyl-naphthalen-2-yl}-acetic acid;
{6-Chloro-3-methyl-4-[4-(pyrrolidine-1-sulfonyl)-phenyl]-naphthalen-2-yl}-acetic acid;
{6-Chloro-3-methyl-4-[4-(piperidine-1-sulfonyl)-phenyl]-naphthalen-2-yl}-acetic acid;
[6-Chloro-4-(4-diethylsulfamoyl-phenyl)-3-methyl-naphthalen-2-yl]-acetic acid;
[6-Chloro-4-(4-cyclohexylsulfamoyl-phenyl)-3-methyl-naphthalen-2-yl]-acetic acid;
[6-Chloro-4-(4-isopropylsulfamoyl-phenyl)-3-methyl-naphthalen-2-yl]-acetic acid;
[4-(4-Benzylsulfamoyl-phenyl)-6-chloro-3-methyl-naphthalen-2-yl]-acetic acid;
{6-Chloro-4-[4-(4-methoxy-benzylsulfamoyl)-phenyl]-3-methyl-naphthalen-2-yl}-acetic acid;
(6-Chloro-4-{4-[isopropyl-(4-methoxy-benzyl)-sulfamoyl]-phenyl}-3-methyl-naphthalen-2-yl)-acetic acid.

19. The compound according to claim 1, wherein said compound is:
{6-Fluoro-4-[4-(4-fluoro-phenylsulfamoyl)-phenyl]-3-methyl-naphthalen-2-yl}-acetic acid;
[6-Fluoro-3-methyl-4-(4-p-tolylsulfamoyl-phenyl)-naphthalen-2-yl]-acetic acid;
{6-Fluoro-3-methyl-4-[4-(4-trifluoromethoxy-phenylsulfamoyl)-phenyl]-naphthalen-2-yl}-acetic acid;
{4-[4-(3-Chloro-2-methyl-phenylsulfamoyl)-phenyl]-6-fluoro-3-methyl-naphthalen-2-yl}-acetic acid;
{4-[4-(3-Chloro-phenylsulfamoyl)-phenyl]-6-fluoro-3-methyl-naphthalen-2-yl}-acetic acid;
{6-Fluoro-3-methyl-4-[4-(pyrrolidine-1-sulfonyl)-phenyl]-naphthalen-2-yl}-acetic acid;
{6-Fluoro-3-methyl-4-[4-(piperidine-1-sulfonyl)-phenyl]-naphthalen-2-yl}-acetic acid;
[4-(4-Diethylsulfamoyl-phenyl)-6-fluoro-3-methyl-naphthalen-2-yl]-acetic acid;
[4-(4-Cyclohexylsulfamoyl-phenyl)-6-fluoro-3-methyl-naphthalen-2-yl]-acetic acid;
[6-Fluoro-4-(4-isopropylsulfamoyl-phenyl)-3-methyl-naphthalen-2-yl]-acetic acid.

20. The compound according to claim 1, wherein said compound is:
[4-(4-Benzylsulfamoyl-phenyl)-6-fluoro-3-methyl-naphthalen-2-yl]-acetic acid;
{6-Fluoro-4-[4-(4-methoxy-benzylsulfamoyl)-phenyl]-3-methyl-naphthalen-2-yl}-acetic acid;
(6-Fluoro-4-{4-[isopropyl-(4-methoxy-benzyl)-sulfamoyl]-phenyl}-3-methyl-naphthalen-2-yl)-acetic acid;
[6-Fluoro-4-(4-methanesulfonyl-phenyl)-3-methyl-naphthalen-2-yl]-acetic acid;
{6-Chloro-3-methyl-4-[4-(morpholine-4-sulfonyl)-phenyl]-naphthalen-2-yl}-acetic acid;
{6-Chloro-4-[4-(2-hydroxy-ethylsulfamoyl)-phenyl]-3-methyl-naphthalen-2-yl}-acetic acid;
{6-Fluoro-4-[4-(2-hydroxy-ethylsulfamoyl)-phenyl]-3-methyl-naphthalen-2-yl}-acetic acid;
[6-Fluoro-4-(5-methanesulfonyl-pyridin-2-yl)-3-methyl-naphthalen-2-yl]-acetic acid.

21. The compound according to claim 1, wherein said compound is:
[4-(4-Benzenesulfonylamino-phenyl)-6-fluoro-3-methyl-naphthalen-2-yl]-acetic acid;
{4-[4-(3,5-Bis-trifluoromethyl-benzenesulfonylamino)-phenyl]-6-fluoro-3-methyl-naphthalen-2-yl}-acetic acid;
[4-(4-Benzenesulfonylamino-phenyl)-6-chloro-3-methyl-naphthalen-2-yl]-acetic acid;
{6-Chloro-3-methyl-4-[4-(2-trifluoromethyl-benzenesulfonylamino)-phenyl]-naphthalen-2-yl}-acetic acid;
{6-Chloro-3-methyl-4-[4-(toluene-2-sulfonylamino)-phenyl]-naphthalen-2-yl}-acetic acid;
[4-(4-Acetylamino-phenyl)-6-chloro-3-methyl-naphthalen-2-yl]-acetic acid;

[4-(4-Benzoylamino-phenyl)-6-chloro-3-methyl-naphthalen-2-yl]-acetic acid; or

{6-Chloro-3-methyl-4-[4-(3-phenyl-ureido)-phenyl]-naphthalen-2-yl}-acetic acid.

22. A pharmaceutical composition, comprising a therapeutically effective amount of a compound according to claim 1 and a pharmaceutically acceptable carrier.

23. A method for treating a respiratory disorder selected from chronic obstructive pulmonary disorder (COPD), asthma, allergic rhinitis and bronchospasm, comprising the step of administering a therapeutically effective amount of a compound according claim 1 to a subject in need thereof.

* * * * *